United States Patent [19]

Tribe

[11] Patent Number: 4,681,852
[45] Date of Patent: Jul. 21, 1987

[54] NOVEL MICROORGANISM AND METHOD

[75] Inventor: David E. Tribe, Wilmington, Del.

[73] Assignee: Austgen-Biojet International Pty, Ltd., Melbourne, Australia

[21] Appl. No.: 459,302

[22] Filed: Jan. 18, 1983

Related U.S. Application Data

[63] Continuation-in-part of Ser. No. 284,801, Jul. 20, 1981, abandoned.

[30] Foreign Application Priority Data

Jul. 18, 1980 [AU] Australia .................. PE4590/80

[51] Int. Cl.[4] .............. C12P 13/22; C12N 15/00; C12R 1/19
[52] U.S. Cl. ................ 435/108; 435/172.1; 435/172.3; 435/849; 935/56; 935/73
[58] Field of Search .......... 435/108, 116, 172, 317, 435/849, 172.3; 935/6, 9, 10, 23, 27, 56, 73

[56] References Cited

U.S. PATENT DOCUMENTS

| | | | |
|---|---|---|---|
| 2,973,304 | 2/1961 | Huang | 435/108 |
| 3,660,235 | 5/1972 | Okamura et al. | 435/108 |
| 3,700,558 | 10/1972 | Thiemann et al. | 435/108 |
| 4,278,765 | 7/1981 | Debabov et al. | 435/172 |
| 4,371,625 | 2/1983 | Tiollais | 935/6 |
| 4,407,952 | 10/1983 | Tsuchida et al. | 435/108 |

FOREIGN PATENT DOCUMENTS 0073868 12/1980 Japan .................. 435/108

OTHER PUBLICATIONS

Tribe et al, 1979, "Hyperproduction of Tryptophan by *E. coli*, Genetic Manipulation of the Pathways Leading to Tryptophan Formation", *Applied & Env. Micro*, v 38(2), pp. 181-190.

Faculty Handbook, Univ. New South Wales, pp. 204-205, 1985.

Lehninger, A., *Biochemistry*, Worth Publishers, Inc., New York, pp. 708-713, (1970).

Zurawski, G. et al, *Proc. Natl. Acad. Sci.*, vol. 75(10), pp. 4271-4275, (1978), "Nucleotide Sequence of the Leader Region of the Phenylalanine Operon of *Escherichia coli*".

Camakaris H. et al., *Jour. of Bacteriol.*, vol. 150(1), pp. 70-75, (1982), "Autoregulation of the tyr R Gene".

Im, S. W. K. et al, *Jour. of Bacteriol.*, vol. 108(1), pp. 400-409, (1971), "Phenylalanine and Tyrosine Biosynthesis in *Escherichia coli* K-12: Mutants Derepressed for 3-Deoxy-D-Arabinoheptulosonic Acid-7-Phosphate Synthetose (phe), 3-Deoxy-D-Arabinoheptulsonic Acid-7-Phosphate Synthetose (tyr), Chorismate Mutase T-Prephanate Dehydrogenase, and Transaminase A".

Herrmann, K. M. et al, editors, *Amino Acids: Biosynthesis and Genetic Regulation*, Addison-Wesley Pub. Co., Mass., pp. 323-338, (1983).

Walker, R., *The Molecular Biology of Enzyme Synthesis*, John Wiley, and Sons, New York, pp. 186-187, (1983).

*Chemical Abstracts*, vol. 98, p. 145, 1983, abstract no. 12330u: Plumridge, J. A. et al, "*Escherichia coli* Phenylalanyl-tRNA Synthetose Operon: Characterization of Mutations Isolated on Multicopy Plasmids".

*Chemical Abstracts*, vol. 98, p. 116, 1983, abstract no. 1197e: Hennecke, H. et al, "A Novel Cloning Vector for the Direct Selection of Recombinant DNA in *E. coli*".

(List continued on next page)

Primary Examiner—Lionel M. Shapiro
Attorney, Agent, or Firm—Browdy and Neimark

[57] ABSTRACT

A method for producing phenylalanine comprising culturing novel strains of the bacteria *Escherichia coli*. The novel strains of *E. coli* are those in which inhibition of the enzyme DAHP synthease by phenylalanine, tyrosine or tryptophan is removed and inhibition of the enzyme chorismate mutase P-prephenate dehydratase by phenylalanine is removed and in which enhanced levels of production of the enzymes DAHP synthease, chorismate mutase P-prephenate dehydratase and shikimate kinase are achieved. The organism is preferably also modified to limit the production of alternate end products from chorismate.

12 Claims, 3 Drawing Figures

OTHER PUBLICATIONS

Jacobs, N. J. et al, "Characterization of the Late Steps of Microbial Heme Synthesis: Conversion of Coproporphyrinogen to Protophyrin", *J. Bactiorolog.*, vol. 107:1, pp. 203–209, (1971).

Im, S. W. K. et al., "Phenylalanine Biosynthesis in *Escherichia Coli* K-12: Mutants Derpressed for Chorismate Mutase P-Prephenate Dehydratase", *J. Bactiorolog.*, vol. 106:3, 784–790, (1971).

Brown, K. D. et al, "Repression of Aromatic Amino Acid Biosynthesis in *Escherichia Coli* K-12", *J. Bacteriolog.*, vol. 108:1, pp. 386–399, (1971).

Im, S. W. K., et al., "Phenylalanine and Tyrosine Biosynthesis in *Escherichia coli* K-12: Mutants Depressed for 3-eoxy-D-Arabinopehtulosonic Acid 7-Phosphate Synthetase (phe), 3-Deoxy-D-Arabinoheptulosonic Acid 7-Phosphate Synthetase (tyr), Chorismate Mutase T-Prephenate Dehydrogenase and Transmitase A", *J. Bacteriolog.*, 108:1, 400–409, (1971).

Ely, B. et al, "Aromatic Amino Acid Biosynthesis: Regulation of Shikimate Kinase in *Escherichia coli* K-12", *J. Bacteriolog.*, 138:3, 933–943, (1949).

Bachman, B. J. et al, "Linkage Map of *Escherichia coli* K-12, Edition 6", *Microbiological Reviews*, vol. 44:1, pp. 1–56.

Kleckner, N. et al, "Genetic Engineering *In Vivo* Using Translocatable Drug-Resistance Elements", *J. Mol. Biol.*, vol. 116, pp. 125–159, (1977).

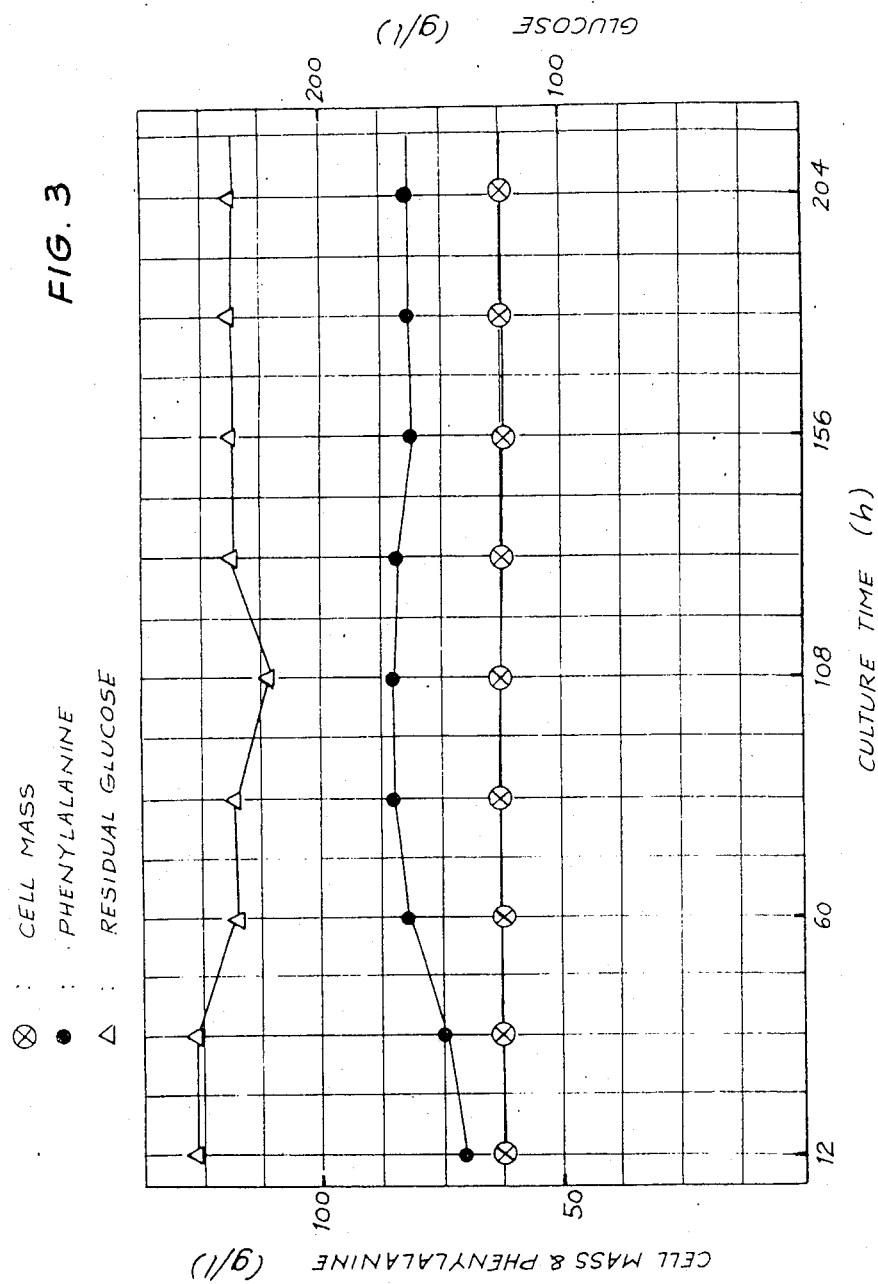

NOVEL MICROORGANISM AND METHOD

CROSS-REFERENCE TO RELATED APPLICATIONS

The present application is a continuation-in-part of U.S. application Ser. No. 284,801, filed July 20, 1981, now abandoned the entire contents of which are hereby incorporated by reference.

FIELD OF THE INVENTION

The present invention relates to a process for the production of phenylalanine and to novel strains of a species of microorganism capable, under appropriate culture conditions, of producing phenylalanine substantially faster than known strains of that microorganism.

BACKGROUND OF THE INVENTION

Phenylalanine is an amino acid having the formula $C_6H_5CH_2CH-(NH_2)CO_2H$ which is considered an essential amino acid in many animals but which can be synthesized by some microorganisms. *Escherichia coli* is a microorganism which it has been known for some time is capable of synthesizing phenylalanine.

In the wild type organism only enough phenylalanine is produced to satisfy the organisms own requirements. There is insufficient phenylalanine excreted by the wild type organism to be detectable by normal analytical techniques.

*Escherichia coli* produces phenylalanine using a biosynthetic pathway which starts with a suitable carbohydrate and converts that into intermediaries including erythrose 4-phosphate and phosphoenolpyruvate. These intermediaries are then converted to 3-deoxy-D-arabinoheptulosonate 7-phosphate (DAHP) by an enzyme known as DAHP synthase. The DAHP is in turn converted through a number of steps including the formation of shikimate, to chorismate. The chorismate is then converted through a terminal pathway to phenylalanine.

FIG. 1 attached hereto shows the three main factors affecting the overall conversion of erythrose 4-phosphate and phosphoenolpyruvate to phenylalanine. Firstly, several enzymes of the common pathway of aromatic biosynthesis leading to chorismate, and enzymes of the phenylalanine terminal pathway which branches from chorismate, are sensitive to repression (R) of enzyme synthesis. Secondly, both DAHP synthase isoenzymes at the start of the common pathway and chorismate mutase P-prephenate dehydratase (CMP-PDH) at the start of the phenylalanine pathway are sensitive to feedback inhibition (I). Thirdly, but less importantly, chorismate may be diverted down pathways other than the phenylalanine pathway.

SUMMARY OF THE INVENTION

The present invention consists in a mutant strain of *Escherichia coli* in which:

(i) the genetic constitution of the microorganism is such that at least one form of the enzyme 3-deoxy-D-arabino-heptulosonate 7-phosphate (DAHP) synthase is substantially free from inhibition by phenylalanine, tyrosine or tryptophan;

(ii) the genetic constitution of the microorganism is such that the enzyme complex chorismate mutase P-prephenate dehydratase is substantially free from inhibition by phenylalanine;

(iii)
(a) the control site pheAo is such that the formation of the enzyme chorismate mutase P-prephenate dehydratase (CMP-PDH) is substantially freed from repression by phenylalanine, or (b) the microorganism is otherwise modified such that the level of the enzyme chorismate mutase P-prephenate dehydratase in the microorganism is increased relative to that found in strains of the microorganism with wild type regulation of chorismate mutase P-prephenate dehydratase formation;

(iv)
(a) the genetic constitution of the microorganism is such that the formation of at least the form of the enzyme DAHP synthase freed from inhibition is substantially freed from repression, or (b) the microorganism is otherwise modified such that the level of the enzyme DAHP synthase in the microorganism is increased relative to that found in strains of the microorganism with wild type regulation of DAHP synthase formation; and (v)
(a) the genetic constitution of the microorganism is such that the formation of the enzyme shikimate kinase is substantially freed from repression, or (b) the microorganism is otherwise modified such that the level of the enzyme shikimate kinase in the microorganism is increased relative to that found in strains of the microorganism having wild type regulation of shikimate kinase formation.

Such a mutant strain is hereinafter called "a microorganism according to this invention".

The present invention further consists in a method for the production of phenylalanine comprising the steps of culturing microorganisms according to this invention in suitable media, and recovering the phenylalanine from the culture media and/or the cultured microorganism.

BRIEF DESCRIPTION OF THE DRAWINGS

The present invention will be better understood by reference to the accompanying drawings, in which:

FIG. 3 is a graph showing the kinetics of phenylalanine formation in continuous culture in accordance with the present invention.

FIG. 4 is a schematic diagram of a 1 liter culture vessel and its control equipment.

FIG. 5 is a schematic diagram of the 5 liter fermentor and its control equipment.

FIG. 6 is a standard curve for phenylalanine (bioassay procedure).

FIG. 7 is a chromatographic separation of aromatic amino acids:
(1) tyrosine (0.2 mg/ml)
(2) phenylalanine (0.4 mg/ml)
(3) tryptophan (0.1 mg/ml)
Injection volume: 20 μl
Attenuation: 0.02

Figure 1:
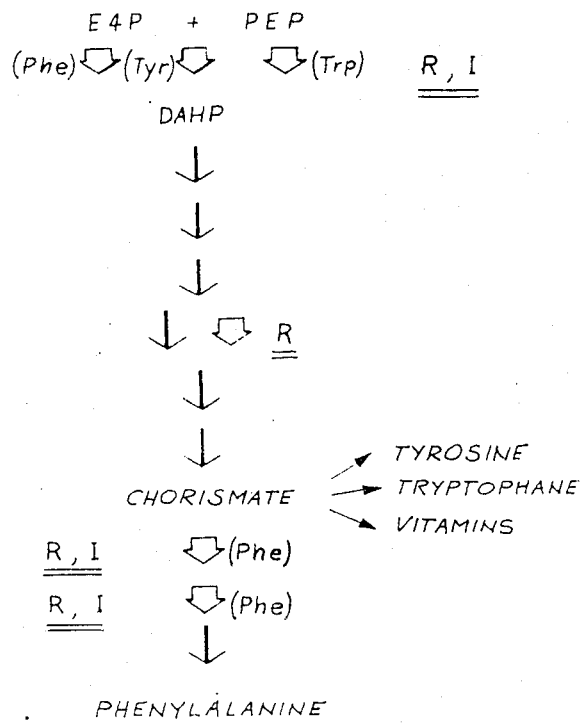
FIG. 1 is a diagram showing an outline of amino acid biosynthesis and its regulation in which R indicates repression of enzyme formation and I indicates inhibition of enzyme activity.

Other conditions were the same as described in the text.

FIG. 8 is a diagram showing the proposed isolation of transposon TnlO induced aroP mutant strain.

FIG. 9 shows the sensitivity to feedback inhibition of prephenate dehydratase.

Data are shown for the pheA101 pheO352 strain NST16 (●), the pheA+ pheO35 strain JP2250 (□), and the pheA+ pheO+ strain AT2273 (○).

FIG. 10 shows the relationship between degree of inhibition of chorismate mutase-p activity in cell extracts and phenylalanine concentration.

Data are shown for the pheA101 pheO352 strain NST16 (●), the pheA+ pheO352 strain JP2250 (□), and the pheA+ pheO+ strain AT2273 (○).

FIG. 11 shows the genetic linkage map of E. coli K-12 showing the loci relevant to this work.

Markers displaying cotransducibility that have a bearing on the present work have that linkage indicated by appropriate brackets. For further details refer to Bachmann et al. (1980).

FIG. 12 shows the principal strains that were made from strain JP2241.

Each filled in arrowhead represents the preparation of a new strain, each unfilled arrowhead the transfer of genes between strains. The gene transfer was brought about by either P1 Kc mediation transduction (TD) or conjugal transfer (C).

The genetic change to the recipient strain is indicated in brackets.

Only the strains in this series which are of direct interest with regard to phenylalanine overproduction are represented in this figure.

FIG. 13 is the kinetics of phenylalanaine production by strain NST37 in shaken flask culture.

Medium MMB was used, with 2 ug of thiamine per liter 21 mg of tryptophan per liter and 18 mg of tyrosine per liter.

Symbols used: □, phenylalanine; ●, cell mass; ○, residual glucose; ⊙ pH of the culture broth.

FIG. 14 shows the appearance of phenylalanine crossfeeding test plate after 20 hours of incubation at 37° C.

Strain W3110 is a wild-type control strain, NST9 is pheA (FBI$^r$), JP2250 is pheO352, NST21 is aroF (FBI$^r$).tyrR$^-$ pheA (FBI$^r$). pheO352 and NST26 is aroF (FBI$^r$).aroG (FBI$^r$) tyrR$^-$ pheA (FBI$^r$) pheO352.

The phenylalanine auxotrophic strain used in these tests was strain NST42.

FIG. 15 is the kinetics of phenylalanine production by the aroP: :Tn10 mutant and aroP+ strains in 1 liter fermentor cultures.

The cells were grown in medium MMT4-20 g/l glucose. The phosphate content of the medium was calculated to limit cell density at approximately 1 g/l dry weight of cells.

FIG. 16 is a diagram showing the characteristics of the strain NST37.

Large filled in arrows represent enzymes that are formed at derepressed levels; FBI$^r$ indicates feedback inhibition resistant enzymes.

FIG. 17 is a typical kinetics of phenylalanine production by strain NST37 in a 1 liter fermentor culture.

Medium MMT3 was used with 2 μg of thiamine per liter, 18.2 mg of tyrosine per liter and 9.19 mg of tryptophan per liter. The content of K$_2$HPO$_4$, the growth-limiting factor, was 110.4 mg per liter.

Symbols used: ○, cell mass; □, phenylalanine; ●, residual glucose. The mean value of q (phenylalanine) was taken up to the time interval indicated by the arrow.

FIG. 18 shows temperature profile for cell growth and phenylalanine formation.

Strain NST37 was cultured in a 1 liter fermentor in medium MMT3-20 g/l glucose. The phosphate content of the medium (108 mg of K$_2$HPO$_4$/l) was calculated to limit cell density at approximately 1 g dry weight of cells per liter.

Symbols used are as follows: ●, values at 29° C.; ○, values at 33° C.; ⊙, values at 37° C. and □, values at 41° C.

FIG. 19 shows a comparison of kinetic parameters obtained at different culture temperatures in a 1 liter fermentor, calculated from primary data given in FIG. 18.

Symbols used are as follows: ○, specific growth rates; ●, specific phenylalanine productivity and □, phenylalanine yield per mass of cells.

Specific growth rate and specific productivity were calculated from the values for the exponential phase of growth, and phenylalanine yield was obtained from the data at 30 hour cultures.

FIG. 20 shows the effect of phosphate concentrations on cell growth and phenylalanine yield in 1 liter fermentor cultures.

Strain NST37 was cultured in medium MMT3-20 g/l glucose supplemented with different concentrations of K$_2$HPO$_4$ at 37° C., and the pH of the culture broth was controlled at 6.5 with 2M NaOH solution.

The tyrosine content of the culture medium (15 mg/liter) was calculated to limit final cell density at approximately 1 g/l dry weight of cells.

Symbols used: ○, 0.66 m moles of final phosphate concentration; ●, 0.87 m moles; ⊙, 1.74 m moles.

FIG. 21 shows the effect of initial glucose concentration on biomass and phenylalanine production by strain NST37 in 1 liter fermentor cultures.

Strain NST37 was cultured at 33° C. in medium MMT3 supplemented with different concentrations of glucose; 4.5 g/l, 9.0 g/l 13.5 g/l and 18.0 g/l of glucose. The pH of the culture broth was controlled at 6.5 with 2M NaOH solution.

The phosphate concentration of the culture medium (161 mg/l of K$_2$HPO$_4$) was such as to limit the final cell density at approximately 1.5 g/l dry weight of cells.

Symbols used: ○, 0.45% glucose; ●, 0.9%, ⊙, 1.35% and □, 1.8%.

FIG. 22 shows the effect of initial glucose concentration on glucose uptake by strain NST37 in 1 liter fermentor cultures.

Conditions were described in footnotes to FIG. 21.

Symbols used: ○, 0.45%; ●, 0.9%; ⊙, 1.35% and □, 1.8% of initial glucose.

FIG. 23 shows the variation in DAHP synthase and prephenate dehydratase specific activities, and in output of phenylalanine during culture of strain NST37 in a 5 liter fermentor.

Cells were grown at 33° C. in medium MMT4-25 g/l glucose supplemented with 0.1 mg of thiamine per liter, 36.3 mg of tyrosine per liter and 22 mg of tryptophan per liter. The pH of the culture fluid was controlled at 6.5 by feeding 5M-NaOH solution.

The culture was carried out so that the final cell density was limited to approximately 1.5 g/l dry weight of cells by phosphate content of the medium (156 mg/l of K$_2$HPO$_4$).

Symbols used: ●, cell mass; ○ phenylalanine; ⊙, residual glucose; ⊙, specific activity of DAHP synthase and □, specific activity of prephenate dehydratase.

FIG. 24 shows the kinetics of phenylalanine production with strain NST70 during batch culture in a 1 liter fermentor.

Details of culture conditions are given in the text.

Symbols used: ◯, cell mass; ●, phenylalanine and ◌, residual glucose.

FIG. 25 shows the kinetics of phenylalanine formation with strain NST74 during batch culture in a 1 liter fermentor.

The cells were grown at 33° C. in medium MMT3-15 g/l glucose under phosphate-limiting conditions in a 1 liter fermentor. For the phosphate-limiting culture, the medium contained 99.8 mg of $K_2HPO_4$ per liter as a sole phosphate source. The pH was controlled at 6.5 by feeding 2M.NaOH solution.

Symbols used: ◯, cell mass; ●, phenylalanine, □, tyrosine and ◌, residual glucose.

FIG. 26 shows the kinetics of phenylalanine production with strain NST74 at higher cell densities in a 5 liter fermentor.

Cells were grown at 33° C. in medium MMT12-30 g/l glucose supplemented with 0.2 mg of thiamine per liter. Glucose supplements were made during the fermentor run; first supplement was carried out with 75 g of glucose at 11 hour culture time and second with 45 g at 17 hour time as indicated in the figure.

The phosphate content of the medium was calculated to have a growth supporting ability of approximately 12 g dry weight of cells per liter.

The pH of the culture broth was controlled at 7.0 by feeding an alkaline mixture; the mixed solution consisted of 450 ml of 5M NaOH, 250 ml of 5M KOH and 300 ml of 3.5M NHOH. This pH control has also served as a continuous supplementation of ammonium and potassium ions to the culture medium (total 180 ml of the alkaline mixture was added during the fermentation run). The dissolved oxygen tension in the fermentor was continuously monitored and was maintained at higher than 40% of air saturation by a constant aeration at a rate of 800 ml/min, and by varying the sparging rate of pure oxygen (around 0.1–0.3 liter of oxygen per min.).

Symbols used: ◯, cell mass; ●, phenylalanine; , residual glucose; □, tyrosine.

FIG. 27 shows the effect of dilution rate on cell mass, and phenylalanine and glucose levels with strain NST74 growing under a phosphate limitation in chemostat culture.

The cells were cultivated at 33° C. in medium MMT3-15 g/l glucose under phosphate-limiting conditions in a 1 liter fermentor. For the phosphate-limiting culture, the entering medium contained 99.8 mg of $K_2HPO_4$ per liter as a sole phosphate source.

The pH of the culture broth was regulated at 6.5 by feeding 2M.NaOH solution.

Symbols used; ◯, cell mass; ●, phenylalanine; ◯, residual glucose, and □, phosphate concentration.

FIG. 28 shows the effect of dilution rate on phenylalanine productivity, specific productivity, phenylalanine yield and biomass yield with strain NST74 in phosphate-limited chemostat culture.

The kinetic parameters shown in this figure were calculated from the data shown in FIG. 27.

Symbols used: □, phenylalanine productivity; ●, specific productivity ($q_p$); ◯, phenylalanine yield ($Y_p/s$), and ◯, biomass yield ($Yx/s$).

FIG. 29 shows the effect of specific growth rates on biomass yields and specific glucose uptake rates by strain NST74 and NST109 in phosphate-limited chemostat cultures.

The cells were cultivated at 33° C. in medium MMT3-15 g/l glucose under phosphate-limiting conditions in a 1 liter fermentor. For phosphate-limited chemostat culture, the entering media contained 99.8 mg of $K_2HPO_4$ per liter as a sole phosphate source. The pH was controlled at 6.5 with 2M NaOH solution.

Symbols used: ◯, values obtained with strain NST74 and ●, values with strain NST109.

FIG. 30 shows steady-state data and kinetic parameters for phenylalanine production by strain NST74 in phosphate-limited chemostat culture.

The cells were grown at 33° C. in medium MMT4-25 g/l glucose in a 1 liter fermentor. The pH of culture fluid was controlled at 6.5. For this chemostat culture, the concentration of phosphate in the entering medium was adjusted to 193.1 mg of $K_2HPO_4$ per liter as a sole phosphate source.

Symbols used ⊘, cell mass; ●, phenylalanine; , residual glucose and □, phosphate concentration.

FIG. 31 shows the effect of pH values on phenylalanine production by strain NST74 in phosphate-limited chemostat culture.

Strain NST74 was grown at 33° C. in medium MMT3-15 g/l glucose at the specific growth rate of 0.1 ($h^{-1}$) in a 1 liter fermentor. The phosphate, the growth-limiting nutrient, content of the entering medium was 99.8 mg per liter of $K_2HPO_4$. The pH of the culture fluid was controlled by feeding 2M.NaOH solution.

Symbols used; ●, cell mass; ◯, phenylalanine; □, yield coefficient per mass of cells, and ◯, residual glucose.

FIG. 32 shows a continuous culture profile at higher cell density with strain NST74 at specific growth rate of 0.05 $h^{-1}$.

Strain NST74 was cultured at 33° C. in medium MMT12-70 g/l glucose at the dilution rate of 0.05 $h^{-1}$ in a 5 liter fermentor. For phosphate-limited chemostat culture, the medium was supplemented with 0.6 g of $K_2HPO_4$ per liter as a sole source of phosphate.

The pH of the culture broth was regulated at 7.0 by feeding an alkaline mixture consisting of 450 ml of 5M.NaOH, 250 ml of 5M.KOH and 300 ml of 3.5M $NH_4OH$. These additions to the mixture to control pH also served as a continuous supplementation of ammonium and potassium ions to the culture medium. The average addition rate was 4.4 ml mixture per hour.

Dissolved oxygen tension in the fermentor was maintained at higher than 40% of air saturation by sparging a mixture of 800 ml/min of air and 250 ml/min of pure oxygen.

Symbols used: ◯, residual glucose; ●, phenylalanine; □, cell mass; ◯, inorganic phosphate.

FIG. 33 shows the relationship between phenylalanine resistant prephenate dehydratase activity and yield of phenylalanine obtained in shaken flask culture for a series of phenylalanine over-producing strains.

The data are taken from Table 3.11. Point A, values for the strain AT2273; point B, values for the strain NST9; point C, values for the strain JP2250 and point D, values for the strain NST16.

FIG. 34 shows the relationship between prephenate dehydratase specific activity and yield of phenylalanine obtained in shaken flask cultures.

Data are taken from Table 3.14. Point A, values for the pheA+ pheO+ strain NST45; point B, values for the pheA (FBI$^r$) pheO$^c$ strain NST37; point C, values for the pheA (FBI$^r$) pheO$^c$/pUNT20 strain NST64 and point D, values for the pheA (FBI$^r$) pheO$^c$/pUNT21 strain NST70.

DETAILED DESCRIPTION OF PREFERRED EMBODIMENTS

The present inventor has shown that substantially increased phenylalanine production occurs if the presence of high levels of feedback inhibition desensitized DAHP synthase is combined with removal of both repression and inhibition controls on at least the first step in the phenylalanine terminal pathways. It will be understood by persons skilled in the art that inhibition of an enzyme refers to the diminution of the activity of the enzyme while repression of the formation of an enzyme refers to a diminution in the rate at which the enzyme is synthesized by the microorganism.

The notation hereinafter used to designate structural genes, regulator genes and control sites of the single circular chromosone of *E. coli* is based on that disclosed by Bachmann and Low in Microbiology Reviews 1980.

The wild type *E. coli* produces DAHP synthase in at least three forms which are respectively subject to feedback inhibition by phenylalanine, tyrosine or tryptophan. It has been found that the genetic constitution of the microorganism can be altered such that at least one form of the enzyme i.e. one isoenzyme is produced which is not subject to feedback inhibition by one of the three abovementioned amino acids. It is preferred that feedback inhibition by both phenylalanine and tyrosine be removed, which can be achieved by mutation of their respective structural genes aroG and aroF to yield genes aroG(FBI ®) and aroF(FBI ®) respectively.

The formation of the various forms of DAHP synthase is subject to repression in the wild type as a result of the production by the microorganism of a regulatory protein which is a product of a control, or regulation gene tyrR. In the microorganism according to this invention this repression is overcome by a mutation of the control gene tyrR to remove the repression. It is obvious to those skilled in the art that the elevation of enzyme levels that is obtained by using tyrR mutants may be obtained readily by alternative approaches. One example is by the use of multi-copy plasmids having the appropriate structural genes for the production of the enzyme. If the latter method is used the repression would still exist but the enzyme levels can be raised to a satisfactory level by having a multiplicity of structural genes each of which is active in the formation of the desired enzyme.

The control gene tyrR controls production of two forms of DAHP synthase including DAHP synthase Phe, DAHP synthase Tyr. It is preferable that any mutation of control gene tyrR should have the effect of removing repression on these two forms of DAHP synthase. It is, however, within the scope of the present invention to provide in the microorganism a mutant form of tyrR which removes repression of the production of one of the forms of DAHP synthase such as the production of DAHP synthase Phe and to introduce into the microorganism multi-copy plasmids containing the structural genes for the production of the other forms of the enzyme, such as plasmids containing the gene aroF which encodes DAHP synthase Tyr.

Wild type *E. coli* produces the enzyme chorismate mutase P-prephenate dehydrate (CMP-PDH) which catalysts the first two steps in the terminal pathway producing phenylalanine from chorismate. This enzyme in the wild type microorganism is subject to inhibition by phenylalanine. The production of this enzyme is controlled by structural gene pheA and mutation of this gene to pheA(FBI ®) enables the organism to produce the enzyme in a form which is not subject to this feedback inhibition by phenylalanine.

The formation of CMP-PDH is subject to repression in the wild type *E. coli* due to the presence of control gene pheAo. This inhibition may be overcome as has been explained above by mutation of pheAo or by the use of multi-copy plasmids bearing pheAo pheA genes, an example of such a plasmid would be a derivative of the plasmid ColE 1.

The materials erythrose 4-phosphate and phosphoenolpyruvate and the intermediate shikimate are metabolites involved in the production of chorismate. A further intermediate in chorismate formation is shikimate-3-phosphate, which is formed from shikimate in a reaction catalysed by the enzyme shikimate kinase. The production of the enzyme shikimate kinase is subject to repression involving the product of the gene tyrR in the manner outlined above with respect to the repression of the formation of DAHP synthase Phe and DAHP synthase Tyr. This repression may be overcome either by a mutation to tyrR, with or without a simultaneous effect on the repression of one or more of DAHP synthase isoenzymes, or by the use of multi-copy plasmids.

In preferred embodiments of this invention, the microorganism according to this invention is further modified to block the metabolic pathways which lead from chorismate to end products other than phenylalanine. A mutation to the gene tyrA can block the production of tyrosine from chorismate while a mutation of trpE can block the production of tryptophan.

The microorganisms according to this invention may be constructed using standard genetic techniques and using pre-existent genetic material by techniques such as conjugation and transduction by bacteriophage. Localised mutagenesis facilitates the isolation of strains carrying the described mutations due to the availability of knowledge on the chromosomal location of the relevant genetic loci.

The culture of any given strain of a microorganism according to this invention can be optimized by routine testing of environmental factors such as temperature, pH, oxygen concentration and the like. The culture medium most preferably includes glucose as a carbon source though other substrates may be used. These other substrates include, but are not limited to, glycerol, xylose, maltose, lactose, lactates and acetic acid. The culture medium should also contain appropriate nutrient mineral salts and trace elements.

It is preferable that the organism is initially cultured for growth at a pH of from 5 to 8, most preferably 6 to 7, and at a temperature of from 25° to 42° C., most preferably 33° to 37° C. The fermenter is preferably stirred and aerated such that the dissolved oxygen tension does not drop below 20% saturation.

The method according to this invention may be carried out in a batch made or as continuous culture. In the latter case the dilution rate for the culture, that is the ratio of the flow rate to the reaction volume, is preferably between 0.01 hr$^{-1}$ and 0.5 hr$^{-1}$, most preferably between 0.05 hr$^{-1}$ and 0.15 hr$^{-1}$.

The culture medium should contain excess carbon and nitrogen to allow the organism to continue phenylalanine production. This could lead to uncontrolled biomass production unless steps are taken to prevent this. Excess biomass can be prevented by restricting the amount of certain of the organisms essential growth requirements in the culture medium. This is most conveniently done by controlling the amount of phosphate present in the culture medium. This is particularly important in permitting consistently high phenylalanine production in continuous culture.

Hereinafter described by way of examples only are preferred embodiments of this invention.

EXAMPLE 1

Strains of *E. coli* having the specific mutations in accordance with the present invention may be obtained in accordance with the processes and procedures described in detail in the doctoral thesis of YONG-JIN CHOI, entitled, "Phenylalanine Production by *Escherichia Coli:* A Feasibility Study," submitted May, 1981, and now present and cataloged in the Biomedical Library of the University of New South Wales, the entire contents of said thesis being hereby incorporated herein by reference.

Chapter 2-5 and bibliography of this thesis state:

MATERIALS AND METHODS

2.1 ORGANISMS

The strains used in this work are all derivatives of *Escherichia coli* K-12. Relevant genotypes of the strains are given in Table 2.1. A description of the plasmids and bacteriophages used is given in Table 2.2.

Stock cultures of bacteria were kept at 4° C. on Luria agar or minimal agar, and subcultured every two months. Reserve stocks of strains were kept as thick suspensions in Luria broth—375 g/l glycerol at −20° C., and also in the lyophilized state.

2.2 CHEMICALS

Unless specified, chemicals were obtained commercially and not further purified before use.

D-erythrose-4-phosphate dimethylacetal dicyclohexyl ammonium salt and phosphoenolpyruvate tricyclohexylammonium salt were obtained from Boehringer Mannheim GmbH, West Germany.

Free erythrose-3-phosphate was prepared by the method of Ballou et al (1955), and was adjusted to pH 5.0 with NaOH. Free phosphoenolpyruvate was prepared by removing the tricyclohexylammonium ion with activated Dowex 50, and then adjusted to pH 7.0 with NaOH.

Chorismic acid was prepared by the method of Gibson (1970). Barium prephenate was prepared by heating a solution of chorismic acid at pH 10.0 and 70° C. for 1 hour. The resulting sodium prephenate was purified on Dowex 1 resin in the same way as chorismic acid, and barium prephenate was precipitated from 80% (w/v) ethanol.

TABLE 2.1

LIST OF BACTERIAL STRAINS

| Strain | Relevant Genotype[a] | Source |
|---|---|---|
| W3110 | wild type | this laboratory |
| AB3259 | aroF363 aroH367 | A. J. Pittard |
| AT2273 | tyrA352 | K. D. Brown |
| JP2250 | aroF363 tyrA382 pheO352 | A. J. Pittard |
| JP2257 | JP2250 pheA363 | A. J. Pittard |
| JP2229 | aroF+ Δ[nadA-aroG-gal] 50 aroH367 tyrR366 tyrA4 pheA1:: Mu tna-2 thr-352 lacY5 his-4 | this laboratory |
| JP2235 | JP2229 aroF394 | this laboratory |
| JP2238 | JP2235 malT384 Δ[tonB-trp] | this laboratory |

TABLE 2.1-continued

LIST OF BACTERIAL STRAINS

| Strain | Relevant Genotype[a] | Source |
|---|---|---|
| JP2241 | JP2238 tonB+ trpE382 | this laboratory |
| JP2246 | aroG397 | this laboratory |
| AT2022 | pheA$_1$ :: Mu arg− his− pro− thi− | A. J. Pittard |
| JC411 | leu-6 argG metB-1 | A. J. Pittard |
| NST5 | AT2273 aroF363 tyrA+ pheA101 | this work |
| NST9 | JP2257 pheA101 pheO+ | this work |
| NST11 | JP2250 aroG103 | this work |
| NST12 | AT2273 aroF363 tyrA+ | this work |
| NST16 | JP2257 pheA101 | this work |
| NST17 | JP2257 pheA102 | this work |
| NST21 | JP2241 pheA101 pheO352 | this work |
| NST22 | NST21 trpE+ | this work |
| NST26 | NST21 nadA+ aroG397 gal+ | this work |
| NST29 | NST21 tyrA+ | this work |
| NST30 | NST29 trpE+ | this work |
| NST31 | JP2238 pheA101 pheO352 | this work |
| NST33 | NST26 leu+ | this work |
| NST34 | NST33 arg+ | this work |
| NST35 | NST34 pro+ | this work |
| NST36 | NST35 thr+ | this work |
| NST37 | NST36 his+ | this work |
| NST40 | AT2022 srl1300::Tn10 recA56 | this work |
| NST41 | NST37 srl1300::Tn10 recA56 | this work |
| NST42 | AT2022 str$^r$ | this work |
| NST43 | JP2235 pheA+ | this work |
| NST44 | NST43 nadA+ − aroG+ − gal+ | this work |
| NST45 | NST43 nadA+ − aroG397 − gal+ | this work |
| NST47 | JP2229 pheA+ | this work |
| NST49 | JC411 leu+ aroP::Tn10 | this work |
| NST50 | NST26 leu+ aroP::Tn10 | this work |
| NST51 | NST30 leu+ aroP::Tn10 | this work |
| NST54 | NST47 nadA+ − aroG397 − gal+ | this work |
| NST55 | NST22 nadA+ − aroG397 − gal+ | this work |
| NST56 | NST29 nadA+ − aroG397 − gal+ | this work |
| NST57 | NST30 nadA+ − aroG397 − gal+ | this work |
| NST58 | NST51 nadA+ − aroG397 − gal+ | this work |
| NST62 | KLF42/NST40 | this work |
| NST63 | KLF42 (pheA101 pheO352)/NST40 | this work |
| NST64 | KLF42 (pheA101 pheO352)/NST41 | this work |
| NST66 | NST42 (pUM307) | this work |
| NST67 | NST66 (F128) | this work |
| NST68 | NST17 (F128) (PUM307) | this work |
| NST70 | NST41 (pUNT 20) | this work |
| NST71 | NST37 zci-1005::Tn10[b] | this work |
| NST72 | NST37 zci-1005::Tn10 tyrR+ | this work |
| NST73 | NST37 trpE+ | this work |
| NST74 | NST73 tyrA+ | this work |
| NST75 | NST40 (pUM307) | this work |
| NST76 | NST40 (pUNT20) | this work |
| NST77 | NST37 aroB351 | this work |
| NST109 | aroH367 thi-1 | this laboratory |
| KLF4-2/KL253 | tyrA$_2$ recA$_1$ str$^r$ | A. J. Pittard |
| NK5304 | srl1300::Tn10 recA56 | A. J. Pittard |
| JP2690 | (pMU307) tyrR366 recA− nalA− | A. J. Pittard |
| JP2769 | ilv-1 his-29am zci-1005::Tn10 tvrR+ | A. J. Pittard |
| E5014(-F128) | Δ[proB − lac] thi− mal-24 | B. J. Wallace |

[a]Symbols designate various genes, as described by Bachmann et al. (1980). Unless otherwise specified, mutant alleles cause loss of ability to produce a functional protein. Further information about the phenotypic effects of some of these mutations may be found in Table 3. Some relevant gene-enzyme relationships are given in the introduction.
[b]Zci-1005::Tn10 indicates insertion of transposon Tn10 at a site of unknown function near tyrR (notation of Hong and Ames, 1971).

TABLE 2.2

PLASMIDS AND BACTERIOPHAGES USED IN THIS WORK

| Plasmid or phage | Relevant characteristics |
|---|---|
| F'142 | F'-pheO+ pheA+ tyrA+ |
| pUNT20 | F'-pheO$^{ca}$ pheA(FBI')[b] tyrA+ derived from the plasmid F'142 |
| F'128 | F'-proA proB lac |
| pUM307 | RSF2124 - pheA$^c$ |
| pUNT21 | RSF2124 - pheA(FBI') derived from the plasmid pUM307 |
| Pl Kc | Generalized transducing phage |

TABLE 2.2-continued
PLASMIDS AND BACTERIOPHAGES USED IN THIS WORK

| Plasmid or phage | Relevant characteristics |
|---|---|
| Pl Kc (recA⁻ propagated) | A derivative of Pl Kc which can grow on recA⁻ strains |
| ANK370 | Tn10 inserted λ phage |
| Mul | Randomly sited prophage location |

[a]pheO$^c$ indicates a constitutive mutation in the operator gene for pheA.
[b]pheA(FBI$^r$) indicates that the enzymes encoded by pheA gene are desensitized to end product inhibition.
[c]See So, M., Gill, R. and S. Falkow (1975).

The precipitate was collected, purified and assayed according to the method of Dayan and Sprinson (1970).

5-methyltryptophan (5-MT), p-fluorophenylalanine (p-FPA), β-thienylalanine (β-TA), streptomycin sulphate, chloramphenicol, lysozyme, 2(N-Morpholino) ethane sulfonic acid (MES), polyethylene glycol (PEG; mol. wt. 6,000), and sodium dodecyl sulphate (SDS) were obtained from Sigma, U.S.A.; L-3-fluorotyrosine (3-FT) was purchased from K and K Laboratories, U.S.A.; tetracycline HCl was obtained from Cyanamid Aust. Pty. Limited, Australia; ampicillin sodium was obtained from Beecham Research Laboratories, Australia, and N-methyl-N'-nitro-N-nitrosoguanidine (NTG) was purchased from Aldrich Chemical Co., U.S.A.

2.3 BUFFERS

The tris(hydroxymethyl)aminomethane (Tris)-HCl, sodium phosphate-potassium phosphate and citric acid-sodium citrate buffers used were prepared according to the methods of Dawson and Elliott (1969).

80 mM MES–100 mM NaCl buffer, one of a series of organic buffers devised by Good and his associates (1972) for use in biological work, was used in some experiments on culture medium.

The pH of the buffer was adjusted to 6.9 with NaOH.

Buffer 56 (Monod et al., 1951) consists of the following quantities of salts dissolved in 1 liter of distilled water.

| | |
|---|---|
| $K_2HPO_4$ | 10.6 g |
| $NaH_2PO_4.2H_2O$ | 6.1 g |
| $(NH_4)_2SO_4$ | 2.0 g |
| $MgSO_4.7H_2O$ | 2.0 ml of 100 g/l solution in distilled water |
| $Ca(NO_3)_2$ | 1.0 ml of 10 g/l solution in distilled water |
| $FeSO_4.7H_2O$ | 1.0 ml of 0.5 g/l solution in 1/100 M $H_2SO_4$ |

Buffer 56/2 is buffer 56 diluted in distilled water.
Dilution buffer.

Dilutions of cell suspensions from some experiments such as transduction and conjugation were made in buffer 56/2 containing 10% (v/v) nutrient broth.

2.4 MEDIA (i) Minimal Media

The minimal media used as selective media in genetic experiments and for growth of cells for cell extract preparation, consists of buffer 56 or buffer 56/2 with various separately sterilized supplements.

In liquid media the carbon source was 5 g/l glucose unless specified otherwise.

Solid minimal media were similar to liquid media except that a 56/2 base was used; carbon source concentration was 2 g/l, and 10 g/l Oxoid agar was added.

Medium MM.

Medium MM, an alternative liquid medium largely used for growing cells for enzyme assay, contains buffer 56, a carbon source and auxotrophic requirements according to Schedule I of Table 2.3.

Medium MMF.

This medium is formulated to contain a readily available form of iron in order to minimize enterochelin formation. It contains 200 μM $Fe^{+++}$ (as chloride) and 10 mM citrate adjusted to pH 7.0 with NaOH before addition of the medium.

Several media were specially developed for tryptophan and phenylalanine overproduction experiments (see also Tribe and Pittard, 1979). For these media auxotrophic requirements were supplemented using a different schedule: in shaken flask experiments schedule II of Table 2.3; in fermentor experiments schedule III was used. The media are as follows.

Medium MMB.

Medium MMB is medium MMF containing 1 ml/l of the trace element supplement described in Table 2.4, 20 g/l glucose and 100 mM $NH_4Cl$.

Medium MMD.

Medium MMD is a modified form of medium MM containing 10 g/l $CaCO_3$, which gives good control of pH in shaken flask experiments. The two phosphate salts of buffer 56 are reduced in concentration by a factor of two, and 200 μM $Fe^{+++}$ is added.

Media MMT3, MMT4 and MMT12.

These media were used in fermentor experiments. The formulation of these media is given in Table 2.4; it is based on a report giving yield coefficients for the various nutrients required for growth of enterobacteria (Neidhardt et al., 1974).

(ii) Luria broth and Luria agar

| Luria broth contains | |
|---|---|
| Oxoid tryptone | 10 g |
| Oxoid yeast extract powder | 5 g |
| NaCl | 10 g | in 1 liter of distilled water. The pH is adjusted to 7.0 with NaOH. Luria agar was prepared by the addition of 1.1% Oxoid agar to Luria broth.

(iii) Z broth and Z agar

Z broth was prepared by the addition of sterile $CaCl_2$ (2.5 mM final concentration) to sterile Luria broth. Z agar is Z broth plus 5 g/l Oxoid agar.

(iv) Nutrient broth and Nutrient agar

Nutrient broth contains 25 g Oxoid Nutrient broth No. 2 in 1 liter distilled water. The pH was adjusted to 7.2–7.4 with NaOH. Nutrient agar is nutrient broth plus 14 g/l Davis agar.

(v) Tetrazolium agar

This medium contains 25.5 g Difco Antibiotic agar and 2,3,5triphenyltetrazolium Cl in 1 liter distilled water. 1% carbon source was added aseptically.

(vi) H1 medium.

This medium contains

| | |
|---|---|
| $(NH_4)_2SO_4$ | 1.98 g |
| $MgSO_4$ | 0.25 g |
| $FeSO_4$ | 0.0005 g | in 1 liter of 0.1M potassium phosphate buffer (pH 7.0).

(vii) Lambda-yeast broth and Lambda-yeast agar

To 1 liter distilled water was added

| | |
|---|---|
| Oxoid tryptone | 10 g |
| NaCl | 2.5 g |

This media can be supplemented with 0.2% (w/v) maltose and 0.01% yeast extract.

Lambda-yeast agar was prepared by the addition of 10 g agar per liter Lambda-yeast broth.

TABLE 2.3

SCHEDULES FOR SUPPLEMENTATION OF MEDIA WITH GROWTH FACTORS

| Compound | Final concentration (mM) | | |
|---|---|---|---|
| | Schedule I | II | III |
| L-arginine HCl | 0.80 | 3.2 | 6.4 |
| L-histidine HCl | 0.50 | 2.0 | 4.0 |
| L-isoleucine | 0.32 | 1.28 | 2.56 |
| L-leucine | 0.32 | 1.28 | 2.56 |
| L-methionine | 0.17 | 0.68 | 1.36 |
| L-phenylalanine | 0.25 | 0.50 | 0.50 |
| nicotinic acid | 0.14 | 0.56 | 1.12 |
| L-proline | 0.15 | 0.60 | 1.20 |
| L-threonine | 0.35 | 0.70 | 0.70 |
| L-tryptophan | 0.10 | 0.20 | 0.20 |
| L-tyrosine | 0.25 | 0.50 | 0.50 |
| uracil | 0.83 | 3.32 | 6.64 |
| thiamine HCl | 0.0005 | 0.002 | 0.004 |
| shikimic acid | 0.005 | 0.02 | 0.04 |
| 4-aminobenzoic acid | 0.001 | 0.004 | 0.008 |
| 4-hydroxybenzoic acid | 0.001 | 0.004 | 0.008 |
| 2,3-dihydroxybenzoic acid | 0.001 | 0.004 | 0.008 |

TABLE 2.4

FORMULATION OF MEDIA FOR FERMENTOR EXPERIMENTS

| Constituent[a] | Final conc. (mM) required to yield 1 g dry weight/l[b] | Amount (ml per liter of medium)[c] | | |
|---|---|---|---|---|
| | | MMT3 | MMT4 | MMT12 |
| $K_2SO_4$ (0.105 M) | 0.183 | 5 | 6.6 | 20 |
| $MgCl_2$ (0.2 M) | 0.116 | 5 | 6.6 | 20 |
| $NH_4Cl$ (2.7 M) | 9.379 | 10 | 13.4 | 50 |
| Trace elements | — | 0.02 | 0.02 | 0.04 |
| Citrate buffer (1 M; pH 7.0) | — | 1 | 1 | 4 |
| Iron-citrate solution | — | 1 | 1 | 4 |
| $K_2HPO_4$ (0.264 M) | 0.869 | 10 | 13.4 | 50 |

[a]Constituents were added in the order listed, the volume made up to 1 liter with distilled water. Trace element stock solution contains 3 μM $(NH_4)_6(MoO_7)_{24}$, 400 μM $H_3BO_3$, 10 μM $CuSO_4$, 80 μM $MnCl_2$ and 10 μM $ZnSO_4$. Iron citrate solution consisted of $FeCl_3$, 10 mM and citrate buffer pH 7.0, 0.05 M.
[b]The yield coefficients were obtained from the data by Neidhardt et al. (1974).
[c]Medium MMT3, MMT4 and MMT12 have the growth-supporting capacities of 3 g, 4 g and 12 g dry weight cell mass per liter of culture fluid respectively.

(viii) Lambda-Top medium.
This medium contains

| | |
|---|---|
| Tryptone | 10 g |
| NaCl | 2.5 g |
| Oxoid agar | 6.5 g | in 1 liter of distilled water.
(ix) SM medium.
SM medium contains 5.48 g of NaCl and 2.47 g of $MgSO_4$ in 1 liter of 0.02M Tris-HCl buffer (pH 7.5).
(x) Soft-agar Overlays
This consists of 3 ml of buffer 56/2 containing 5 mg/ml Oxoid agar.

2.5 PREPARATION OF BACTERIOPHAGE LYSATES (i) Preparation of P1 Kc lysates.

Phage P1 Kc lysates were produced according to the method described by Caro and Berg (1969).

$10^8$ pfu of P1 Kc lysate was added to 2 ml of overnight culture of the host strain grown in Z broth. 0.1 ml samples of this mixture were then added, using 3 ml molten soft agars, to Z agar plates. After 6 hours incubation at 37° C., 2 ml of Z broth was added to each plate, and the incubation was continued for another 2 hours. The Z broth and soft agar layers were gently removed and emulsified.

This mixture was centrifuged in a bench centrifuge for 20 minutes, then carefully decanted. Chloroform (approximately 0.5 ml/15 ml lysate) was added to the lysate and the mixture gently shaken. After setting at 4° C. overnight, the lysate was centrifuged again and decanted into a sterile tube to remove debris and chloroform. Several drops of chloroform were added again to the clarified lysate. This procedure produced a sterile lysate with a titre of $5 \times 10^9$ to $3 \times 10^{10}$ pfu per ml.

(ii) Preparation of λNK370 phage stocks.

For each stock 0.15 ml overnight culture of NK 5336 in lambda broth plus 0.5 ml lambda broth plus 1–5 lambda plaques (one plaque if large; five plaques if the plaques were small) were mixed. Plaques of no greater than 12 hours of age were chosen (preferably less than 12 hours of age). After 20 minutes standing at room temperature for phage adsorption, 7.5 ml of freshly melted lambda top was added.

The mixture was distributed to 3 very fresh (24 hours old or less) lambda plates, and incubated at 37° C. until plates became lacy and then clear. All of the top agar was then collected into a centrifuge tube containing 2 ml of SM medium and 0.2 ml $CHCl_3$, vortexed, centrifuged in a bench centrifuge for 10 minutes and the supernatant collected and titered.

Good plate stocks should be $1-3 \times 10^{10}$ pfu/ml.

(iii) Preparation of W3110 : : Tn10 pool.

General procedures for making Tn10 "hops" in E. coli were described by Kleckner et al. (1977).

The recipient strain W3110 was grown overnight in lambda-yeast broth and then concentrated 20-fold in the fresh broth. The vehicle phage λNK370, aerated to remove chloroform vapour, was added at multiplicity of infection of 0.2. The mixture was incubated for 45 minutes at 37° C. without shaking to allow for phage adsorption.

0.1 ml aliquots of the bacterial mixture were then plated on lambda-yeast plates, containing 20 μg tetracycline per ml of media and 2.5 mM sodium pyrophosphate. The plates were incubated at 37° C. The colonies on these selection plates contained Tn10 from λNK370 inserted at random sites on the chromosome.

These clones (500 to 1,000 clones) were mixed together and a generalized transducing phage P1 Kc lysate was grown on this mixed pool.

2.6 ISOLATION OF BACTERIAL PLASMID DEOXYNUCLEIC ACID (DNA)

This procedure was used to make a cleared lysate of a recombinant ColE1 plasmid (pMU307) which was employed as a source of deoxynucleic acid (DNA) to transform $CaCl_2$ treated E. coli strains, and was based on the method described by Guerry et al. (1973).

One volume of the unwashed overnight culture of strain JP2690 (pMU307+) cultured in medium MM was resuspended in 20 volumes of fresh medium MM containing 1% (w/v) casein hydrolysate.

After the culture was grown to mid or late exponential phase, chloramphenicol (170 μg/ml) was added. The cells were incubated a further 16 hours at 37° C. with shaking to allow for relaxed replication of the plasmid (Clewell, 1972), and then harvested, washed twice in Tris-HCl buffer (0.05M; pH 8.3), and resuspended at a concentration of $10^{11}$ cells per ml in 25% (w/v) sucrose in 0.05M Tris-HCl buffer (pH 8.3) containing $2 \times 10^{-5}$M n-dodecylamine HCl.

After addition of 0.5×ml of 0.25M Na2EDTA, the suspension was mixed gently and placed at 4° C. for 5 minutes. 0.2×ml of lysozyme (5 to 10 mg/ml in 0.25M Tris-HCl buffer, pH 8.3) was added and the cell mixture was mixed gently.

After an additional 15 min. incubation at 2° to 4° C., 1.7×ml of sodium dodecyl sulphate (2% (w/v) in 0.05M Tris-HCl buffer, pH 8.3 containing 0.07M EDTA and $2 \times 10^{-5}$M n-dodecylamine HCl) was added with gentle mixing.

After complete cellular lysis (in less than 30 min.), 0.9×ml of 5M NaCl and 0.1×ml of 10% (w/v) sodium dodecyl sulphate solution (i.e. to give 1% (w/v) sodium dodecyl sulphate and 1M NaCl overall) were added and the viscous solution was mixed gently but thoroughly.

The lysate was stored at 4° C. overnight, after which it was centrifuged at 17,000 g for 30 to 60 min. at 4° C.

The supernatant was collected by decantation, brought to 10% (w/v) of polyethylene glycol (Mol. wt. 6,000) by mixing in appropriate volume of 40% (w/v) solution in 0.05M Tris-HCl buffer (pH 8.3), and then stored overnight again at 2° to 4° C. The polyethylene glycol/DNA solution was centrifuged at 700 g for 5 min. at 2° to 4° C.

After discarding the supernatant the fluffy white precipitate was resuspended in minimum volume of 0.1M Tris-HCl buffer, pH 8.3 (plasmid DNA from 1 liter of culture should resuspend in less than 3 ml of the buffer).

This suspension was used immediately as a DNA preparation for transformation experiments.

2.7 TRANSDUCTION

The recipient strain was grown overnight in Z broth. The culture was concentrated ten-fold and 0.2 ml of this cell suspension was mixed with $10^9$ pfu of bacteriophage P1 Kc lysate in a final volume of 5 ml of Z broth.

This procedure resulted in a phage to cell ratio of approximately 1:4. The transduction mixture and a reversion control containing cells of the recipient but no phage were incubated at 37° C. for 20 min without shaking to allow phage adsorption.

The suspensions were then centrifuged and the cells washed three times in sterile citrate buffer (0.1M, pH 5.5). The cells were resuspended in 1 ml of this buffer and 10-fold and 100-fold dilutions were prepared with the citrate buffer. 0.1 ml samples of the diluted transduced cells were plated onto selective medium.

Reversion control cells washed as described above were plated undiluted onto the same selective medium.

Phage lysates were stored over chloroform at 4° C., and checked for sterility prior to every transduction.

2.8 CONJUGATION

Matings were largely carried out for the transfer of conjugative plasmids in the construction of new strains.

The donor strain carrying the plasmid was grown in medium MM or Luria broth, the recipient strain in Luria broth, both to early exponential phase (approximately 30 mg/l of cells). The donor and recipient strains were mixed together in a 150 ml erlenmeyer flask in the ratio of one donor to 9 recipient cells. After swirling the mixture gently for several minutes to allow for the formation of mating pairs, the culture was incubated at 37° C. for 30 minutes without agitation. A sample was then removed and vortexed vigorously to disrupt mating pairs.

An aliquot (0.1 ml) of both undiluted and suitably diluted mating mixture was then plated on selective medium. Separate samples of both parents were also plated on the same medium to check for reversion.

2.9 TRANSFORMATION

Transformation was used to transfer the ColE1 plasmid into certain recipient strains; pMU307 to an appropriate recipient strain. The procedure used for transformation was a slight modification of that of Cohen et al. (1972).

A recipient strain was grown at 37° C. in H1 medium to an optical density of 0.6 at 590 nm.

At this point the cells were chilled quickly, sedimented and washed once in 0.5 volume 10 nM NaCl. After centrifugation with a bench centrifuge, cells were resuspended in half the original volume of chilled 0.03M $CaCl_2$, kept at 0° C. for 20 min, sedimented, and then resuspended in 0.1 the original volume of 0.03M $CaCl_2$ solution.

Chilled DNA samples in 0.1M Tris-HCl buffer (pH 8.3; containing 0.01M EDTA) were supplemented with 0.1M CaCl to a final concentration of 0.03M.

0.2 ml of competent cells treated with $CaCl_2$ were added to 0.1 ml of DNA solution with chilled pipettes, and an additional incubation was done for 90 min at 0° C. Bacteria were then subjected to a heat pulse at 42° C. for 2 min, chilled, and then diluted 20-fold into antibiotic-free Luria broth.

After incubation at 37° C. for 60 min, cells were plated on minimal media containing 25 μg/ml sodium ampicillin.

2.10 GENE CONVERSION

The process of gene conversion was used as a means of transferring mutations from bacterial chromosome to a plasmid.

A brief outline of this procedure is shown in the following diagram.

(i) Donor chromosome KL253/plasmid KLF42
pheA+ pheO+ tyrA− recA−/pheA+ pheO+ tyrA+
Recipient (NST16)
pheA (FBI$^r$) pheO$^c$ tyrA−

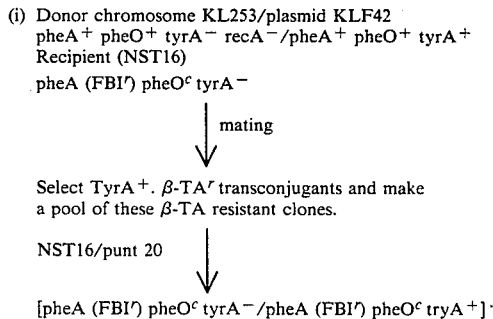

Select TyrA+. β-TA$^r$ transconjugants and make a pool of these β-TA resistant clones.

NST16/punt 20

[pheA (FBI$^r$) pheO$^c$ tyrA−/pheA (FBI$^r$) pheO$^c$ tryA+]·

-continued (ii) Donor (NST16/punt 20)
pheA (FBI$^r$) pheO$^c$ tyrA$^-$/pheA (FBI$^r$) pheO$^c$ tyrA$^+$
Recipient (NST40)
pheA$^-$ pheO$^+$ tyrA$^+$ sr1::Tn10 recA$^-$

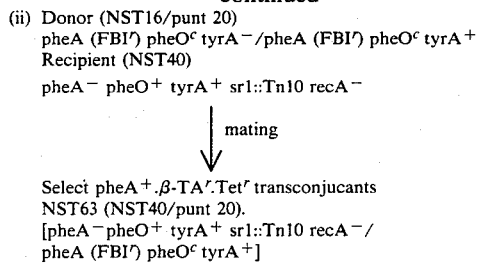

Select pheA$^+$.β-TA$^r$.Tet$^r$ transconjucants
NST63 (NST40/punt 20).
[pheA$^-$pheO$^+$ tyrA$^+$ sr1::Tn10 recA$^-$/
pheA (FBI$^r$) pheO$^c$ tyrA$^+$]

At first stage (see the diagram) matings were carried out with the strain KLF42/KL253 as a donor and the strain NST16 as a recipient.

The transconjugants into which the plasmid KL253 had been transferred were recovered from medium MM lacking tyrosine but containing $1 \times 10^{-3}$M β-thienylalanine.

Since this selective medium favours growth of pheA(FBI$^r$),pheO$^c$/pheA(FBI$^r$)pheO$^c$ homogenotes in preference pheA(FBI$^r$)pheO$^c$/pheA$^+$pheO$^+$ heterogenotes, most of TyrA$^+$. β-TA$^r$ transconjugants on this medium are considered to arise as a result of gene conversion events rather than that of being due to spontaneous mutation in the recipient, which would be expected to occur at much lower frequency.

At stage two, in order to identify the plasmid gene converted to pheA(FBI$^r$)pheO$^c$ a mating was done using the cells of the β-TA$^r$ transconjugants as a donor and the pheA$^-$.recA$^-$.Tet$^r$ strain NST40 as a recipient.

This was achieved by suspending the cells from the β-thienylalanine containing medium in Luria broth and mating with the recipient strain, and then plating on medium MM lacking phenylalanine and supplemented with $1 \times 10^{-3}$M β-thienylalanine and 10 μg/ml tetracycline for selecting transconjugants carrying the gene-converted plasmid.

This same method was used also to isolate the plasmid pUNT21 from the ColE1-pheA plasmid pMU307 (refer to Section 3.1.3).

2.11 ISOLATION OF MUTANTS AND RECOMBINANTS (i) Mutagenesis by N-methyl-N'-nitro-N-nitrosoguanidine (NTG).

The conditions under which the cells were treated with NTG were not those suggested by Adelberg et al. (1965).

Logarithmic phase cells from Luria broth were centrifuged, washed once in 0.1M citrate buffer (pH 6.0), resuspended in the same buffer (1 to $5 \times 10^9$ cells/ml), and then treated with NTG 300 μg/ml for 15 min.

After incubation a 1.0 ml sample was filtered on a cellulose acetate filter (pore size 0.2μ) and washed using cold 56/2 buffer.

The membrane filter was dropped into 5 ml of fresh Luria broth, and the cells were permitted to undergo two division cycles. The cells were then centrifuged and washed twice in sterile 56/2 buffer.

(ii) 3-Fluorotyrosine resistant mutants

Mutants resistant to 3-fluorotyrosine (FT) were isolated by plating on medium MM containing $5 \times 10^{-4}$M 3-fluorotyrosine and incubating for 2 days at 37° C. The actual experiments were rather complicated, involving localized mutagenesis, and are described in detail in results section 3.1.1.

(iii) β-Thienylalanine resistant mutants

The isolation procedure used was very similar to that for obtaining 3-FT resistant mutants and for details refer to results section 3.1.1. Minimal agar containing $1 \times 10^{-3}$M β-thienylalanine was used as the selection medium.

(iv) Isolation of Antibiotic Resistant Mutants

In order to isolate mutants which have spontaneously acquired resistance to streptomycin, 100 ml of an overnight-grown Luria broth culture was supplemented with 200 μg/ml streptomycin.

After incubation for a further 24 hours, the culture was plated on nutrient agar containing 200 μg/ml streptomycin. Colonies arising on these plates were purified before being used for further work.

(v) Isolation of recA Recombinants

The recA$^-$ allele destroys a cell's capacity for recombination and was, therefore, introduced into strains to stabilize plasmids carrying genetic material homologous to the chromosome.

The construction of a recA$^-$ derivative was achieved by using the sr11300::Tn10 recA56 strain NK5304 as the donor of recA$^-$ allele in transduction. A specially derived mutant of P1 Kc transducing phage which can grow on recA$^-$ strains was propagated on NK5304 using the usual plate method of preparing P1 Kc lysates. The resulting lysate was used to transduce recA$^+$ recipient strains, selecting for tetracycline resistant colonies on Luria agar containing 10 μg/ml tetracycline. The Tet$^r$ transductants were purified by streaking on the same selective medium, and tested for their sensitivity to ultraviolet irradiation as described in the following section.

Approximately 60% of the tetracycline resistant recombinants tested were found to have acquired increased sensitivity to ultraviolet irradiation, and hence the donor's recA mutation.

2.12 SCREENING AND CHARACTERIZATION OF NEW STRAINS (i) Patch-plating

Recombinant colonies for transduction experiments were scored for unselected markers using the patch-plating technique (Lederberg and Lederberg, 1952).

Master plates were prepared by subculturing transductants onto selection plates, in the form of small patches, aided by a template divided into a number of squares. These master plates were incubated overnight at 37° C. and then patch plated to different media, using sterile toothpicks to transfer the inocula. This technique was used for scoring nutritional markers, and resistance to growth inhibition by tetracycline, 3-fluorotyrosine, 5-methyltryptophan and β-thienylalanine.

(ii) Streaking of Bacterial Cultures

To confirm bacterial phenotypes when the response on patch plates was unclear, or for newly constructed strains of significance, purified colonies were emulsified to sterile buffer 56/2, and streaked onto different media to give single colonies. Up to eight isolates could be tested per plate, including the appropriate controls.

(iii) Cross-feeding (syntrophism)

A modified cross-feeding test (Tribe, 1976) was found to be particularly useful in screening for mutant strains that had inherited mutations affecting phenylalanine production. Approximately 50 μg of cells of a phenylalanine auxotroph, generally Strain NST42, was added to 1 liter of molten medium MMB-agar at 56° C.; these plates were immediately poured and allowed to dry.

Light suspensions in buffers 56/2 of strains to be tested were then spotted onto the plates using a flamed loop. The plates were examined for growth of the indicator strain around each surface spot of growth after 18 to 48 hours of incubation.

(iv) Tests for Recombination Deficiency

Cells carrying mutations in the recA gene are unable to carry out genetic recombination and are also highly sensitive to ultraviolet light. The following method for testing recA− makes use of the increased sensitivity to ultraviolet light.

About 12 colonies of the strains to be tested were patched onto nutrient agar using sterile toothpicks, including at least one patch of a known recA wild type control. After overnight growth at 37° C., the organisms on each plate were replica plated using a sterile velvet onto four nutrient agar plates in succession. The fourth plate was kept as the non-irradiated control. The other plates were subjected to ultraviolet irradiation for 60 sec. at a distance of 45 cm from the ultraviolet element using a General Electric 15 W germicidal lamp.

The plates were then incubated overnight in the dark at 37° C. and examined for growth. RecA− strains displayed distinctly increased sensitivity to ultraviolet light in this test.

2.13 MEASUREMENT OF ENZYME SPECIFIC ACTIVITIES IN CELL EXTRACTS (i) Growth of cells for assay of enzyme activity For each cell extract prepared, a 200 ml liquid medium MM culture was grown in a rotary shaker at 37° C. using as an inoculum, 5% by volume of an overnight culture in the same liquid medium. After the cells had undergone at least four mass doublings, growth was terminated in midexponential phase by transfer of flasks into an ice-bath.

(ii) Preparation of cell extracts

After being harvested by centrifugation, 7,000 rpm, 10 minutes at 4° C., cells were washed twice in ice-cold 0.9% (w/v) NaCl and suspended in 5 ml of appropriate buffers. The buffers were 0.1M sodium phosphate, pH 7.0, containing 100 μm EDTA in the case of extracts prepared for assay of DAHP synthase, 0.05M Tris-HCl, pH 7.8, containing $10^{-4}$M EDTA and $5 \times 10^{-3}$M dithiothreitol for chorismate mutase assay, and 0.025M Tris-HCl buffer, pH 8,2, containing $10^{-4}$M EDTA and $5 \times 10^{-3}$M dithiothreitol for assay of prephenate dehydratase.

Cell breakage was then achieved using a Branson B-15 sonicator (Branson Sonic Power, Co., U.S.A.), at an output setting of 3 millivolts, large tip, for a total of 2 to 4 minutes. Between bursts of 30 seconds, the cell suspensions were chilled in an ice-bath for 60 to 90 seconds to minimize enzyme denaturation from overheating. Extracts were clarified by centrifugation at 20,000 g for 10 minutes, then assayed immediately.

(iii) Protein estimation

Protein estimation of the cell extracts was carried out colorimetrically using the method of Lowry et al. (1951) with bovine serum albumin as a standard.

(iv) United of enzyme activity

Enzyme assays were all carried out at 37° C. under conditions of linearity with respect to incubation time and amount of enzyme used.

The unit of activity is the amount of enzyme converting 1 μmole of product per minute at 37° C.

Specific activities are given as milliunits (mU) of enzyme activity per mg of protein.

(v) DAHP synthase assay. (EC 4.1.2.15)

DAHP synthase activity was determined by measuring the amount of DAHP formed from erythrose-4-phosphate and phosphoenol-pyruvate (Camakaris, 1975; Srinivasan and Sprinsion, 1959).

The incubation mixture contained 0.58 μmole erythrose-4-phosphate, 0.5 μmole phosphoenolpyruvate, and a rate limiting amount of enzyme, in a total volume of 0.5 ml.

Camakaris' method of diluting the cell-extract was used: the diluent was 0.1M phosphate buffer, pH 7.0, containing 1 mM $COCl_2$, and 8 mg/ml bovine serum albumin; 8 mg/ml bovine serum albumin was also added to the buffer included in the incubation mixture (0.3 ml of 0.1M phosphate buffer, pH 6.4).

After a 10 min incubation at 37° C. the reaction was stopped by the addition of 0.2 ml of 100 g/l trichloroacetic acid. The mixture was centrifuged and 0.4 ml of supernatant was removed for the estimation of DAHP.

DAHP was estimated according to the method of Doy and Brown (1965). To 0.4 ml of the supernatant fluid, 0.25 ml of sodium periodate (0.025M in 0.15M $H_2SO_4$) was added. After incubation at 37° C. for 30 min 0.5 ml of 20 g/l sodium arsenite in 0.5M HCl was added. After 2 min, 2 ml of 3 g/l thiobarbituric acid was added and the tubes were placed in a boiling water bath for 8 min.

The tubes were kept at 56° C. while measurements of optical densities were made. The optical densities at 549 nm and 625 nm were measured in a spectrophotometer, the former wavelength corresponding to the absorption maximum of the chromophore, and the latter being a turbidity correction suggested by Doy and Brown.

The concentration of DAHP and hence the specific activity was calculated using the molar extinction coefficient of 33,400.

(vi) Chorismate mutase (E.C.5.4.99.5) assay

This method depends on the enzymatic conversion of chorismate to prephenate (Cotton and Gibson, 1965) followed by the chemical conversion to phenylpyruvate by acidification, and formation of this latter compound being measured by its absorbance at 320 nm in alkali (Gibson, 1964). The reaction mixture contained 0.4 μmoles of barium chorismate, 0.02 μmoles of EDTA, 1 μmole of dithiothreitol, 20 μmoles of Tris-HCl buffer, pH 7.8 and an appropriate amount of cell extract, in a total volume of 0.4 ml.

After incubation at 37° C. for 10 min, 0.4 ml of 1M HCl was added. Another 10 min incubation was done, and 3.2 ml of 1M NaOH was then added. The absorbance at 320 nm was measured as soon as possible. The concentration of phenylpyruvate produced was calculated using a molar extinction coefficient of 17,500, after correcting the optical density by comparison with a control in which the enzyme was added after the HCl addition.

(vii) Prephenate dehydratase (E.C. 4.2.1.51.) assay

The phenylpyruvate which was formed from prephenate was measured by its absorbance at 320 nm in alkali (Gibson, 1964) as for the chorismate mutase assay. Each ml of reaction mixture contained 0.5 μmoles barium prephenate, 25 μmoles Tris-HCl buffer, pH 8.2, 0.05 μmoles EDTA, 2.5 μmole dithiothreitol and an appropriate amount of enzyme.

After a 10 min incubation at 37° C. the phenylpyruvate in a 1 ml volume was assayed by adding 3 ml of 1M NaOH and measuring the absorbance at 320 nm immediately. The concentration of phenylpyruvate was calculated using a molar extinction coefficient of 17,500. A zero time tube was routinely included.

2.14 GROWTH OF CELLS FOR DETERMINATION OF PHENYLALANINE PRODUCTIVITY

Unless specified otherwise, the culture temperature was 37° C. in flask experiments and 33° C. in fermentor experiments.

Inocula consisted of 0.03–0.05 g dry weight cell (per liter of test medium) from an unwashed overnight-grown MMB culture.

(1) Measurement of cell mass

A standard curve was available relating turbidity measurements at 670 nm with Spectronic 20 colorimeter (Bausch and Lomb) to the dry cell mass. This dry mass was obtained by taking a sample of cells, washing twice in distilled water and drying at 100° to 110° C. for 24 hours.

In using this curve, samples were first appropriately diluted in buffer 56/2 to ensure that cell densities were within the range of the curve.

(ii) Shaken flask experiments

These were typically carried out by using 100 ml of medium in a 500 ml conical flask. A lightly packed cotton wool stopper was used, and the flask was shaken at approximately 200 cycles per min in an orbital shaker.

Unless specified otherwise, fermentation data from the flask experiments were the average of 2–3 flasks. Duplicates were generally in agreement within 5%.

(iii) 1 liter fermentor experiments

Culture vessel and control equipment.

A one liter wide-necked glass reaction vessel (Quickfit), England) fitted with a flat flange lid was used as a culture vessel for most of the batch and continuous culture experiments.

The vessel was modified to allow the introduction of an overflow side arm, a sampling loop at the base, a standard socket (Quick-fit) for a pH probe in the side, and a pocket to hold a thermistor.

The lid was designed to accommodate an agitator shaft through a rubber gland in a ground glass joint, as well as sockets (Quick-fit) for an oxygen probe, a cold finger, a gas outlet, a medium inlet and an acid/alkaline inlet.

This culture vessel was installed with a pH control unit, a temperature control unit, an agitator, a gas supply unit and a medium supply unit. The overall schematic diagram is shown in FIG. [4] [Table 3 describes the items represented by the references numbers.]

A pH meter-controller (Dynaco, Epsom, Surrey, England) was used for maintaining a constant pH of culture broth with association of a steam sterilizable combination pH probe ("Probion", England) and a peristaltic pump ("Delta", Watson-Marlow Ltd., England) which pumped 2N sodium hydroxide or 2M hydrochloric acid.

A glass cold finger was immersed into the culture broth for cooling using circulating cold water inside the finger. The temperature of the culture broth was controlled using a thermistor sensor and an "Ether" relay operating a 250 W "Osram" infra-red reflector lamp for heating.

The supply of air was regulated by a monostat and a rotameter. After passing through a sterile filter unit (Gamma 12, Whatmann), the gas was let into the hollow shaft of the agitator and fed into the culture fluid through the base of the agitator plate. The gas escaped from the vessel through a condensor connected with a miniature line filter (Microflow Pathfinder Ltd., England) to prevent back-contamination. Dissolved oxygen tension was monitored by a Teflon-covered silver-lead electrode (Johnson et al., 1964), and was kept between 40 and 80% of saturation during experiments. Agitation of the culture broth was achieved by means of a Vibromix agitator ("ChemaP", Switzerland) and the intensity of agitation was regulated by a variable transformer.

The medium was fed into the fermentor by a peristaltic pump ("Wab", England) coupled with a variable speed "zeromax" gearbox (Model JK-1, U.S.A.).

A glass trap was installed on the medium supply line to prevent back-contamination.

[TABLE 3]

| | |
|---|---|
| 1. | Culture vessel |
| 2. | Vibromix |
| 3. | Variable transformer |
| 4. | Heating lamp |
| 5. | Relay |
| 6. | Thermistor |
| 7. | pH probe |
| 8. | pH controller and meter |
| 9. | Oxygen probe |
| 10. | DOT meter |
| 11. | Acid or Alkaline reservoir |
| 12. | Peristaltic pump |
| 13. | Condenser |
| 14. | Cold finger |
| 15. | Cooling water |
| 16. | Medium pump |
| 17. | Monostat |
| 18. | Flow meter |
| 19. | Air filter |
| 20. | Sampling loop |

The culture broth in the vessel passed by overflow through an outlet sidearm followed by a glass U-shape trap and a straight glass trap to prevent back-contamination.

(iv) 5 liter fermentor experiments

The fermentation system was of the conventional thermostatted, agitated, air-sparged tank reactor type with 3 to 4 liter working volume. A schematic diagram of the vessel and control equipment is shown in FIG. [5] [and the parts thereof are itemized in Table 4].

Culture vessel and control equipment

A standard 29 cm long and 17 cm diameter QVF glass cylinder was closed at top and bottom by round stainless steel plates. Rubber gaskets were used to seal the end plates to the glass body. The bottom plate was fitted with an overflow pipe, a gas inlet line, a thermister for temperature control, a cooling finger and a sampling port. The top plate was fitted with ports for the addition of fresh medium, acid, alkaline and antifoam. A thermometer and foam sensors were also accommodated on the top plate.

In continuous culture operation the overflow tube was connected to a culture reservoir, a 20 liter pyrex glass jar.

The inlet gas was sterilized by filtration with sterile Whatman filter unit (Gamma 12). The gas supply was regulated by a pressure regulator and passed through a rotameter to measure gas flow rates. For agitation a six-bladed flat turbine impeller was used. The impeller is positioned 4 cm from the bottom, and rotated about 600 rpm by a "print motor" (type 16AAB, Yaskawa Electric, Japan) connected to a "Minipa" speed controller.

[TABLE 4]

| | |
|---|---|
| [101]. | Culture vessel |
| [102]. | Gearbox |
| [103]. | Motor |
| [104]. | Temperature controller |
| [105]. | Thermistor |
| [106]. | Heating lamp |
| [107]. | pH meter and controller |
| [108]. | Peristaltic pumps |
| [109]. | pH probe |
| [110]. | Acid or Alkaline reservoir |
| [111]. | Oxygen probe |
| [112]. | DOT meter |
| [113]. | Pressure regulator |
| [114]. | Rotameter |
| [115]. | Air filter |
| [116]. | Medium pump |
| [117]. | Inoculum port |
| [118]. | Cooling water |
| [119]. | Sampling port |
| [120]. | Thermometer |
| [121]. | Foam sensors |
| [122]. | Antifoam adding device |
| [123]. | Antifoam reservoir |
| [124]. | Peristaltic pump |
| [125]. | Condenser |
| [126]. | Culture reservoir |

A pH probe (combination steam sterilizable "Probion", England) and an oxygen electrode (Johnson type) were inserted into the vessel through a moulded silicone gland fitted into the sides of the fermentor, about 12 cm above the bottom plate.

Antifoam feeding was achieved with a peristaltic pump triggered by an antifoam adding device to which foam sensors were connected. Other equipment was similar to that used in 1 liter fermentor experiments (see Section 2.14).

(v) Sterilization and preparation of culture vessel

The method described by Elsworth et al. (1958) was adopted for sterilization of the culture vessel, with minor modifications. The vessel was filled up with 2 percent formalin overnight, then steam at about atmospheric pressure was passed into the fermentor. Steam sterilization was carried out for 4-5 hours, and during this period all the vents were purged occasionally. The filter unit for the inlet air filtration was sterilized in an autoclave at 20 psi for 30 min, then was aseptically connected to the fermentor.

Oxygen and pH probes were soaked in 10% formalin solution before being placed into the fermentor towards the end of the sterilization cycle. Only about 30 min was allowed for steam sterilization of the probes.

(vi) Sampling procedure

Samples were taken through the sampling port which was continually steam sterilized when not in use. Samples taken for assay of glucose, phenylalanine or other compounds were stored at 4° C. before assay, or if it was not possible to assay on the day of sampling, stored at −20° C.

2.15 ANALYSIS OF CULTURE FLUIDS (i) Glucose

Glucose assays were by a modification of the dinitrosalicylic acid method of Miller et al. (1960). It was carried out on culture fluid without including a deproteinization step. Results were calculated using a standard curve prepared by assaying a series of glucose standards concurrently with each test sample.

3,5-dinitrosalicylic acid reagent was prepared by dissolving 182 g of potassium sodium tartrate in about 700 ml of distilled water; 10 g of NaOH, 0.5 g of $Na_2S_2O_3$ and 2 g of phenol were then added successively. Finally, 10 g of dinitrosalicylic acid was added gradually with stirring. After complete solution of the dinitrosalicylic acid added, the reagent was made up to 1 liter with distilled water.

The assay was carried out as follows: 1 ml of sample (0.2–1.0 mg of glucose per ml) and 4.0 ml of dinitrosalicylic acid mixture were incubated for 15 min in boiling water bath and then the tubes were cooled with tap water. Optical densities were read at 640 nm.

(ii) Phosphate

Inorganic phosphorus content was estimated by the method described by Taussky and Shore (1953).

The method involves the reduction of phosphomolybdic acid by ferrous sulphate, which is detected colorimetrically at 700 nm. This method determines only the inorganic phosphorus in a sample which is treated by trichloroacetic acid to remove proteinous materials.

(iii) 3-deoxy-D-arabino-heptulosonate-7-phosphate (DAHP)

DAHP was assayed as described in the section on assay of DAHP synthase (see Section 2.13).

(iv) Phenylalanine

Phenylalanine was assayed mostly by a microbiological method or by a high pressure liquid chromatographic method. The two different methods gave results in close agreement for samples of fermentation liquors (data not presented).

The microbiological method was carried out using a phenylalanine auxotrophic and streptomycin resistant strain of *Escherichia coli* (NST42). It was found that this procedure was highly sensitive, reproducible and particularly convenient for estimating phenylalanine in culture fluids. This assay was also found not to respond to phenylpyruvic acid.

Culture medium for the bioassay contained 0.5 ml of an appropriately diluted sample (25-250 μg of phenylalanine per ml), 0.12 g glucose, 6.0 mg streptomycin and 0.3 mg of washed cells of the strain NST42 in a total volume of 16.5 ml of sterile 56 buffer supplemented with other required nutrients. After 15 hrs. incubation at 37° C. with reciprocal shaking (200 rpm/min), turbidity was measured at 670 nm. Phenylalanine concentrations were calculated using a standard curve (see FIG. [6]) prepared by assaying a series of phenylalanine standard solutions concurrently with each assay.

High pressure liquid chromatography (HPLC) of phenylalanine was carried out using a Waters Liquid Chromatograph (Waters Associates Inc., Milford, MA., U.S.A.) equipped with Waters Model 6000A constant flow pump, Model 440 dual channel ultraviolet detector, Model 660 solven programmer and Model 710B sample processor (WISP 710B).

| Chromatographic conditions were as follows: | |
|---|---|
| Detector: | 254 nm U.V. |
| Column: | Radial-PAK A cartridge using Waters Model RCM-100 Radial Compression Separation System |
| Column temperature: | ambient |
| Mobile phase: | 40% (v/v) methanol (the pH was adjusted to 2.5 with $H_3PO_4$) |
| Flow rate: | 4.0 ml/min |
| Chart speed: | 1 cm/min |

Preparation of samples:

1 ml of sample (culture supernatant fluid) was pumped through the SEP-PAK C18 sample preparation cartridge (Waters Associates) using a 5 ml syringe, and the filtrate was collected in a tube. The cartridge was then eluted with 2 ml of methanol followed by an appropriate volume of distilled water. The eluant was combined with the filtrate to the total volume of 5 ml.

Standard solutions were filtered through 0.45μ pore size cellulose acetate filter before injection into the chromatographic column.

Chromatography:

Prior to the start of actual analysis the mobile phase was pumped under the chromatographic conditions until a stable base line was obtained. After obtaining equilibration of the system, samples and standard solutions were injected.

Phenylalanine concentrations were calculated by comparison of peak height with a standard curve. FIG. [7] shows a chromatographic separation of three aromatic amino acids under the conditions described above.

(v) Tyrosine

The estimation of tyrosine in culture fluids was by the method described by Udenfriend and Cooper (1952). The interaction of 1-nitroso-2-naphthol and tyrosine gives rise to a red compound. This unstable red derivative is changed when heated in nitric acid to a stable yellow substrate which can be separated from excess nitrosonaphthol. The unchanged nitrosonaphthol is extracted into ethylene dichloride. The yellow nitrosonaphthol tyrosine derivative is exactly proportional to the concentration of tyrosine, and detected colorimetrically at 450 nm.

(vi) Tryptophan

Tryptophan was determined by the colorimetric method of Udenfriend and Peterson (1957).

This procedure is based on condensation of the indole with p-dimethylaminobenzaldehyde, and subsequent development of colour in ethanolic solution, in the presence of nitrite. The treatment of samples with 10% (w/v) trichloracetic acid solution to extract tryptophan from cells and to precipitate protein was found to be redundant (Tribe and Pittard, 1979), thus this preliminary step was omitted.

2.16 CALCULATIONS

In many flask and batch fermentor experiments assessment of substrate consumption was found to be uncertain and the yield coefficient; yield per mass of glucose consumed (Yp/s), was therefore quite variable. Yield per mass of cells (Yp/x) was, however, found to be quite reproducible (see also Hempfling et al., 1975 and Tribe, 1979). Hence results from flask and batch fermentor experiments are largely expressed in terms of Yp/x;

Yp/x is defined as $\Delta$[phenylalanine]$\div\Delta$[cell mass]
Specific growth rate $\mu$ is defined as $\Delta/\ln$[cell mass]$\div\Delta$[Time]
q (phenylalanine) was calculated by the equation;
$\mu \times$Yp/x for growing cells or alternatively as $\Delta$[phenylalanine]$\div$[$\Delta$[time]$\times$cell mass] for slowly growing or non-growing cells.

In continuous culture experiments the following yield coefficients were used to assess process productivity;

$$qp = \frac{D \times P}{X} \, (g/g/h)$$

$$qs = \frac{D(S_0 - S_1)}{X} \, (g/g/h)$$

$$Y_{p/s} \frac{qP}{qS}$$

$$Y = \frac{X}{(S_0 - S_1)} \, (g/g)$$

where
X = cell mass concentration (g/l)
P = product concentration (g/l)
$S_o$ = input substrate concentration (g/l)
$S_1$ = substrate concentration in single stage (g/l)

Phenylalanine yield coefficient corrected for glucose utilization for biomass (Yp/s') was calculated by the following equation;

$$Y_{p/s'} = \frac{qp}{qs^{(2)} - qs^{(1)}}$$

where
Yp/s' is the conversion yield of glucose only to the product;
$qs^{(1)}$ is the specific glucose uptake rate for strain NST109;
$qs^{(2)}$ is the specific glucose uptake rate for strain NST74 and
qp is the specific productivity for strain NST74.

CHAPTER 3

RESULTS PART I

GENETIC MANIPULATION OF PHENYLANANINE METABOLISM

This chapter is largely concerned with the genetic manipulations which may be used to remove restrictions on phenylalanine biosynthesis in *E. coli*. This has involved construction of a variety of strains bearing multiple combinations of mutations which were examined for effects on phenylalanine overproduction. A list of the various mutations that were used in the construction of these multiple-mutation strains is given in Table 3.1. From the table it can be seen that several of these mutations had been characterized by other workers prior to the commencement of this project. For example, aroF (FBI$^r$) and tyrR mutations which were important in providing an adequate supply of chorismate for phenylalanine synthesis had been previously characterized, and a pheO$^c$ mutation was available to give derepressed synthesis of phenylalanine branch pathway enzymes.

In addition it was necessary to obtain several extra mutations specially for this project. The most important of these were the pheA mutations which cause the enzyme chorismate mutate-p-prephenate dehydratase (CMP-PDH) to be desensitized to phenylalanine inhibition. These were isolated using a selection for resistance to the phenylalanine analogue, β-thienylalanine, and in an alternative approach, by selection for resistance to the tyrosine analogue, 3-fluorotyrosine.

TABLE 3.1

CHARACTERISTICS OF MUTATIONS AND PLASMIDS USED IN THE STUDIES OF PHENYLALANINE OVERPRODUCTION

| Mutant allele or plasmid[a] | Relevant features of phenotype | Origin or reference |
|---|---|---|
| tyrR366 | fully constitutive synthesis of DAHP synthase Tyr and Phe, shikimate kinase, and aminotransferase | Camakaris and Pittard (1973) |
| aroF394 | DAHP synthase Tyr feedback inhibition resistant | Tribe (1976) |
| aroG103 | DAHP synthase Phe feedback inhibition resistant | This work |
| tyrA4 | lack of chorismate mutase-T-prephenate dehydrogenase | Pittard and Wallace (1966) |
| trpE401 | lack of anthranilate synthase | Tribe (1976) |
| pheO352 | derepressed synthesis of CMP-PDH enzyme | Im and Pittard (1971) |
| pheA101 | CMP-PDH enzyme feedback inhibition resistant | This work |
| PheA102 | CMP-PDH enzyme feedback inhibition resistant | This work |
| aroP::Tn10 | defect in common aromatic transport system by insertion of Tn10 element into aroP gene | This work |
| pUNT20 | increase in enzyme levels because of gene frequency effect | This work |
| pUNT21 | increase in enzyme levels because of gene frequency effect | This work |

[a]The chromosomal location of each of the mutations has been confirmed by appropriate P1 Kc transduction experiments (details not presented)

Another class of β-thienylalanine resistant mutant was found to have feedback resistant DAHP synthase Phe activity, and the mutation causing this resistance established to be an aroG (FBI$^r$) mutation on the basis of linkage to nadA-aroG-gal region of the chromosome (see section 3.1.2).

Extra plasmid-borne copies of pheA gene were introduced into the phenylalanine overproducing strains in order to further increase the levels of the phenylalanine terminal pathway enzymes above the pheO$^c$ level. For this the F-merogenote, pUNT20 and the ColE1-pheA plasmid, pUNT21 were isolated. Both of these plasmids carry mutant pheA alleles which code for a CMP-PDH enzyme that is desensitized to inhibition by phenylalanine (see section 3.2.2).

A relatively detailed description of the isolation and characterization of mutant starting strains is given in the sections that follow (sections 3.1.1, 3.1.2 and 3.1.3). The construction of multiple-mutation strains by recombination from these starting strains is then described.

3.1 ISOLATION AND CHARACTERIZATION OF NEW MUTANT STRAINS

3.1.1 Chorismate mutase-p-prephenate dehydratase feedback resistant mutants (i) 3-fluorotyrosine (FT) resistant mutants Selection for resistance to 3-fluorotyrosine growth inhibition had been originally aimed at yielding prephenate dehydrogenase feedback resistant mutants [tyrA (FBI$^r$)] rather than the pheA (FBI$^r$) mutants which were actually obtained. This involved selection of mutants in which the FT$^r$ locus was linked to the aroF-tyrA-pheA region by a modified version of the method of Somerville et al. (1965) which is based on a concept related to localized mutagenesis.

In this experiment strain AB3259 was chosen as a starting strain. This strain carries a single functional DAHP synthase Phe isoenzyme (i.e. the aroG+ aroF− aroH− genotype) and a wild-type tyrR gene. The rationale for using this strain was based on preliminary FT$^r$ isolations with an aroF+ strain which were taken to suggest that AB3259 might facilitate the isolation of mutants of the tyrA (FBI$^r$) type.

A washed exponential phase culture of strain AB3259 was treated with NTG as described in section 2.11. After phenotypic expression in Luria broth for 4 hours at 37° C., various dilutions of the cells were plated on minimal agar containing 3-fluorotyrosine and incubated for 2 days at 37° C. Sterile 56/2 buffer was added to the surface of the plate on which 100–150 resistant colonies had appeared, and the colonies suspended with the aid of a glass spreader. The suspended cells were then used as hosts in the preparation of a P1 Kc transducing phage lysate.

The resulting lysate was used to transduce a tyrosine auxotroph strain AT2273, selecting for Tyr+ on minimal medium containing 3-fluorotyrosine. This final step ensures that the 3-FT$^r$ mutation is linked to tyrA, which happens to be closely linked to pheA gene (Bachmann et al., 1980). Mutants arising on this selective medium were purified by streaking on the same medium for further tests.

One of the mutants, strain NST5 was, because prephenate dehydrogenase levels were not derepressed as was found with other isolates, examined further to determine if prephenate dehydrogenase was insensitive to feedback inhibition by tyrosine. However, as the results presented in Tables 3.2 and 3.3 show, it was found that the 3-FT$^r$ mutation is located in not tyrA but in the pheA gene. The sensitivity of prephenate dehydrogenase coded by tyrA from strain NST5 to feedback inhibition showed no change and was the same as that of wild-type enzyme, while prephenate dehydratase coded by pheA was revealed to be slightly activated in the presence of phenylalanine instead of being inhibited.

TABLE 3.2

COMPARISON BETWEEN STRAIN NST5 AND ITS tyrA+ CONTROL STRAIN NST12 WITH RESPECT TO SENSITIVITY OF PREPHENATE DEHYDROGENASE TO TYROSINE INHIBITION

| | relative activity (%) | | | |
|---|---|---|---|---|
| Strain | 0.0 mM tyr[a] | 0.1 mM tyr | 0.5 mM tyr | 1.0 mM tyr |
| NST12 | 100 | 90 | 46 | 25 |
| NST5 | 100 | 88 | 44 | 28 |

[a]This shows the final concentration of tyrosine in the reaction mixture.

TABLE 3.3

COMPARISON BETWEEN STRAIN NST5 AND STRAIN AT2273 WITH RESPECT OF SENSITIVITY OF PREPHENATE DEHYDRATASE TO FEEDBACK INHIBITION

| Strain | pheA allele | relative activity (%) | | | | |
|---|---|---|---|---|---|---|
| | | 0.0 mM phe[a] | 0.25 mM phe | 0.5 mM phe | 1.0 mM phe | 2.0 mM phe |
| AT2273 | pheA+ | 100 | 68 | 36 | 26 | 27 |

TABLE 3.3-continued
COMPARISON BETWEEN STRAIN NST5 AND STRAIN
AT2273 WITH RESPECT OF SENSITIVITY OF
PREPHENATE DEHYDRATASE TO FEEDBACK INHIBITION

| Strain | pheA allele | relative activity (%) | | | | |
|---|---|---|---|---|---|---|
| | | 0.0 mM phe[a] | 0.25 mM phe | 0.5 mM phe | 1.0 mM phe | 2.0 mM phe |
| NST5 | pheA101 | 100 | 103 | 105 | 107 | 111[b] |

[a]This shows the final concentration of phenylalanine in the incubation mixture for enzyme assay.
[b]The cause of this apparent activation by phenylalanine was not further investigated.

Hence, the mutation established to be located in the structural gene for prephenate dehydratase, namely the pheA gene, and causing the altered resistance to the end-product inhibition was designated as pheA101. Further data relating to the phenotype of strains carrying the pheA101 mutation, including the sensitivity of chorismate mutase-p to feedback inhibition, will be given in section 3.2.

(ii) β-thienylalanine resistant mutants

Isolation of mutants in which the mutation desensitizes chorismate mutase-p-prephenate dehydratase activity to phenylalanine inhibition was also achieved by the use of the phenylalanine analogue β-thienylalanine.

The isolation procedure used was very similar in principle to that for obtaining 3-fluorotyrosine resistant mutants (see section 2.11 and section 3.1.1). The starting strain for this selection was strain JP2250 which has already a pheO352 mutation and thus chorismate mutase-p-prephenate dehydratase in this strain is formed at the derepressed level (see Table 3.6). After the treatment with NTG mutagen followed by phenotypic expression, the cells of strain JP2250 were plated on a minimal agar containing 62-thienylalanine, and incubated for 2 days at 37° C. A P1 Kc phage lysate was prepared using colonies from the β-thienylalanine plate as host cells. The lysate was then used to transduce strain JP2257, selecting Phe+ transductants on the same medium as used for the initial isolation of β-thienylalanine resistant mutants. The transductant colonies on this plate were purified and screened by cross-feeding tests using a pheA− indicator strain. One of the strong cross-feeders, strain NST17, was characterized as having chorismate mutase-p and prephenate dehydratase activities that were fully resistant to the phenylalanine inhibition (details not presented), and the allele responsible was designated as pheA102. Moreover, the synthesis of these enzymes in the strain NST17 was found to be produced constitutively and at derepressed levels just as with the parent strain (see Table 3.6).

3.1.2 DAHP synthase Phe feedback resistant mutant

A mutation causing DAHP synthase Phe to be desensitized to feedback inhibition was obtained during isolation of pheA feedback resistant mutants using β-thienylalanine. β-thienylalanine (Ezekiel, 1965) is reported to inhibit cell growth by being incorporated into protein instead of phenylalanine, and because the extent of incorporation is dependent on the relative intracellular level of phenylalanine, any class of mutant which increases phenylalanine supply sufficiently, such as pheA (FBI[r]) mutations or mutations abolishing inhibition of DAHP synthase activity by phenylalanine, would be expected to confer analogue resistance.

The starting strain JP2250 carries pheO352 mutation which causes derepression for the synthesis of chorismate mutase-p-prephenate dehydratase and displays the phenotype of resistance to growth inhibition by p-fluorophenylalanine. Strain JP2250 was treated with NTG mutagen, and after phenotypic expression the cells were plated on medium MM containing $5 \times 10^{-3}$M β-thienylalanine. The resistant clones appearing on these plates after 2 days incubation at 37° C. were purified and tested for their ability to cross-feed a phenylalanine auxotroph. Several strains which were found to be strong cross-feeders were retained for further analysis by enzyme assays using cell-extracts. All the mutants selected were found, however, to show, with respect to prephenate dehydratase activity, nearly the same sensitivity to feedback inhibition as that of the parental strain (details not presented). Hence, one of these isolates was examined to determine the sensitivity of its DAHP synthase Phe activity to phenylalanine inhibition. As shown in Table 3.4, the mutant, NST11, was found to differ distinctly from the parental strain JP2250 is that its DAHP synthase activity is fully resistant to the end-product inhibition.

TABLE 3.4
COMPARISON BETWEEN STRAIN NST11 AND ITS
PARENTAL STRAIN JP2250 WITH RESPECT TO DAHP
SYNTHASE ACTIVITY, AND THE SENSITIVITY OF
THAT ACTIVITY TO PHENYLALANINE INHIBITION

| Strain | aroG allele | Sp. Act. (mU/min/ mg of protein) | relative activity (%) | | | |
|---|---|---|---|---|---|---|
| | | | 0.25 mM[b] phe | 0.5 mM phe | 1.0 mM phe | 2.0 mM phe |
| JP2250 | + | 180.0 | 4.9 | 4.0 | 3.5 | 4.5 |
| NST11 | 103 | 198.0 | 96.7 | 93.5 | 102.6 | 107.0[a] |

[a]The cause of this apparent activation in the presence of higher concentration of phenylananine was not further investigated.
[b]This represents the final concentration of phenylananine in the incubation mixture for the enzyme assays.

Referring again to the above table, it can be seen that specific activities of DAHP synthase from both the parent and mutant strains are nearly the same, which is a different pattern from that exhibited by the aroG (FBI[r]) mutant, JP2246, isolated by Tribe (1976) in that the level of DAHP synthase specific activity for JP2246 was found to be less than one fourth of that for its parent strain KB3100.

3.1.3 Isolation of an aroP mutant

The aroP gene specifies the common aromatic transport system, which is involved in transport of each of the three aromatic amino acids; phenylalanine, tryptophan and tyrosine (Piperno et al., 1968). It was decided that a transposon (Tn10) induced aroP mutant would be isolated in order to examine the effects of the aroP gene on phenylalanine production. A Tn10 induced mutation has the advantage that presence of the mutation can be tested using the tetracycline resistance phenotype, rather than analogue resistance or other traits which are technically difficult to determine with these multiple-mutation phenylalanine overproducing strains.

The procedure for obtaining an aroP mutation caused by insertion of Tn10 into the aroP gene, was based on the known location of aroP close to the leu gene of *E. coli*, and the concept of screening Tn10 insertion strains for β-thienylalanine resistance as an unselected marker (β-thienylalanine resistance is the usual phenotype exhibited by aroP mutants). A P1 Kc generalized transducing phage lysate using a pool of wild-type cells with TN10 inserted in random locations (W3110::Tn10) for growth of bacteriophage was prepared according to the procedure described in section 2.5. The resulting P1 Kc lysate which thus contained a mixture of transducing particles with Tn10 in different locations, was used to transduce the leu⁻ recipient strain JC411, selecting Leu⁺ type on minimal media containing 10 μg/ml tetracycline. This enables Tn10 insertions near leu to be easily isolated (see FIG. [8]). These transductants were then screened for β-thienylalanine resistance as an unselected marker. Of 432 Leu⁺ and Tet' transductants tested, only one colony showed the aroP⁻ phenotype, and was, after being purified, named strain NST49. In addition to its resistance to β-thienylalanine this strain is also resistant to 5-methyltryptophan ($2 \times 10^{-4}$ M) and p-fluorophenylalanine ($2 \times 10^{-4}$ M), other common phenotypes of aroP⁻ strains.

To confirm the map location of this mutation a transduction analysis of markers in the aroP region was carried out. As shown in Table 3.5 the tetracycline and β-thienylalanine double resistance; the phenotype of Tn10 inserted aroP mutation was cotransduced at a frequency of 33.6% with leu⁺ marker, and all the tetracycline resistant transductants tested were found to be also resistant to β-thienylalanine. These results provide firm evidence that the aroP mutation in the strain NST49 is derived by Tn10 insertion within the aroP gene, and are in full accordance with previously reported location of the aroP⁻ locus (Brown, 1970). Hence, this mutant allele of aroP gene was described in aroP::Tn10.

TABLE 3.5

P1 Kc-MEDIATED TRANSDUCTION ANALYSIS OF MARKERS IN THE aroP REGION.

| Donor | Recipient | Selected Marker | No.[a] | Unselected[b] Marker (No.) | Frequency (%) |
|---|---|---|---|---|---|
| NST49 | JC411 | Leu⁻ | 110 | Tet' (37) | 33.6 |
| | | Leu⁺ | 110 | β-TA'.Tet' (37) | 33.6 |
| | | Tet' | 219 | Leu⁺ (132) | 60.3 |
| | | Tet' | 219 | β-TA' (219) | 100.0 |

[a]Number of selected transductants screened for unselected marker.
[b]Tetracycline was supplemented 10 μg per ml of medium, and the concentration of β-thienylalanine in the medium was $5 \times 10^{-4}$ M.

3.2 CONSTRUCTION OF STRAINS BY RECOMBINATION

After the collection of regulatory and auxotrophic mutations had been assembled, extensive use was made of recombination techniques to construct other strains. Before proceeding to an outline of the main strain breeding programme, two smaller series of constructions will be described, namely the construction of double pheApheO mutants by recombination, and gene conversion of plasmids.

3.2.1 Isolation of pheO352 pheA101 double mutation strains

The construction of a recombinant strain which carries pheO352 and pheA101 double mutations was one of the most important preliminary steps for constructing phenylalanine hyperproducing strains. Because pheA and pheO are so close together on the chromosome, recombination between the two is relatively infrequent, but once a double mutant is constructed it is expected that both will be inherited together almost as if they are a single mutation.

Preliminary tests suggested that p-fluorophenylalanine would be a useful analogue for directly selecting a recombinant double-mutation strain. Accordingly, a P1 Kc phage lysate was prepared using the pheA101 strain NST5 as a host strain, and the resulting lysate was used to transduce the pheO352 pheA⁻ strain JP2257, selecting pheA⁺ transductants on medium MM containing $5 \times 10^{-3}$ M p-fluorophenylalanine and shikimic acid. The colonies on this selective medium were screened for the ability to overproduce phenylalanine by the simple cross-feeding tests. One of the strong cross-feeders was purified for further characterization and designated as strain NST16. Data illustrating the degree to which prephenate dehydratase of the strain NST16 differs from those of the reference strains, JP2250 (pheA⁺pheO352) and At2273 (pheA⁺.pheO⁺) in the sensitivity to feedback inhibition, are given in FIG. [9]. As can be seen from the figure, the sensitivity of prephenate dehydratase from the recombinant strain NST16 exhibits a very similar pattern to that of the enzyme from donor strain NST5. The success of this construction confirms the genetic location of pheA101, and the similarity of the sensitivity profiles obtained supports the conclusion that the double mutant arose by recombination.

Further investigation of the characteristics of the strain NST16 is summarized in Table 3.6 together with data for strain NST17 which has a similar genotype to strain NST16 except that the original isolation of the pheA (FBI') allele involved selection for resistance to β-thienylalanine (refer to section 3.1.1). In this table specific activities of prephenate dehydratase of the recombinant NST16 and the mutant NST17 are compared with those of the control strains grown in the conditions of repression and non-repression.

Referring again to Table 3.6, the enzyme levels in cell-free extracts prepared from the three pheO352 strains, JP2250, NST16 and NST17 were approximately 15–18 fold higher as expected than that of the strain AT2273 carrying a wild-type pheO allele. These results are in agreement with the original report on the pheO352 mutation (Im and Pittard, 1971).

TABLE 3.6

SPECIFIC ACTIVITIES OF PREPHENATE DEHYDRATASE FROM CONTROL AND MUTANT STRAINS

| | | Prephenate dehydratase specific activity | |
|---|---|---|---|
| Strain | Relevant characteristics | Cells grown in medium MM | Cells grown in medium MM supplemented with end products[a] |
| NST5 | pheA101 pheO⁺ | 0.7 | 0.8 |
| AT2273 | pheA⁺ pheO⁺ | 24.1 | 19.5 |
| JP2250 | pheA⁺ pheO352 | 388 | 398 |

TABLE 3.6-continued

SPECIFIC ACTIVITIES OF PREPHENATE DEHYDRATASE
FROM CONTROL AND MUTANT STRAINS

| Strain | Relevant characteristics | Prephenate dehydratase specific activity | |
|---|---|---|---|
| | | Cells grown in medium MM | Cells grown in medium MM supplemented with end products[a] |
| NST16 | pheA101 pheO352 | 426 | 412 |
| NST17 | pheA102 pheO352 | 368 | 363 |

[a]End products included 0.5 mM phenylalanine, 0.5 mM tyrosine and 0.2 mM tryptophan.

Furthermore, the presence of the aromatic end-products in culture medium has no effect on enzyme levels although the same finding was made with all strains examined, including the pheO+ strain AT2273. These results taken together with the data shown in FIG. [9] provide clear evidence that the recombinant strain NST16 and also the mutant strain NST17 have double mutations, namely pheA (FBI$^r$) and pheO352 on their chromosomes. Another feature of this experiment is that the levels of prephenate dehydratase activity in the strain NST5 were found to be unusually low under both repressing and non-repressing conditions. This is probably due to the repressing effect of high level of intracellular phenylalanine caused by deregulation of biosynthesis.

Both activities of the CMP-PDH complex, namely chorismate mutase and prephenate dehydratase activities are reported to be feedback controlled by the allosteric inhibitor phenylalanine, although the dehydratase activity is generally more sensitive than the mutase activity (Dopheide et al., 1972; Gething et al., 1976). Hence the sensitivity of chorismate mutase from strain NST16 was also examined together with that of pheA+ control strains, and the data obtained are given in FIG. [10].

As can be seen from the figure, the control strains carrying pheA+ allele show, as expected, 13–15 percent inhibition of their mutase activities in the presence of 1 mM phenylalanine, but the mutase activity from the pheA101 strain is revealed to be approximately 15 percent activated at the same concentration of effector. This shows that the pheA101 mutation affects both activities of the enzyme complex.

3.2.2 Gene conversion of plasmids

As shown in Table 3.6, the pheO352 mutation causes elevation of the levels of phenylalanine biosynthetic enzymes to levels approximately 17-fold higher than those of the strains carrying wild type pheO gene. However, to shunt chorismate supplied more efficiently down to phenylalanine pathway it would seem to be advantageous to increase the enzyme levels even further by introducing either a F-pheA or the ColE-pheA multi-copy plasmid specifying a feedback resistant prephenate dehydratase.

Briefly, the procedure for the construction of such an F prime plasmid pUNT 20 is as follows, further experimetal details of this procedure are given in section 2.10. Plasmid F'142 (F'-tyrA+ pheA+ pheO+) was transferred into the recipient strain NST17 that carries on the endogenote alleles pheA (FBI$^r$) pheO352 and tyrA−, to which the exogenoate was to be gene converted. The resulting conjugant, NST17 (F'142), was then plated on medium formulated to favour growth of homogenotic cells; pheA (FBI$^r$).pheO352/pheA (FBI$^r$).pheO352 rather than heterogenotic cells; pheA (FBI$^r$).pheO352/pheA+.pheO+. The conjugants isolated from the selective media were again mated with the pheA−recA− recipient strain NST40, and PheA+ conjugants were selected, and purified after screening by cross-feeding tests. One of the transconjugants was characterized by measurement of levels of prephenate dehydratase activity in cell extracts, and also by examining the sensitivity of the enzyme to feedback inhibition. The results obtained are shown in Table 3.7. From the data in the table, it is clear that this transconjugant harbours a mutant form of F'-142 that carries both pheO352 and pheA (FBI$^r$) mutant alleles on the exogenote, the mutations on the exogenote being derived from the mutations on the initial recipient strain's chromosome by a gene-conversion event.

TABLE 3.7

COMPARISON BETWEEN PLASMID F'-142 AND pUNT20
WITH RESPECT TO PREPHENATE DEHYDRATASE ACTIVITY,
AND SENSITIVITY OF THE ACTIVITY TO FEEDBACK
INHIBITION[a]

| Strain | Relevant genotype | Prephenate dehydratase | | | |
|---|---|---|---|---|---|
| | | Specific activity | relative activity in the presence of phe. (%) | | |
| | | | 0.0 mM | 1.0 mM[b] | 2.0 mM[b] |
| NST62 | pheA−pheO+/F142 | 27.0 | 100.0 | 37.7 | 35.8 |
| NST63 | pheA−pheO+/pUNT20 | 472 | 100.0 | 95.0 | 93.0 |

[a]Cell extracts were prepared from cells grown in medium MM in shaken flask cultures at 37° C.
[b]These show the final concentration of phenylalanine in the reaction mixture for enzyme assay.

Another mutant plasmid was isolated starting with the multi-copy plasmid pMU307 (ColE1-pheA plasmid), and this mutant ColE1-pheA plasmid was named as plasmid pUNT21. The procedure for the isolation of the plasmid pUNT21 was similar to that for the plasmid pUNT20, and involved also the use of gene conversion techniques. However, possibly because of the great instability of the transformants obtained by transforming phenylalanine overproducing strains with the plasmid pMU307, transformation was found to be an inadequate procedure for transferring this plasmid even though being a usual transfer method for this kind of plasmid. Hence, in order to transfer this non-conjugal plasmid by a mating process, strain NST67 was prepared by introducing an F'-lac factor (F'128) into strain NST66 which already carried the plasmid pMU307, and the strain NST67 was used as one of the starting strains for isolating the gene-converted mutant plasmid of pMU307 using a similar gene-conversion technique to that for isolating pUNT20. The resulting mutant plasmid, pUNT21, was again transferred into the pheA⁻ pheO⁺ recA⁻ strain NST40 in order to confirm that the pheA (FBI$^r$) mutant allele is carried on the exogenote.

Data relating to the phenotype of the strain NST76 described above are given in Table 3.8. From the results shown in the table, it is confirmed that the pheA (FBI$^r$) mutation was transferred from the endogenote of strain NST17 to the plasmid pMU307 genome.

TABLE 3.8

SENSITIVITY OF PREPHENATE DEHYDRATASE TO PHENYLALANINE INHIBITION[a]

| Strain | Specific Activity | Relative Activity % | | | |
|---|---|---|---|---|---|
| | | 0.0 mM | 0.25 mM | 0.5 mM | 1.0 mM[b] |
| NST76 | 612.0 | 100.0 | 106.3 | 105.8 | 103.1 |

[a]Cell extract was prepared from cells grown in medium MM in shaken flask culture.
[b]These show the final concentration of phenylalanine in the reaction mixture.

3.2.3 Main strain breeding program

The main approach for obtaining phenylalanine overproducing strains involves, in addition to a sequence of strains that are made to be investigated directly for phenylalanine production, a completely different set that were used as starting strains for selection of mutants. Mutations arising in this second set of strains are characterized as described in the previous sections, and a choice made of those most suitable for the present project. The next stage involves the use of gene-transfer methods; transduction, conjugation and transformation, to move the mutations of choice into the set of strains used for phenylalanine production. This construction of strains of defined genotype was greatly facilitated by using transduction techniques with the generalized P1 Kc transducing phage which relied heavily on data relating to the genetic location of mutations. In [FIG. 11], chromosomal locations of genes relevant to this work, and markers with which they can be co-transduced are shown.

In the main series of strain construction, strain JP2241 (Tribe, 1976; Tribe and Pittard, 1979) was used as a starting strain, since this strain has several features which would favour phenylalanine overproduction: it carries already aroF (FBI$^r$) tyrR⁻ trpE⁻ and tyrA⁻ mutations which are expected to be important in determining phenylalanine yield. The strain has also many other useful mutations for constructing phenylalanine hyperproducing strains by using P1 Kc transduction techniques (refer to Table 2.1 for further details of the genetic characteristics of the strain JP2241).

An outline of the main gene transfers that were made to produce the multiple-mutation strains for phenylalanine overproduction studies using the strain JP2241 as the starting strain, is given in FIG. [12].

The main part of this program was the construction of strain NST37, which has aroF (FBI$^r$), aroG (FBI$^r$) tyrR, pheA (FBI$^r$), pheO$^c$, tyrA and trpE mutations, and it was derived in 7 steps from strain JP2241. Additional strains from NST37 include strain NST74, which is a prototrophic strain specially constructed to enable higher cell densities to be obtained, and pheA plasmid containing strains NST64 and NST70. Other strains were made to elucidate the role of key enzymes and transport systems.

3.3 EFFECT OF MUTATIONS ON PHENYLALANINE OVERPRODUCTION

After construction of these various multiple-mutation strains, a series of comparisons between strains were made with the aim of elucidating the role of the individual control circuits in restricting phenylalanine hyperproduction.

As a preliminary experiment to help in determining the appropriate sampling time for these experiments, the kinetics of phenylalanine formation in shaken flask culture was determined using one of the higher yielding multiple-mutation strains. The strain used was strain NST37, which has the genotype aroF (FBI$^r$) aroG (FBI$^r$) tyrR⁻ pheA (FBI$^r$) pheO$^c$ tyrA⁻ trpE⁻. It was cultured so that the final cell density was limited by the tyrosine content of the medium (initial concentration of tyrosine; 0.1 mM); the other nutrient requirements were supplemented in excess. It can be seen from FIG. [13] that in this experiment the major part of phenylalanine production occurs during late-exponential to stationary phase of cell growth, and the phenylalanine output prior to mid-exponential phase is relatively insignificant. Hence, it was decided that stationary phase (24 h of incubation) values of phenylalanine yield (Yp/x) would be used as a basic for comparison of a variety of different strains' phenylalanine overproduction in shaken flask cultures.

After carrying out this initial determination of batch kinetics in shaken flask culture, experiments were carried out to compare the yields of phenylalanine for strains carrying various different combinations of mutations. For reasons of practicality, comparisons were made largely using shaken flask cultures, but essentially similar kinetics were obtained with both flask and fermentor cultures. Data obtained from these strain comparisons are presented in the sections that follow. A discussion of the more detailed analysis of process kinetics under more controlled conditions using fermentors and the effects of environmental parameters that was carried out is reserved for the next chapter.

3.3.1 Effect of changes to common pathway

Group 1 strains of Table 3.9 are a series of strains which, except strain AT2273 (tyrR+), lack repression control of DAHP synthase and which differ from one another in DAHP synthase isoenzyme content; all the strains have a wild type phenylalanine terminal pathway. The series are arranged in order of increasing effective DAHP synthase activity in vitro as deduced from their known isoenzyme contents. It can be seen from the data on this group of strains that phenylalanine yield is significantly affected by the level of DAHP synthase present in the cells. Both a desensitized DAHP synthase Phe (compare strains NST44 and NST45; NST47 and NST54) and a desensitized DAHP synthase Tyr (compare strains NST47 and NST43; NST54 and NST45) make a significant contribution to increase yield, with the former isoenzyme appearing to have larger effect.

Group II strains of Table 3.9 lack both inhibition and repression control of the phenylalanine terminal pathway as well as the indicated changes to the common pathway. By comparison of the two strains in this group it can be seen that introduction of a desensitized DAHP synthase Phe isoenzyme has an effect on yield with these strains as well as with group I strains. It should be noted that far better yields were obtained with group II strains, which have changes to both the common pathway and the phenylalanine terminal pathway (other aspects of this table are discussed in section 3.3.2).

TABLE 3.9

COMPARISON OF YIELD OF PHENYLALANINE OBTAINED WITH VARIOUS MUTANTS IN SHAKEN FLASK CULTURES

| Strain[a] | DAHP synthase isoenzyme phenotype[b] phe | tyr | CM-P-PDH phenotype[c] | Yield of phenylalanine Yp/x % w/w |
|---|---|---|---|---|
| Group I | | | | |
| AT2273 | + | + | wild-type | <0.1 |
| NST47 | − | + | wild-type | <0.1 |
| NST43 | − | FBI[r] | wild-type | 1.7 |
| NST44 | + | FBI[r] | wild-type | 4.5 |
| NST54 | FBI[r] | + | wild-type | 20.0 |
| NST45 | FBI[r] | FBI[r] | wild-type | 25.0 |
| Group II | | | | |
| NST21 | − | FBI[r] | deregulated | 48.0 |
| NST26 | FBI[r] | FBI[r] | deregulated | 72.0 |

Footnote:
[a]All the strains except strain AT2273 also carry aroH− tyrR− tyrA− and trpE− mutations. The relevant genotype of strain AT2273 is aroF+ aroG+ aroH+ tyrR+ tyrA− and trpE+.
[b]Notations used: −, isoenzyme absent; +, wild type isoenzyme present; FBI[r], isoenzyme desensitized to endproduct inhibition.
[c]Wild type indicates that both inhibition and repression are functional; deregulated indicates that both are absent.
[d]Cells were grown in Medium MMB - 20 g/l glucose for 24 hours. Final cell densities were limited by the tyrosine content of the medium; the final concentration of tyrosine being 10 mg per liter.

The effects of removal of repression control on common pathway enzymes were also studied. Data relating to this are given in Table 3.10 which correlates levels of the two key enzymes in phenylalanine biosynthesis, namely DAHP synthase and prephenate dehydratase, and phenylalanine yields. The different strains comprise a tyrR+ control strain and two tyrR− strains. From Table 3.10, it can be seen that all three strains have nearly the same prephenate dehydratase activities but as not unexpectedly, the DAHP synthase level of the tyrR+ strain NST72 is approximately one third of those of the two tyrR− strains. The tyrR mutation was also found to exert a critical role in phenylalanine formation, and to boost phenylalanine yield by a factor of approximately ten.

TABLE 3.10

EFFECT OF tyrR MUTATION ON PHENYLALANINE YIELD BY MULTIPLE-MUTATION STRAINS IN SHAKEN FLASK CULTURES

| Strain | Relevant[a] genotype | DAHP synthase Sp. act. | Prephenate Dehydratase Sp. act. | Yield of phenylalanine at 24 h Y p/x % w/w[b] |
|---|---|---|---|---|
| NST72 | tyrR+ Tet[r] | 209 | 430 | 6.1 |
| NST71 | tyrR− Tet[r] | 594 | 428 | 61.0 |
| NST37 | tyrR− Tet[s] | 590 | 413 | 65.0 |

[a]The strains also carry aroF (FBI[r]) aroG (FBI[r]) pheA (FBI[r]) pheO[c] trpE− tyrA− mutations. Strain NST37 differs from strain NST71 and NST72 in that it lacks a Tn10 insertion, which is irrelevantto interpretation of these results.
[b]In all strains thyrosine was the growth limiting nutrient.

3.3.2 Effects of changes to phenylalanine pathway

Table 3.11 shows a series of strains that were compared to determine the effect of changes to phenylalanine terminal pathway regulation on phenlalanine yield, under conditions where inhibition and repression of DAHP synthase are still operative. Measurements were also made on cell extracts of these strains of prephenate dehydratase activity so that this could be related to phenylalanine yield. Since two of the strains have CMP-PDH enzymes that are fully sensitive to phenylananine inhibition, whereas the other two strains have mutant forms of the enzymes that are desensitized to feedback inhibition, experimental data are also included in the table showing relative prephenate dehydratase specific activities in the presence of 1 mM phenylalanine, which are used as an approximate measure of the effective in vivo level of enzyme activity.

TABLE 3.11

COMPARISON, USING SHAKEN FLASK CULTURES, OF MUTANTS AFFECTED IN PHENYLALANINE PATHWAY

| Strain | Relevant Genotype | Relative prephenate dehydratase sp. act.,[a] No phe. added | 1 mM phe. added to reaction mixture | Yield of[b] phenylalanine at 24 h Yp/x % w/w |
|---|---|---|---|---|
| AT2273 | pheA+ pheO+ | 5.4 | 1.4 | <0.1 |
| NST9 | pheA (FBI[r]) pheO+ | 0.15 | 0.15 | 4.7 |
| JP2250 | pheA+ pheO[c] | 87.0 | 20.0 | 6.4 |
| NST16 | pheA (FBI[r]) pheO[c] | 100.0 | 105.0 | 12.0 |

[a]Specific activities found in cell extracts are expressed relative to the value obtained with strain NST16 with no phenylalanine added to the reaction mixture, which is taken as 100 percent.
[b]Cells were grown in Medium MMB- 20 g/l glucose supplemented with the excess amount of auxotrophic requirements except tyrosine; a growth limiting nutrient.

As can be seen from the above table the introduction of single mutation either desensitizing CMP-PDH to phenylalanine inhibition [pheA (FBI[r])] or removing repression [pheO[c]] was found to cause significant phenylalanine overproduction.

Relative enzyme activity measurements reveal unusually low enzyme levels in the pheA (FBI[r]) strain NST9. This presumably is due to the operation of more effective repression of enzyme synthesis than occurs in the control strain AT2273, since in other strains in which repression is removed (that is in pheO[c] strains) the pheA (FBI[r]) mutation does not decrease enzyme levels, as can be seen by comparing the data for strains JP2250 and NST16 given in Table 3.11.

Although the double pheA (FBI[r]) pheO[c] mutation strain NST16 gives the highest yield, comparison of the last two columns of the table reveals that the increase in yield is not in proportion to the high level of phenylalanine resistant prephenate dehydratase activity produced by the strain. Much higher yields of phenylalanine were, however, obtained in other strains which have the same phenylalanine pathway enzyme content as strain NST16, but which have in addition alterations to common pathway regulation. For example, the last two strains of Table 3.9, namely strain NST21 and NST26, give higher yields than the last strain of Table 3.11, strain NST16, the relevant difference being that with strains NST21 and NST26 mutations affecting the phenylalanine terminal pathway have been combined with mutations removing controls on the first step of the common pathway, whereas with strain NST16 this step is still sensitive to feedback inhibition and repression.

Effects of removal of phenylalanine terminal controls are also apparent from other comparisons within Table 3.9. This can be seen by comparing the yields obtained with pheA+ pheO+ strain NST47 and pheA (FBI[r]) pheO[c] strain NST21, and also by comparing the pheA+ pheO+ strain NST45 with the pheA (FBI[r]) pheO[c] strain NST26.

Further evidence relating to the effects of abolishing of the controls acting on the common and the phenylalanine terminal pathways on phenylalanine yield was obtained from cross-feeding tests. Results typical of these tests are shown in FIG. [14]. It is apparent from comparison of the genetic characteristics and zone-sizes shown for the strains in the figure with the data in Tables 3.9 and 3.11 that there is an agreement between the two sets of data.

3.3.3 Tyrosine and tryptophan pathways

The phenylalanine pathway is but one of several pathways diverging from chorismate, and it seemed likely that diversion of chorismate down these other pathways might, under certain conditions, affect phenylalanine yields. To test for such effects the following experiment was carried out. Derivatives of strain NST21 which is blocked at the first reactions of the tyrosine and tryptophan pathways, were prepared so that these pathways became unblocked, and the resulting strains were compared with one another for phenylalanine production in flask experiments.

As a further test, the effect of supplementing the growth medium of the unblocked strain with the particular amino acid was also examined, on the assumption that this would tend to block flow of chorismate down the pathway by enhancing the operation of feedback controls. The results of these tests are shown in Table 3.12, from which it can be seen that although large differences in yield were not observed there is a consistent trend, with the unblocked tyrA+ trpE+ strain NST30 in the absence of added tyrosine and tryptophan giving the lowest yield, and the tyrA− trpE− blocked strain NST21 giving the highest yield.

TABLE 3.12

RELATIONSHIP BETWEEN TYROSINE AND TRYPTOPHAN PATHWAY METABOLISM AND YIELD OF PHENYLALANINE IN SHAKEN FLASK CULTURE

| Strain | Relevant[a] Genotype | Supplement to medium[b] Tyrosine | Tryptophan | Yield of phenylalanine at 24 h. Y p/x % w/w |
|---|---|---|---|---|
| NST30 | tyrA+ trpE+ | −[c] | − | 30 |
|  |  | + | + | 38 |
| NST29 | tyrA+ trpE− | − | + | 39 |
|  |  | + | + | 41 |
| NST22 | tyrA− trpE+ | + | − | 34 |
|  |  | + | + | 38 |
| NST21 | trpA− trpE− | + | + | 47 |

[a]All the strains also carry aroF (FBI') aroG− pheA (FBI') pheO[c] and tyrR mutations.
[b]Medium MMB - 20 g/l glucose was used and supplemented with 42 mg of tyrosine per liter, and 20 mg of tryptophan per liter. In all the strains histidine was used as the limiting nutrient and added at 17.5 mg to 1 liter of the medium; the other nutrient requirements were in excess.
[c]Notations used: −, absence of supplement, and +, presence of supplement.

3.3.4 Effect of tonB mutation on phenylalanine yield

Several branch pathways for the synthesis of aromatic compounds other than the specific pathways for point compound, chorismate . . . A priori it could be expected that conditions which lead to excessive production of these other substances are potentially causes of reduction in phenylalanine production. Actually one of the potential problems in relation to tryptophan production was reported to be excessive production of enterochelin (Yound and Gibson, 1969; Tribe, 1976) . . . . [T]he synthesis of the enzymes of the enterochelin pathway derepressed by starvation for iron, and this could cause excretion of large quantities of enterochelin (McCray and Herrmann, 1976). Another related problem encountered in the tryptophan study of Tribe was decreased tryptophan output of tonB mutants. The effects of lesions in tonB gene on phenylalanine overproduction were, therefore, examined. Data relating to this are given in Table 3.13, which compares yields obtained with the tonB− strain NST31 and its tonB+ counterpart strain NST21.

As can be seen in the table, the tonB− strain NST31 excretes significantly less phenylalanine than the tonB+ control strain. This is in accordance with the results obtained in the studies of a tonB− effect on tryptophan overproduction by mutants of *E. coli* (Tribe, 1976). In a later section (see section 4.2.1), effect of $Fe^{+3}$ ion content in the culture medium are examined.

TABLE 3.13

COMPARISON BETWEEN tonB+ AND tonB− STRAINS WITH RESPECT TO YIELD OF PHENYLALANINE[a]

| Strain | Relevant genotype | Yield of phenylalanine at 24 h Y p/x % w/w |
|---|---|---|
| NST21 | aroF (FBI').pheA (FBI') pheO[c] tyrR− tonB+ | 43 |
| NST31 | aroF (FBI').pheA (FBI') pheO[c] tyrR− tonB− | 17 |

[a]Shaken flask cultures in medium MMD were used; this medium contains 200 μM $Fe^{+3}$, 10 g/l CaCO₃. Final pH of the medium was 7.0 to 7.2. Tyrosine was used as the growth limiting nutrient.

3.3.5 Effect of further increases in phenylalanine pathway enzyme levels

The pheO352 mutant allele has been shown to cause the derepressed level of the multifunctional enzyme chorismate mutase-p-prephenate dehydratase. The levels of prephenate dehydratase in cell-free extracts prepared from the pheO352 strains were approximately 17-fold higher than that of the strain which carries a wild-type pheO gene (refer to Table 3.6). Not unexpectedly, the introduction of this mutation was found to significantly increase phenylalanine yields (see Table 3.11).

To increase the enzyme levels even further, cells were made diploid for the phenylalanine operon genes by introducing the F- merogenote pUNT 20, and made to have multi-copies of the genes by introducing the mutant ColEl-pheA plasmid pUNT 21. Both of these plasmids carry mutant pheA alleles which code for a chorismate mutase-p-prephenate dehydratase desensitized to feedback inhibition by phenylalanine (refer to Table 3.7 and Table 3.8), and also pheO[c] mutations. The effects of introducing these plasmids both on the levels of prephenate dehydratase and on the yield of phenylalanine were investigated, and the results are shown in Table 3.14.

TABLE 3.14

EFFECT OF PRESENCE OF PLASMIDS ON OUTPUT OF PHENYLALANINE IN SHAKEN FLASK CULTURE[a]

| Strain | Relevant genotype[b] | Prephenate dehydratase specific activity | Yield of phenylalanine at 24 h. Y p/x % (w/w) |
|---|---|---|---|
| NST45 | pheA+ pheO+ | 54 | 23 |
| NST37 | pheA (FBI') pheO[c] | 421 | 75 |
| NST64 | pheA (FBI') pheO[c] (pUNT20) | 554 | 107 |
| NST70 | pheA (FBI') pheO[c] | 923 | 129 |

TABLE 3.14-continued

EFFECT OF PRESENCE OF PLASMIDS ON OUTPUT OF PHENYLALANINE IN SHAKEN FLASK CULTURE[a]

| Strain | Relevant genotype[b] | Prephenate dehydratase specific activity | Yield of phenylalanine at 24 h. Y p/x % (w/w) |
|---|---|---|---|
| | (pUNT21) | | |

[a]For determining yields of phenylalanine the strains were grown in medium MMB - 20 g/l glucose. Tyrosine was used as a growth-limiting factor and the final concentration of this amino acid was 10 mg per liter.
For preparing the cell-free extracts for enzyme assays, cells were grown in medium MM - 20 g/l glucose.
[b]All the strains also carry aroF (FBI[r]) aroG (FBI[r]) and tyrR[−] mutations.

As can be seen in this table, there is a direct relationship between prephenate dehydratase activity in the cell extracts of the strains examined and the yield of phenylalanine obtained in shaken flask culture.

3.3.6 Effects of aroP mutation

A transposon induced aroP mutant strain was isolated (see section 3.1.3) which enabled data to be obtained implicating the common aromatic transport system in having an effect on phenylalanine yield. The results are shown FIG. [15] which compares the kinetics of phenylalanine production in fermentor experiments of two strains; an aroP+ reference strain NST33 and an aroP::Tn10 mutant strain NST50. Both strains also carry aroF (FBI[r]) aroG (FBI[r]) tyrR[−] pheA (FBI[r]) pheO[c] tryA[−] and trpE[−] mutations.

As can be seen from FIG. [15] and Table 3.15, the aroP::Tn10 mutant strain NST50 shows a significant lower yield and also lower specific productivity than those for the aroP+ control strain.

TABLE 3.15

COMPARISON OF PHENYLALANINE OUTPUT[a]

| Strain | Relevant Genotype | Yield of phenylalanine at 24 h. Y p/x % (w/w) | Average q(phe) (g/g/h) |
|---|---|---|---|
| NST33 | aroP+ | 125 | 0.12 |
| NST50 | aroP− | 53 | 0.008 |

[a]Values are calculated from the data obtained by the experiment shown in FIG. 3.8.
[b]In addition to the genotype describerd in the table, both strains carry also aroF (FBI[r]) aroG (FBI[r]) tyrR[−]pheA (FBI[r]) pheO[c] tyrA[−] and trpE[−] mutations.

Interestingly, although the medium for both strains is the same, and formulated to give phosphate limitation of these strains at approximately 1.0 g dry weight per liter, the aroP::Tn10 strain NST50 grows to a higher cell density. These observations suggest that phosphate requirements of certain of these multiple-mutations strains are not efficiently utilized.

In other experiments, the aroP::Tn10 mutation was introduced into a phenylalanine hyperproducing strain NST57 that differed from strain NST33 in being tyrA+ trpE+. The resulting aroP− strain NST58 and its parental aroP+ strain NST57 were compared under conditions where final cell densities were limited by histidine in shaken flask cultures. As shown in Table 3.16, no great differences in phenylalanine yield were observed, either in the presence of tyrosine and tryptophan additions to the medium or in their absence. Thus it seems that the aroP effect is dependent on the presence of tyrA− and/or trpE− mutations.

TABLE 3.16

EFFECT OF aroP MUTATION ON PHENYLALANINE YIELDS IN SHAKEN FLASK CULTURES

| Strain | Relevant genotype[a] | Presence of tyrosine and tryptophan[b] | Yield of phenylalanine at 24 h. Y p/x % (w/w) |
|---|---|---|---|
| NST57 | aroP+ tyrA+ trpE+ | not added | 45 |
| | | present | 48 |
| NST58 | aroP− tyrA+ trpE+ | not added | 48 |
| | | present | 52 |

[a]In addition to the genotype describerd in the table, both strains carry also aroF (FBI[r]) aroG (FBI[r]) tyrR[−] pheA (FBI[r]) and pheO[c] mutations.
[b]Medium MMB - 20 g/l glucose was used and the concentrations of tyrosine and tryptophan supplemented in the medium were 0.05 mM and 0.2 mM, respectively.

CHAPTER 4

RESULTS PART II

FERMENTATION STUDIES

The studies reported in the previous chapter were concerned with describing genetic manipulation which was used to remove restrictions on phenylalanine biosynthesis, and with the role in hyperproduction of phenylalanine of individual mutation affecting various stages of phenylalanine biosynthesis.

The present chapter is concerned with investigation of the ptimal environmental conditions and medium formulation for phenylalanine production, together with a detailed analysis of process kinetics of both batch and continuous cultures.

To facilitate comparisons and to simplify interpretation of the results obtained, the experiments as much as possible were carried out with the same strain, namely strain NST37. The relevant biochemical and genetic characteristics of this multiple-mutation strain are shown diagrammatically in FIG. [16]. It can be seen from the diagram that the strain carries all the genetic modifications mentioned previously as being important in giving high phenylalanine yields, except that it does not carry any pheA plasmids.

The kinetics of phenylalanine overproduction by strain NST37 under controlled conditions in a 1 liter fermentor are illustrated in FIG. [17]. It was cultured so that the final cell density was limited by the phosphate content of the medium; the other nutrient requirements were in excess. The pH of the culture fluid was controlled at 7.0 with 2M NaOH solution. The initial glucose concentration was close to 20 g per liter. Since (i) this experiment shows that using this initial concentration of glucose avoids glucose depletion over a period of 30 hours of culture, and (ii) a later experiment (see FIGS. [21] and [22]) showed that glucose depletion reduces phenylalanine yields, unless otherwise noted, a similar initial glucose concentration was used for all the experiments described in this chapter.

As can be seen from the figure, a very significant proportion of metabolism by this strain has been diverted towards phenylalanine formation. Specific rates of product formation were high during exponential phase of growth [e.g. q(phenylalanine)=0.17 g/g/h] and fell during stationary phase; the highest value of yield per mass of substrate consumed (Y p/s) was obtained by allowing growth to stationary phase (at 124 hours culture time).

4.1 EFFECTS OF ENVIRONMENTAL CONDITIONS

4.1.1 pH

Preliminary experiments in shaken flasks (details not presented) were taken to suggest that the optimum pH for phenylalanine production was close to 6.5. This was later confirmed in more detailed continuous culture experiments (see section 4.5.2) and for most of the experiments presented in this chapter pH was controlled at a value of 6.5.

4.1.2 Temperature

An experiment to determine the temperature profile of strain NST37 was carried out using a 1 liter fermentor. The strain was grown in medium MMT3–20 g/l glucose at the variety of temperatures indicated in FIG. [18]. The cell density in the culture was limited to approximately 1 g of dry weight cells per liter of culture liquid by the phosphate content in the medium.

As can be seen from the figure, cell growth rate increases with increasing culture temperature; however, the highest phenylalanine yield per mass of cells (Y p/x) was achieved at the temperature of 33° C. At temperatures between 33° C. and 37° C., product formation decreases slightly but above 37° C. more significant decreases in phenylalanine output were obtained. At 41° C. phenylalanine production during stationary phase is severely inhibited, especially in comparison with the results obtained at lower temperatures.

To facilitate comparison of these fermentation runs, some relevant kinetic parameters have been calculated and presented in FIG. [19]. As can be seen from the figure, the optimal temperatures for the cell growth and for the product formation are not the same; the optimum temperature for cell growth is around 37° C. while that for phenylalanine production is around 33° C.

Results obtained by Tribe during studies of tryptophan production by mutants of *E. coli* (Tribe, 1976) give rise to the suggestion that temperature may affect overproduction of aromatic compounds by causing a greater rate of inactivation of the first enzyme of the common pathway DAHPsynthase. For example, Tribe found that the temperature optimum for production of tryptophan during stationary phase was relatively low (<30° C.), a period during which DAHP synthase activity is rapidly decaying.

But Tribe has not presented any direct evidence that the temperature effects described above are associated with alterations in the rate of formation of DAHP. As a simple means of obtaining such direct evidence, strain NST77 was constructed by introducing an aroB mutation into strain NST37. In strain NST77 two DAHP synthase isoenzymes (DAHP synthase Tyr and DAHP synthase Phe) are present to produce DAHP. Both isoenzymes in this strain are insensitive to feedback inhibition and their synthesis is also insensitive to repression control. However, because of the mutation in the aroB gene, this strain is unable to convert DAHP formed into 3-dehydroquinate, the second intermediate of the common pathway. Hence, assays of DAH(P) produced by this strain at various culture temperatures would provide a convenient way of estimating the in vivo rate of DAHP synthesis at different temperatures. (It should be noted that the assay procedure available does not distinguish between DAHP and the dephosphorylated form DAH, hence the notation DAH(P) for DAHP+DAH).

Strain NST77 was thus grown in MES buffer medium in shaken flasks at the variety of temperatures indicated in Table 4.1, and the yield of DAH(P) (Yp/x) was determined after 24 hours of culture.

TABLE 4.1

EFFECT OF TEMPERATURE ON DAH(P) YIELD OBTAINED WITH THE aroB⁻ STRAIN NST77 IN SHAKEN FLASK CULTURE[a]

| Culture temperature (°C.) | Cell mass (g/l) | DAH(P) produced (mg/l) | Yield at 24 hr Yp/x % (w/w) |
|---|---|---|---|
| 29 | 0.35 | 157 | 45 |
| 33 | 0.37 | 227 | 61 |
| 37 | 0.39 | 192 | 49 |
| 41 | 0.41 | 115 | 28 |

[a]The culture medium used was MES buffer medium; to 1 liter of 40 mM MES - 50 mM NaCl buffer (pH 6.9), 91.5 mg of $K_2SO_4$, 203 mg of $MgCl_2$ and 1.45 g of $NH_4Cl$ were supplemented.
The content of $K_2HPO_4$, the growth limiting factor was 76.6 mg per liter of the medium. The 3 aromatic amino acids and 3 aromatic vitamins (4-aminobenzoate, 4-hydroxybenzoate and 2,3-dehydroxybenzoate) were also added to the medium as specified in Table 2.3, Schedule 1.

As can be seen from the table, the profile for DAHP production by strain NST77 shows a similar temperature optimum to that for phenylalanine formation by strain NST37 (see FIG. [18] and FIG. [19]).

This experiment, taken together with the results shown in FIG. [18] and FIG. [19], provides evidence that the first reaction of the common pathway is sensitive to culture temperature and the data are consistent with the concept that during stationary phase the first reaction becomes a rate-limiting step in phenylalanine production.

4.2 MEDIUM FORMULATION FOR PHENYLALANINE HYPERPRODUCTION

4.2.1 Effect of Fe and Co ions

As mentioned earlier in section 3.3.4 in relation to the effect of the tonB mutation, excessive production of enterochelin is one potential problem in relation to phenylalanine hyperproduction (refer to Table 3.13). However, synthesis of the enzymes involved in enterochelin synthesis is repressible by the addition of excess ferric salt to growth media (McCray and Herrmann, 1976).

Hence the effect of adding various concentrations of ferric chloride to growth medium was investigated; the experiment was carried out by growing strain NST37 in shaken flasks for 24 hours. As shown in Table 4.2, in contrast to the findings with the tonB mutation there is no apparent iron effect on either cell growth or phenylalanine output over the range of ferric chloride concentrations tested.

TABLE 4.2

RELATION BETWEEN PHENYLALANINE YIELD AND IRON CONTENT OF THE CULTURE MEDIUM[a]

| $Fe^{+3}$ concentration (μmoles) | Cell mass (g/l) | Phe. formed (mg/l) | Yield at 24 hr. (Yp/x % w/w) |
|---|---|---|---|
| 0 | 0.46 | 317 | 69 |
| 50 | 0.47 | 315 | 67 |
| 100 | 0.49 | 328 | 67 |
| 200 | 0.47 | 328 | 70 |

[a]The growth medium used was MES buffer medium supplemented with different concentrations of ferric chloride as indicated in the table. Phosphate was used as the growth-limiting nutrient.

Since cobaltous ion is known to stabilize DAHP synthase activity in vitro (Camakaris, 1975), and it is clearly established as a co-factor for 3-dehydroquinate synthase activity (Srinivasan et al., 1963), the effect of adding a range of cobaltous chloride concentrations (5–400 μM $CoCl_2$) to culture medium was examined but no clear evidence was obtained that this parameter has any effect on phenylalanine yield (details not presented).

4.2.2 Effect of nitrogen

Nitrogen concentration in the culture medium would be expected to be an important parameter in production of a N-containing compound such as phenylalanine. Hence an experiment was designed for determining the effect of nitrogen on phenylalanine formation by strain NST37 using a range of $NH_4Cl$ concentrations.

Strain NST37 was grown in MES buffer medium (pH 6.9) supplemented with $NH_4Cl$ as indicated in Table 4.3, and the yield of phenylalanine was determined after culture for 24 hours in shaken flasks. The results obtained are given in Table 4.3.

TABLE 4.3

EFFECT OF $NH_4Cl$ CONCENTRATION ON FINAL CELL DENSITY AND PHENYLALANINE YIELD[a]

| Initial concentration of $NH_4Cl$ (mM)[a] | Theoretical cell yield[b] (g/l) | Cell Mass (g/l) | Phe formed (mg/l) | Yield at 24 h. (Yp/x % w/w) |
|---|---|---|---|---|
| 3.6 | 0.38 | 0.37 | 253 | 68 |
| 10.8 | 1.13 | 0.46 | 403 | 88 |
| 18.0 | 1.89 | 0.49 | 448 | 91 |
| 32.4 | 3.40 | 0.48 | 442 | 92 |
| 43.2 | 4.54 | 0.48 | 438 | 91 |

[a]Strain NST37 was grown in MES buffer medium (pH 6.9) with different concentrations of $NH_4Cl$ as indicated in the table at 37° C. in shaken flask cultures. The phosphate content of the medium was calculated to limit final cell density at approximately 0.5 g/l dry weight of cells.
[b]The values were calculated from the data for $NH_4^+$ yield coefficients obtained by Neidhardt et al. (1974).

It is clear from the data in Table 4.3 that nitrogen deficient condition results in a significant decrease in both cell density and phenylalanine formation. By comparing the values of Yp/x which corrects for differences in cell crop, it can be seen that an excess amount of nitrogen source favours phenylalanine production. These results were taken to indicate that $NH_4^+$ nitrogen supplied to culture medium for optimum yield has to be at least two-fold higher than the theoretical growth-supporting level of this nutrient.

No inhibitory effect on phenylalanine yield was evident from the data in Table 4.3 of excess $NH_4Cl$.

4.2.3 Effect of phosphate

Although no background information was available about the effect of phosphate on aromatic amino acid production, high concentrations of inorganic phosphate in culture medium usually have very critical effects on the production of various secondary metabolites such as production of antibiotics (Martin, 1977) and alkaloids (Robbers et al., 1972). Industrial production of many antibiotics is, therefore, carried out under phosphate limitation.

Hence an experiment to determine the phosphate effect on phenylalanine overproduction was carried out with strain NST37 using shaken flask cultures. The strain was cultured in MES buffer medium supplemented with a range of phosphate concentrations as shown in Table 4.4, and the yield of phenylalanine was determined after 24 hours culture.

TABLE 4.4

EFFECT OF PHOSPHATE CONCENTRATION ON PHENYLALANINE OUTPUT IN SHAKEN FLASK CULTURE[a]

| Initial concentration of $K_2HPO_4$ (m moles) | Theoretical cell yield (g/l) | Experimental cell crop (g/l) | Phe formed (mg/l) | Yield at 24 h (Yp/x % w/w) |
|---|---|---|---|---|
| 0.26 | 0.3 | 0.32 | 379 | 117 |
| 0.35 | 0.4 | 0.38 | 363 | 95 |
| 0.44 | 0.5 | 0.46 | 348 | 75 |
| 0.70 | 0.8 | 0.53 | 386 | 73 |
| 1.06 | 1.2 | 0.53 | 374 | 71 |

[a]Strain NST37 was cultured in MES buffer medium (pH 6.9) with different concentrations of $K_2HPO_4$ as indicated in the table at 37° in shaken flask cultures. Tyrosine content of the medium was calculated to limit final cell density at approximately 0.5 g/l dry weight of cells.
[b]Theoretical cell yields based on phosphate supplied were calculated from the data obtained by Neidhardt et al. (1974).

As can be seen from the table, high concentrations of phosphate have an inhibitory effect on phenylalanine production in that phenylalanine yield (Yp/x) increases significantly with decrease of phosphate concentration in the culture medium.

To confirm the phosphate effect obtained in shaken flask experiments, another set of experiments was carried out by growing strain NST37 in 1 liter fermentors at three different phosphate levels. The fermentation kinetics of these fermentor cultures are shown in FIG. [20], and phenylalanine yields per mass of cells determined after 30 hours culture of these fermentor runs are summarized in Table 4.5.

TABLE 4.5

RELATION BETWEEN PHOSPHATE CONTENT OF CULTURE MEDIUM AND PHENYLANINE YIELD, FROM PRIMARY DATA OF FIG. 4.5

| Final concentration of $K_2HPO_4$ (m moles) | Theoretical cell yield (g/l) | Experimental cell crop (g/l) | Phe formed (mg/l) | Yield at 30 h (Yp/x % w/w) |
|---|---|---|---|---|
| 0.66 | 0.75 | 0.64 | 925 | 145 |
| 0.87 | 0.99 | 0.74 | 1025 | 139 |
| 1.74 | 1.98 | 1.02 | 820 | 80 |

[a]The yields based on phosphate supplied were calculated from the data obtained by Neidhardt et al. (1974).

As can be seen from FIG. [20] and Table 4.5, the results obtained from 1 liter fermentor experiments are in agreement with those from shaken flask cultures, and suggest that excess phosphate inhibits phenylalanine formation.

4.2.4 Effect of glucose concentration

Glucose was the carbon source used for phenylalanine production, and since the major cost associated with media preparation is generally due to the carbon source, determination of the optimum concentration of glucose in fermentation medium is extremely important for establishment of an economic medium.

In order to define the effect of glucose concentration on phenylalanine formation, strain NST37 was grown in medium MMT3 supplemented with various concentrations of glucose. During the fermentation runs measurements of cell density, phenylalanine output, and residual glucose were made. The results are shown in FIG. [21] and FIG. [22]. It is clear from the figures that glucose limiting condition causes a significant arrest of both cell growth and phenylalanine formation. On the other hand, when growth is arrested under conditions where excess glucose is available; phenylalanine production continues to a greater extent; this is shown not only by the results in FIGS. [21] and [22], but also in several other experiments (e.g. see FIGS. [17], [23] and [26]). No noticeable inhibition of product formation by the presence of excess glucose in the medium is evident from the data shown in FIGS. [21] and [22].

To facilitate comparison of these fermentor runs, various kinetic parameters have been calculated and are presented in Table 4.6.

TABLE 4.6

KINETIC PARAMETERS OF STRAIN NST37 CULTURES AT DIFFERENT GLUCOSE CONCENTRATIONS, CALCULATED FROM THE DATA PRESENTED IN FIGS. 21 AND 22

| Kinetic parameter | Glucose concentration (%) | | | |
|---|---|---|---|---|
| | 0.45 | 0.90 | 1.35 | 1.80 |
| Specific growth rate; $\mu$ $(h^{-1})^a$ | 0.31 | 0.35 | 0.42 | 0.42 |
| Specific productivity; $q_p$ $(g/g/h)^a$ | 0.14 | 0.15 | 0.19 | 0.17 |
| Specific glucose uptake rate; $q_s$ $(g/g/h)^a$ | 1.65 | 1.36 | 1.61 | 1.57 |
| Cell yield;[b] $Y_{x/s}$ (g/g) | 0.20 | 0.14 | 0.13 | 0.12 |
| Product yield;[b] $Y_{p/s}$ (g/g) | 0.14 | 0.17 | 0.16 | 0.15 |
| Product yield;[b] $Y_{p/x}$ (g/g) | 0.74 | 1.33 | 1.38 | 1.36 |

[a]These parameters have been calculated for the exponential phase of cell growth.
[b]The values were obtained from the samples taken at 30 h. cultures.

As can be seen from the table, certain kinetic parameters, most notably phenylalanine yield per mass of cells (Yp/x) and also specific productivity (qp) and specific growth rate (μ) are significantly lower with the lower initial glucose concentrations than in the case where there is excess glucose throughout the fermentation.

4.2.5 Effect of tyrosine and tryptophan concentrations

As described earlier in section 3.3.3, mutational blockage of the tryptophan and tyrosine pathways in the phenylalanine overproduction strains gave increased phenylalanine yields even though the magnitude of the effect was not particularly great.

These trpE tyrA phenylalanine overproducing mutants require exogenous tryptophan and tyrosine for their growth. However, a priori it could be expected that an excess amount of these amino acids added to culture medium might cause an inhibitory effect on phenylalanine formation. It seemed appropriate, therefore, to establish the optimum concentrations of these two amino acids in the culture media for trpE tyrA mutant strains such as strain NST37.

Strain NST37 was cultured in shaken flasks in MES buffer medium supplemented with a range of tryptophan concentrations as shown in Table 4.7, and biomass and phenylalanine yield were determined after 24 hour culture at 37° C.

TABLE 4.7

EFFECT OF TRYPTOPHAN ON PHENYLALANINE YIELD IN SHAKEN FLASK CULTURES WITH STRAIN NST37[a]

| Final concentration of tryptophan (m moles) | Theoretical cell yield[b] (g/l) | Experimental cell crop (g/l) | phe formed (mg/l) | Yield at 24 h (Yp/x % w/w) |
|---|---|---|---|---|
| 0.02 | 0.4 | 0.44 | 309 | 70 |
| 0.03 | 0.6 | 0.46 | 360 | 78 |
| 0.04 | 0.8 | 0.46 | 361 | 78 |
| 0.07 | 1.4 | 0.45 | 344 | 76 |

TABLE 4.7-continued

EFFECT OF TRYPTOPHAN ON PHENYLALANINE YIELD IN SHAKEN FLASK CULTURES WITH STRAIN NST37[a]

| Final concentration of tryptophan (m moles) | Theoretical cell yield[b] (g/l) | Experimental cell crop (g/l) | phe formed (mg/l) | Yield at 24 h (Yp/x % w/w) |
|---|---|---|---|---|
| 0.11 | 2.2 | 0.45 | 329 | 73 |

[a]Strain NST37 was grown in MES buffer medium (pH. 6.9) supplemented with different concentrations of tryptophan as indicated in the table in shaken flasks. The tyrosine content of the medium (9.0 mg/l) was calculated to limit the final cell density at approximately 0.5 g/l dry weight of cells.
[b]The theoretically possible cell yields based on tryptophan supplied were calculated from the data obtained by Forrest and Walker (1970).

As can be seen from the table, excess tryptophan has no large effect on phenylalanine output, but the optimum tryptophan concentration for best product formation was found to be a slight excess over the minimal amount which is needed to support the cell crop obtained.

In another set of experiments, the effect of tyrosine on phenylalanine production was examined with the same strain under similar conditions to those used in examining tryptophan effects, except that in this case tryptophan was used as a growth-limiting nutrient. The results are presented in Table 4.8.

TABLE 4.8

EFFECT OF TYROSINE ON PHENYLALANINE OUTPUT IN SHAKEN FLASK CULTURES WITH STRAIN NST37[a]

| Final concentration of tyrosine (m moles) | Theoretical cell yield[b] (g/l) | Experimental cell crop (g/l) | phe formed (mg/l) | Yield at 24 h (Yp/x % w/w) |
|---|---|---|---|---|
| 0.045 | 0.45 | 0.46 | 323 | 70 |
| 0.070 | 0.69 | 0.49 | 388 | 79 |
| 0.095 | 0.94 | 0.50 | 389 | 78 |
| 0.150 | 1.49 | 0.49 | 356 | 73 |
| 0.300 | 2.97 | 0.51 | 334 | 65 |

[a]Culture conditions were similar to those described in footnotes to Table 4.7 except that in these experiments tryptophan was used as a growth-limiting nutrient. The tryptophan concentration in the medium (4.4 mg/l) was calculated to limit the final cell density at 0.5 g/l dry weight of cells.
[b]The yields based on tyrosine supplied were calculated from the data obtained by Forrest and Walker (1970).

As shown in the table, tyrosine shows a similar pattern to that observed in the previous experiment with tryptophan in that the optimum tyrosine concentration was found also to be slightly in excess of the minimum amount which is required to support the actual cell growth. There is also evidence that some inhibition of product formation occurs at the two highest tyrosine concentrations.

4.3 PHYSIOLOGICAL PARAMETERS RELATING TO PHENYLALANINE FORMATION

As discussed earlier, in chapter 1, the first reaction of the common pathway catalysed by DAHP synthases, and the first and second reactions of the phenylalanine pathway carried out by chorismate mutase-p-prephenate dehydratase are the key control points in phenylalanine biosynthesis in E. coli. Hence, changes of these two enzyme activities during cultivation of phenylalanine producing strains might have a direct relation to rate of phenylalanine formation.

A 5 liter fermentor experiment with strain NST37 was carried out to examine changes in specific activities of these two enzymes during the fermentation run, so as to enable correlation of any changes in the specific activity of these enzymes with changes in the rate of phenylalanine production (see FIG. [23]).

Somewhat surprisingly, although in this strain repression control is non-functional due to a tyrR⁻ mutation, DAHP synthase specific activity rises during exponential phase of growth reaching its maximum value at about 16 h of culture. The reason for this rate in specific activity is not fully understood and has not yet been further investigated. After 16 h of culture, DAHP synthase specific activity falls significantly, with an apparent half-life of approximately 23 h. This is much longer than the half-life observed by Tribe (1976) which was close to 5 h, but the relevant difference is that Tribe's experiments were carried out at 37° C. as compared to the present experiments carried out at 33° C. These changes in half-life of DAHP synthase specific activity are considered to be sufficiently great to play an important role in the kinetics of phenylalanine formation. On the other hand, prephenate dehydratase specific activity is much less variable (see FIG. [23], and was found to remain relatively unchanged during stationary phase of growth. It should also be noted that in stationary phase there is a progressively decreasing rate of phenylalanine formation correlating with the decline in DAHP synthase levels.

Another finding from this experiment is a significant increase in the phenylalanine yield compared to the earlier experiments. This can be seen by referring to Table 4.9 in which the kinetics of strain NST37 cultured in a 5 liter fermentor are compared with that of strain NST37 grown in a 1 liter fermentor.

TABLE 4.9

COMPARISON OF KINETIC PARAMETERS OBTAINED IN DIFFERENT FERMENTOR EXPERIMENTS

| Kinetic parameter | 1l-fermentor[a] | 5l-fermentor |
|---|---|---|
| Specific growth rate; $\mu$ (h$^{-1}$) | 0.433 | 0.583 |
| Specific productivity; qp (g/g/h) | 0.230 | 0.250 |
| Yield; Yp/s (g/g)[b] | 0.158 | 0.163 |
| Yield; Yp/x (g/g)[b] | 1.49 | 2.11 |

[a]The values for the 1 litre fermentor run were calculated from the data obtained with strain NST37 cultured under the optimal conditions examined so far (refer to the values obtained at 33° C. in FIG. [18]).
[b]Phenylalanine yields were obtained from the samples taken after 30 hours culture.

As can be seen from the table, specific growth rate, specific productivity and phenylalanine yield per mass of substrate consumed in the process run in the 5 liter fermentor are all slightly higher than those of the 1 liter fermentor culture, while phenylalanine yield per mass of cells shows an even greater increase in the 5 liter fermentor culture. One of the factors causing this effect on phenylalanine production may be that the 5 liter fermentor has a much better gas transfer ability compared to the small fermentor although oxygen probes indicated similar dissolved oxygen tension in both cases. Proper evaluation of the cause of this improvement in process yield requires further experimentation.

4.4 EVALUATION OF PROCESS PRODUCTIVITY AND YIELD IN BATCH CULTURES

4.4.1 Kinetics of phenylalanine production with strain NST70 in batch culture FIG. [24] shows the main findings of an experiment which was carried out in an attempt to evaluate the phenylalanine productivity and yield coefficients in terms of Yp/x and Yp/s with strain NST70, one of the best yielding multiple-mutation strains.

The strain NST70 used for this experiment, differs from the strain NST37 in having additional copies of pheA (FBI$^r$) genes borne by the plasmid pUNT21 as described in the previous chapter (see section 3.2.2 and section 3.3.5).

The cells were grown in medium MMT3-20 g/l glucose at 33° C. in a 1 liter fermentor, and the pH was controlled at 6.5 by feeding 2M NaOH solution. Phosphate was supplemented to the culture medium at a concentration calculated to be limiting to the cell crop at approximately 0.7 g/l dry weight of cells and the other nutrient requirements to be supporting at values well in excess of this.

Some key kinetic parameters of the fermentor run with strain NST70 have been calculated and compared with corresponding values for strain NST37 grown under the same conditions (see Table 4.10).

TABLE 4.10

COMPARISON OF KINETIC PARAMETERS OF STRAIN NST70 AND STRAIN NST37 GROWN IN A 1 LITRE FERMENTOR[a]

| Kinetic parameter | Strain NST37[b] | Strain NST70 |
|---|---|---|
| Specific growth rate $\mu$ (h$^{-1}$) | 0.433 | 0.450 |
| Specific productivity qp (g/g/h) | 0.230 | 0.223 |
| Yield[c] Yp/s (g/g) | 0.158 | 0.123 |
| Yield[c] Yp/x (g/g) | 1.49 | 1.69 |

[a]Details of the culture conditions for strain NST70 are given in the text.
[b]The kinetic parameters of strain NST37 shown in the table were calculated from the data obtained from the 1 litre fermentor run operated under the same conditions as those with strain NST70.
[c]Phenylalanine yield coefficients were obtained from the samples taken at 30 hours.

As can be seen from the table, there are no significant differences between the two strains in the values of specific growth rate, specific productivity and phenylalanine yield per mass of glucose consumed, but the yield coefficient per mass of cells for strain NST70 is somewhat higher than that for strain NST37. Overall, the plasmid bearing strain NST70 appears to offer only slight potential for an improvement in the process.

4.4.2 Increase in phenylalanine yield by increasing biomass

The general information obtained from the fermentor experiments presented so far shows that overall levels of phenylalanine in the fermentation broth are considerably influenced by the concentration of biomass in the fermentor. Therefore, one of the most important approaches to enhance the yield of phenylalanine would seem to be an investigation of how to achieve much higher final cell densities in culture fluids while still maintaining efficient phenylalanine production.

Preliminary experiments with strain NST37, however, showed that the growth of cells ceased at a cell density of approximately 2.0 g/l dry weight of cells in the presence of an excess of all the nutrient requirements for the cell growth (data not presented). In these experiments there was no evidence that limitation of either glucose or essential inorganic nutrients or dissolved oxygen levels was causing the growth stasis. Similar results were also observed with other phenylalanine overproducing strains carrying tyrA trpE mutations. The reason for this growth stasis was not fully investigated but the defect in cell growth with strain NST37 and other auxotrophic strains examined seemed likely to be related to the uptake of the required amino acids, namely tyrosine and tryptophan. Hence a tyrA+ trpE+ derivative of strain NST37 was constructed and designated as strain NST74.

In a preliminary experiment, strain NST74 gave a similar cell crop in minimal media as given by a wild-type E. coli strain, thus avoiding some of the difficulties encountered with strain NST37 by allowing higher cell densities to be obtained in fermentor experiments. Another big advantage with using strain NST74 lies in the fact that especially in a large scale industrial process it is much better if relatively expensive nutrient requirements of tyrA− trpE− auxotrophs do not have to be added to the culture medium. Furthermore, although mutational blockages of tyrosine and tryptophan pathways in the phenylananine overproducing strains do enhance the yield of this amino acid, the wastage of chorismate down these pathways is, fortunately, of minor quantitative significance (as discussed earlier in section 3.3.3).

It also should be added that for technical reasons it is difficult to convert a tyrA+ trpE+ strain to a tyrA− trpE− but a simple matter to convert a tyrA− trpE− mutant to a tyrA+ trpE+ strain. This is one further reason that initial work was carried out with the tyrA− trpE− strains.

Hence, a 1 liter fermentor experiment was carried out using the tyra+ trpE+ strain NST74, to obtain fundamental data on the strain and as a preliminary to later experiments with this strain involving batch and continuous culture at higher cell densities.

The cells were grown at 33° C. in medium MMT4 supplemented with 15.6 g/l of glucose and 0.1 mg of thiamine per liter. The pH of the culture broth was controlled to 6.5 with 2M NaOH solution. Phosphate was added to the culture medium at a concentration calculated to be limiting to cell crop at approximately 1.5 g dry weight of cells per liter of culture fluid.

As can be seen from FIG. [25] and by comparison with earlier results (see FIG. [17]), the kinetics of phenylalanine production with strain NST74 follow a similar pattern to those given by the tyrA− trpE− phenylalanine overproducing strains examined previously.

Another feature of this experiment is the concurrent excretion of tyrosine and tryptophan into the culture fluids by strain NST74. In this strain, the tyrosine terminal pathway enzymes are derepressed due to the presence of a tyrR mutation. Hence it is not surprising that some tyrosine is produced by the strain. However (refer again to FIG. [25]), the level of tyrosine produced by the strain is quantitatively unimportant in that it corresponds to approximately 4% of the phenylalanine yield. Tryptophan production was even less significant and was scarcely detected (results not presented).

A comparison of kinetic parameters calculated from the data of FIG. [25] and those for strain NST37 is presented in Table 4.11.

TABLE 4.11

COMPARISON OF KINETIC PARAMETERS OF STRAIN NST 74 AND STRAIN NST37 GROWN IN 1 LITRE FERMENTORS

| Kinetic[b] parameter | Strain | |
|---|---|---|
| | NST37[a] | NST74 |
| Specific growth rate $\mu$ (h$^{-1}$) | 0.43 | 0.47 |
| Specific productivity qp (g/g/h) | 0.23 | 0.12 |
| Phenylalanine yield Yp/s (g/g) | 0.158 | 0.151 |
| Phenylalanine yield Yp/x (g/g) | 1.49 | 1.37 |
| Final cell density (g/l) | 0.81 | 1.45 |
| Maximum phenylalanine concentration (g/l) | 1.21 | 1.98 |

[a]The kinetic parameters of strain NST37 were calculated from the data obtained under the optimal conditions examined so far (refer to the values obtained at 33° C. in FIG. [18]).
[b]The values of specific growth rate and specific productivity were calculated for the exponential phase of cell growth, while the other parameters in the table were obtained from the samples taken at 30 h of culture.

As shown in Table 4.11, phenylalanine yield and also phenylalanine productivity with strain NST74 are slightly lower than those values for strain NST37. However final cell crop and phenylalanine concentration are higher with strain NST74, emphasising the advantage of using strain NST74.

Next, an experiment for further improving phenylalanine productivity and product concentration through a fermentation process at much higher cell densities, strain NST74 was cultured at 33° C. in medium MMT12-30 g/l initial glucose in a 5 liter fermentor. To minimize initial concentrations of possibly inhibitory substrates, supplements were added to the medium as indicated in the legend to FIG. [26]. The initial phosphate concentration was 0.7 g of K$_2$HPO$_4$ per liter of medium and a further supplement was made with 0.27 g of K$_2$HPO$_4$ per liter at 11 hours culture time. Hence the total phosphate concentration is estimated to have a growth supporting ability of approximately 12 g dry weight of cells per liter of culture broth.

As shown in FIG. [26] maximum cell density of 8.1 dry weight of cells per liter of culture broth was obtained after 19 hours culture; very much higher phenylalanine concentrations (10.9 g/l) were obtained than in previous experiments at lower final cell densities. In Table 4.12 is shown a comparison of the yield values and kinetic parameters from the 1 liter fermentor and those for the 5 liter fermentor experiment at higher cell density.

TABLE 4.12

COMPARISON OF KINETIC PARAMETERS OF STRAIN NST74 CULTURED AT DIFFERENT CELL DENSITIES IN THE FERMENTOR

| Kinetic parameter | Culture Condition | |
|---|---|---|
| | At lower cell density (1l-fermentor)[a] | At higher cell density (5l-fermentor)[a] |
| Maximum cell mass (g/l) | 1.45 | 8.1 |
| Maximum phenylalanine concentration (g/l) | 1.98 | 10.9 |
| Specific growth rate[b] $\mu$ (h$^{-1}$) | 0.47 | 0.45 |
| Specific productivity[b] qp (g/g/h) | 0.12 | 0.09 |
| Yield[c] | 1.37 | 1.38 |

TABLE 4.12-continued
COMPARISON OF KINETIC PARAMETERS OF STRAIN NST74 CULTURED AT DIFFERENT CELL DENSITIES IN THE FERMENTOR

| Kinetic parameter | Culture Condition | |
|---|---|---|
| | At lower cell density (1l-fermentor)[a] | At higher cell density (5l-fermentor)[a] |
| Yp/x (g/g) | | |

[a] Kinetic parameters of the 1 litre fermentor run were calculated from the results shown in FIG. [26], and for the 5 litre fermentor run from the results shown in FIG. 4.11.
[b] The values were calculated for the exponential phase of cell growth.
[c] Phenylalanine yield was obtained from the samples taken after 30 hours culture.

As can be seen from the table, there is little change in the values of specific growth rate, specific productivity, and phenylalanine yield per mass of cells compared to the values obtained from the 1 liter fermentor experiment.

It should be noted, however, that glucose depletion occurred after 30 hours cultivation. This might have caused a significant decrease in final phenylalanine concentration if the substrate effects examined in section 4.2.4 are taken into account. Hence further experimentation along these lines would be expected to result in a higher final phenylalanine concentration.

4.5 INVESTIGATION OF CONTINUOUS CULTURE

4.5.1 Continuous culture at lower cell densities

One of the basic observations made during the batch culture studies is that the highest rate of phenylalanine formation was approached during the transition period from exponential to stationary phase of growth, after which it exhibited a decline. A means for prolonging this active phase would be expected to give a far greater productivity, and it was anticipated that this could be achieved by exploiting the potential of the continuous culture process. This mode of process operation is particularly well suited to exploit the potential for higher productivity of a growth associated (or partially growth associated) process especially with fast growing cells (as discussed by Aiba et al., 1973).

Hence as an initial experiment continuous culture with strain NST74 was carried out in a 1 liter fermentor with details as described in the legend to FIG. [27]. Phosphate was chosen as the growth-limiting nutrient in this experiment.

To ensure steady-state conditions, at least six changes of medium were allowed at all growth rates before samples were taken. After reaching steady-states at various dilution rates, cell density, phenylalanine, glucose and phosphate content were measured, and the results are shown in FIG. [27].

It should be noted that this experiment involved 14 days of continuous culture at the dilution rates from 0.05 ($h^{-1}$) to 0.3($h^{-1}$) as indicated in FIG. [27]. After this time interval the dilution rate of the culture was adjusted back to the starting rate of 0.05 $h^{-1}$. Cell density and phenylalanine level of the sample taken after reaching steady-state were then determined, and found to be essentially the same as the values obtained at the first dilution rate. This observation clearly shows that conditions can be devised to maintain the multiple-mutation strain used in this experiment as a high yielding culture in continuous culture for an extended period.

As can be seen from the figure, biomass and especially phenylalanine levels are dependent on the dilution rate. Perhaps the most important general comment that can be made about this experiment is that much higher phenylalanine concentrations can be obtained at lower dilution rates.

Phenylalanine productivity, specific phenylalanine production rate (qp), phenylalanine yield per mass of substrate (Yp/s), and biomass yield (Y) were calculated at each dilution rate and plotted as a function of specific growth rate; the results of these calculations are shown in FIG. [28]. As shown in this figure, maximum productivity of 0.148 (g/l/h) was observed at the dilution rate of 0.1 $h^{-1}$ while maximum specific productivity of 0.142 (g/g/h) was obtained at 0.2 $h^{-1}$ dilution rate. It is also worth noting that phenylalanine yield per mass of glucose consumed (Yp/s) was relatively independent to the specific growth rates and was an average value of 0.151 (g/g), although this inference is more obvious from the results of a later experiment (see FIG. [30]). On the other hand, the biomass yield per mass of glucose consumed (Yx/s) increases with the increase in the growth rate, and this is likely to be due to the decrease in the relative contribution of maintenance metabolism at higher growth rates.

Changes in substrate metabolism by strain NST74 at different growth rates can be best assessed by referring to FIG. [29], which gives the relation between rate of glucose consumption (qs), biomass yield (Yx/s) and growth rate for strain NST74 in the continuous culture experiment. Also shown on the figure are data for comparative purposes with a wild-type control strain, namely strain NST109.

The biomass yields (Yx/s) and the specific glucose uptake rates for strain NST109 were obtained from a phosphate-limited chemostat culture in the same medium and unde- the same conditions as those for strain NST74 described in the legend to FIG. [27]. Unlike strain NST74, strain NST109 carries wild-type aroF, aroG, pheO, pheA and tyrR genes, and does not excrete a detectable amount of phenylalanine or other aromatic amino acids into the culture medium.

As can be seen from the figure, the biomass yields for both strains vary in a similar fashion with growth rates but the values for strain NST74 are consistently lower than those for the reference strain at all dilution rates examined. This difference in yield is due to the fact that the specific glucose uptake rates for strain NST74 are consistently higher than those for the reference strain.

By assuming that glucose consumption by strain NST74 for biomass formation, it is possible to calculate a phenylalanine yield coefficient corrected for glucose utilization for biomass (Yp/s') using the equation shown in Section 2.16 (p. 76). The resulting corrected yield coefficient is also plotted in FIG. [29]. It can be seen from the figure that the yield coefficient values at higher dilution rates are close to 1 (g/g), and illustrate that glucose is extremely efficiently converted to phenylalanine by the strain NST74.

It should be mentioned that the determination of maintenance coefficient (m) by, for example, extrapolating a plot of specific glucose uptake rate (qs) against specific growth rate ($\mu$) to find the value at $\mu=0$ (Abbott et al., 1974; Pirt, 1975) seems to have little physiological meaning since for this experiment it was carried out using phosphate limitation and carbon excess. A detailed discussion of the difficulty in interpreting such data in terms of simple maintenance energy concepts has been provided by Tempest (1978).

Another continuous culture experiment with strain NST74 was carried out using higher concentration of the growth-limiting nutrient (phosphate) in a medium reformulated to support higher cell densities, concentrating on the lower range of dilution rates since these would clearly be expected to have more potential for giving higher phenylalanine concentrations and thus minimize the costs of product recovery and purification.

After allowing for steady-states to be achieved at various dilution rates, measurements were again made of cell mass, phenylalanine, glucose and inorganic phosphate. The results of these measurements and values for various kinetic parameters calculated are given in FIG. [30]. The results obtained by this experiment confirm the general observations made in the previous experiment (see FIG. 27 and FIG. [28]). For example, phenylalanine concentrations are higher at lower dilution rates, there is agreement between the values for yield coefficients, and rates of product formation are similar in the range of dilution rates where data are available from both experiments. The cell densities obtained from the experiment described in FIG. [30] were approximately 1.7-fold higher than those from the previous experiment, and maximum values for phenylalanine concentration were 1.8-fold higher.

4.5.2 Effect of pH.

Preliminary results (refer to section 4.1.1) suggested that the pH value of the growth environment affected cell growth and phenylalanine yield significantly. Hence the effect of pH values on phenylalanine production in a continuous culture process was investigated, using strain NST74 and a dilution rate of 0.1 $h^{-1}$.

The cells were grown in medium MMT3-15 g/l glucose in a chemostat using phosphate as the growth-limiting nutrient. After allowing for steady-states to be achieved at various pH values indicated in FIG. [31], measurements were made of cell density, phenylalanine and residual glucose. As can be seen from FIG. [31], maximum cell growth and phenylalanine levels were observed at pH 7.5, but phenylalanine yield per mass of cells was found to be highest value at pH 6.5. At pH values lower than 6.5 or higher than 7.5 a significant decrease in cell growth and phenylalanine formation was observed. Clearly, control of the pH of the culture broth is a most important parameter in phenylalanine formation.

4.5.3 Continuous culture at higher cell densities

The previous batch experiment at higher cell densities revealed that overall levels of phenylalanine in the culture fluid were closely proportional to cell mass up to the final cell density of 8.1 g per liter (refer to section 4.4.2). Hence, similar improvements in phenylalanine yields in continuous culture were sought by operation at higher cell densities in continuous culture.

It should be noted that the 1 liter fermentors used for certain previous experiments are, because of their limited agitation capacity, not well suited for culture of cells to high cell density. Hence, for this experiment a 5 liter fermentor was used. Strain NST74 was cultured using a medium with increased concentrations of nutrients over those used previously but still designed to ensure that phosphate would be the most limiting nutrient (for details see legend to FIG. [32]. A dilution rate of 0.05 $h^{-1}$ and a temperature of 33° C. were chosen, hopefully to maximize phenylalanine concentrations. The experiment was run for 8.5 days and measurements of cell mass, phenylalanine, glucose and inorganic phosphate were made at 24 hour intervals. The results of these measurements are given in FIG. [32]), and they show that very little deterioration of process performance occurs in this extended period of operation.

TABLE 4.13

COMPARISON OF KEY PROCESS PARAMETERS CALCULATED FOR DIFFERENT CONTINUOUS CULTURE EXPERIMENTS

| Experiment[a] | Dilution rate ($h^{-1}$) | Cell mass (g/l) | Phenyl-alanine formed (g/l) | Productivity (g/l/h) | $q_p$ (g/g/h) | $q_s$ (g/g/h) | Yield (Yp/s) (g/g) | Biomass yield (Yx/s) (g/g) | Yield (Yp/x) (g/g) | Residual $K_2HPO_4$ concentration (mg/l) |
|---|---|---|---|---|---|---|---|---|---|---|
| Experiment I | 0.05 | 1.26 | 2.2 | 0.11 | 0.09 | 0.53 | 0.17 | 0.09 | 1.76 | 1.6 |
| Experiment II | 0.05 | 2.23 | 4.0 | 0.20 | 0.09 | 0.50 | 0.18 | 0.10 | 1.79 | 0.8 |
| Experiment III | 0.05 | 5.90 | 8.2 | 0.41 | 0.07 | 0.39 | 0.18 | 0.13 | 1.39 | 8.5 |

[a]Experiment I is the continuous culture shown in FIG. [27], Experiment II the continuous culture shown in FIG. [30], and Experiment III the continuous culture at higher cell density shown in FIG. [32].

Further assessment of this experiment can be made by comparison of key parameters with those obtained in the earlier continuous culture experiment and by referring to Table 4.13.

The main point that emerges from this table is that although operating with higher levels of phosphate in the medium, higher biomass, and phenylalanine levels and greater process productivity are obtained. The parameters which make allowance for differences in biomass level such as specific productivity (qp) and yield (Yp/x) do not change greatly. In experiment III, specific productivity (qp), specific glucose consumption (qs) and Yp/s are marginally depressed. This is possibly due to the fact that at the higher cell densities phosphate was not fully utilized in this experiment and growth was probably subject to limitation by byproduct inhibition.

CHAPTER 5

GENERAL DISCUSSION

5.1 FINDINGS WITH REGARD TO GENETIC MANIPULATIONS OF THE PHENYLALANINE METABOLISM

In this study genetic manipulation of both the common pathway of aromatic biosynthesis and the phenylalanine terminal pathway have been shown to be important, and the major finding is that best phenylalanine yields are obtained in multiple-mutation strains with both common and terminal pathway controls abolished.

The role of the common pathway reactions is illustrated by the effects on phenylalanine yield of cellular DAHP synthase isoenzyme content even in strains having, due to abolition of repression, high levels of feedback inhibition desensitized enzymes (see Table 3.9), and also by the ten-fold increase in yield observed with the introduction of the tyrR mutation, which causes derepression of the synthesis of these isoenzymes (see Table 3.10) as well as affecting shikimate kinase levels and other enzymes . . . .

The previous reports concerning tryptophan hyperproducing mutants of E. coli contain findings that are quite pertinent to interpretation of these effects (Tribe, 1976; Tribe and Pittard, 1979). In that study, DAHP synthase activity was shown to be markedly unstable during stationary phase of growth, and this instability was indicated as having a major effect on the kinetics of tryptophan production. Although in tyrR mutants during exponential phase of growth levels of DAHP synthase Tyr isoenzyme were greater than DAHP synthase Phe isoenzyme levels, the Phe isoenzyme was found by Tribe to be significantly more stable than the Tyr isoenzyme during stationary phase. This may explain the observations reported in section 3.3.1 (refer again to Table 3.9) showing that the Phe isoenzyme apparently has greater effect on phenylalanine yield than the Tyr isoenzyme. The instability of DAHP synthase is also relevant to the observations shown in FIG. [13] and FIG. [15] that rate of phenylanine output [q(phenylalanine)] is much lower during stationary phase than during exponential phase of growth. This feature is confirmed (i) by a fermentor experiment (refer to FIG. [23]), showing that the specific activity of DAHP synthase from strain NST37 falls markedly from the beginning of stationary phase, while prephenate dehydratase activity appears to be much more stable, and (ii) by the general observation in several fermentor experiments described in chapter 4 of declining values of q(phe) in stationary phase of growth (see e.g. FIG. [17]).

The other major effect on phenylalanine yield found in this work is, not surprisingly, the removal of phenylalanine terminal pathway controls (see Table 3.9 and Table 3.11). A great increase in phenylalanine yield was achieved when mutations in the genes responsible for the activities of the common pathway enzymes [aroF (FBI$^r$) aroG (FBI$^r$) tyrR$^-$] were combined with the alterations in the phenylalanine specific pathway controls [pheO$^c$ and pheA (FBI$^r$)], as can be seen from the fact that yields were greater from the strains of Table 3.9 compared to those from Table 3.11.

Wastage of chorismate down the tryptophan and tyrosine pathways was of lesser quantitative significance (see Table 3.12), although a more pronounced effect, presumably due to diversion of chorismate to enterochelin formation, was found with the tonB mutation (see Table 3.13). In spite of this, levels of iron salts added to the medium of tonB$^+$ strains (see Table 4.2) do not seem to have a critical effect on phenylalanine production, suggesting that only extreme conditions of iron starvation such as occurring with a tonB$^-$ mutant are sufficient to divert chorismate away from phenylalanine formation.

The finding of only small effects of the mutations tyrA$^-$ and trpE$^-$ is fortunate since in a large-scale industrial process it would be far better if relatively expensive nutrient requirements of tyrA$^-$ trpE$^-$ auxotrophs do not have to be added to the culture medium. On the other hand the unblocked strains produced significant amounts of tyrosine, probably adding to the costs of phenylalanine purification. Blockage mutations were found to be far more critical in Tribe's study of tryptophan production, in that a tryptophan overproducing strain carrying intact phenylalanine and tyrosine pathways genes was reported to give less than one third of the tryptophan yield (as Yp/x % w/w at 15 h) obtained by a mutant which had the same genetic characteristics except in the presence of blocks in both the branch pathways (Tribe, 1976; Tribe and Pittard, 1979).

The relationship between phenylalanine enzyme content and phenylalanine yield was examined in two different series of experiments, the results of which have been re-presented in a graphical form in FIGS. [33] and [34]. FIG. [33] shows the relationship for a series of strains with wild-type regulation of the common pathway, and FIG. [34] shows the relationship for strains in which there is a considerable increase in capacity for chorismate supply because of removal of repression and inhibition controls acting on the common pathway. In the second figure an approximately linear relationship between enzyme level and phenylalanine yield is valid up to much higher phenylalanine yields than those obtained in the former figure, and this is interpreted to mean that in the former situation, because of inhibition and repression of DAHP synthase, DAHP synthesis limits phenylalanine output at a rather low value. Even in FIG. [34], however, there is some evidence that DAHP synthesis may be limiting output with the ColE-pheA plasmid strain. (It should be noted that in FIG. [33] the enzyme levels shown on horizontal axis are those found in the presence of 1 mM phenylalanine added to the reaction mixtue in order to allow comparison of feedback inhibition resistant and feedback inhibition sensitive strains on the one figure). Hence, it seems most likely that even further increase in the level of DAHP synthase desensitized to feedback inhibition can offer advantages in terms of phenylalanine productivity, although there is no direct evidence for this at the present stage with the phenylalanine overproducing strains.

In a similar vein, it would seem useful also to evaluate whether the cellular content of aminotransferase, the enzyme in the phenylalanine terminal pathway which is responsible for the amination of phenylpyruvate, is sufficient to accommodate the considerable increase in CMP-PDH activities in these phenylalanine hyperproducing strains.

Although results obtained with the multi-copy plasmid, pUNT21, clearly show that it had been generated by a gene-conversion event as an altered form of plasmid pMU307, and that the plasmid pUNT21 has a definite effect of increasing phenylalanine yield in multiple-mutation strains (Table 3.4, FIG. [34], and FIG. [24]), the experiments which have been done with this plasmid should be regarded as preliminary, since there is still some uncertainty as to (i) whether it carries the pheO$^c$ mutations, (ii) how many copies/cell of the plasmid are present in a growing culture, and (iii) the stability of the plasmid in this system. Further more detailed studies are necessary to evaluate these questions.

It is difficult at present to draw an entirely satisfactory explanation of the phenomena observed with the aroP mutants. These include (i) the great difference in phenylalanine yield between the aroP$^+$ and the aroP$^-$ strain (see FIG. [15] and Table 3.15), (ii) the difference between the strains in efficiency of utilization of auxotrophic requirement and thus yield of biomass (see FIG. [15]), (iii) the dependence of the effect brought about by the aroP$^-$ mutation on the presence of tyrA or trpE mutations (see Table 3.16). One plausible hypothesis is as follows: phenylalanine production is proposed per se to interfere with efficient utilization of exogenous tyrosine (or tryptophan) by auxotrophs by drawing off amino nitrogen via the transamination, converting the amino acids to the keto acid form (p-hydroxyphenylpyruvate is poorly utilized by tyrosine auxotrophs; D. Tribe, personal communication). It is also proposed that the common transport system specified by aroP has a major role in efflux of phenylalanine from the cell, and that the primary effect of aroP⁻ is to interfere with phenylalanine efflux. The secondary effects of this are reduced phenylalanine synthesis and more efficient utilization of exogenous tyrosine and tryptophan. The problem, however, with this hypothesis is that additional assumptions are needed to explain why the aroP effect on yield of phenylalanine is dependent on the presence of trpE⁻/tyrA⁻ mutations.

A report, perhaps relevant to this problem, on tyrosine- and phenylalanine-specific transport systems, has indicated that the transport mutants carrying the tyrP and pheP alleles had higher levels of DAHP synthase Tyr than the parent strain carrying wild-type tyrP⁺ and pheP⁺ genes, and these mutants showed the ability to excrete the respective amino acids. The cross-feeding of auxotrophs requiring either tyrosine or phenylalanine was reported to be very specific and corresponding with the loss of the relevant specific transport system (Whipp et al., 1980). Also in the studies on tryptophan overproduction with mutants of *E. coli*, the introduction of a mutation causing a defect in the constitutive tryptophan specific transport system into tryptophan overproducing strains, was reported to have produced significantly more tryptophan (Tribe, 1976). It is also interesting to note that lysine efflux in lysine producing mutant of *B. lactofermentum* was reported to be due to active transport which enables the efflux of lysine against the 5-fold higher concentration of lysine in the medium compared with the intracellular concentration (cited by Nakayama, 1976). Hence, together with further investigation on the aroP mutation, it seems to be worth while to define the effects of the alteration of the phenylalanine-specific transport system on the product formation with phenylalanine hyperproducing strains using pheP mutations.

5.2 STUDIES ON ENVIRONMENTAL CONDITIONS AND MEDIUM FORMULATION FOR THE FERMENTATION PROCESS

5.2.1 Environmental conditions

The optimum pH for phenylalanine overproduction was determined using one of the higher yielding multiple-mutation strains with a continuous culture process in a 1 liter fermentor. It was found from the results obtained from the experiment that the production of phenylalanine is strongly dependent on the pH of the culture broth (see FIG. [31]). The optimum pH for cell growth and for phenylalanine formation was 7.5, but maximum yield value per mass of cells (Yp/x) was obtained at 6.5. Considering that both process productivity and the final product concentration in the culture fluids are important criteria for process evaluation, the most economic pH value for phenylalanine fermentation would probably be an intermediate value, around 7.0.

Next, it was established that the optimum temperature for the production of phenylalanine was close to 33° C. (see FIG. [19] and that this was distinctly different from the temperature optimum for growth, which was 37° C. An additional experiment (see Table 4.1) gave support to the concept that the temperature optimum for phenylalanine formation was largely determined by DAHP synthase instability at higher temperatures. In this experiment an aroB⁻ strain was used for estimation of the relative rate of DAHP synthesis in vivo at different temperatures and this was found to have a similar temperature profile to phenylalanine formation. Additionally, in another experiment, a direct measurement was made of the half-life of DAHP synthase activity in stationary phase culture at a temperature of 33° C. (see FIG. [23]), and values were significantly greater than those obtained by Tribe at temperature of 37° C. (Tribe, 1976; Tribe and Pittard, 1979).

Similar temperature effects on tryptophan overproduction by mutants of *E. coli* have been reported; for example, the temperature optimum for production of tryptophan during stationary phase was relatively low (around 30° C.), a period during which DAHP synthase activity is rapidly decaying (Tribe, 1976). Therefore, the findings from this work together with those from tryptophan work support the suggestion by Tribe that in the biosynthesis of aromatic amino acids the first reaction of the common pathway is a significant rate-limiting step (Tribe and Pittard, 1979).

5.2.2 Medium formulation

Carbon source

It was found from the results shown in FIG. [21] and Table 4.6 that the maximum product yield was obtained when the glucose concentration in the culture medium was approximately two-fold higher than the level which was needed to support the actual cell growth of the phenylalanine overproducing strain. It was also concluded that phenylalanine overproducing strains required significantly more carbon substrate for growth compared to the wild-type strains. There are two lines of evidence to support this. Firstly, it can be estimated from the data shown in FIG. [21] that strain NST37 requires approximately 5.6 g of glucose to yield a cell crop of 1 g dry weight, whereas the values for wild types based on Neidhardt's values for various enteric bacteria are estimated as 2.5 g of glucose per g cells (Neidhardt et al., 1974). Secondly, this conclusion is supported by a continuous culture experiment in which the specific glucose uptake rates for a phenylalanine overproducing strain were found to be consistently higher at all growth rates examined than those for the non-producing wild-type reference strain (refer to FIG. [29]).

Phosphate effects

In this study high concentration of inorganic phosphate was found to have a significant effect on the production of phenylalanine, and maximum phenylalanine yield was obtained from the cultures grown under phosphate-limiting conditions (see Table 4.4 and FIG. [20]). But the high concentration of phosphate was found to have no effect at all on the in vivo rate of DAHP synthesis by an experiment using an aroB⁻ strain (data not presented). This finding suggests that inorganic phosphate gives an effect on some stages after the first reaction of the common pathway in the biosynthesis of phenylalanine. A similar phosphate effect has also been observed in tryptophan biosynthesis with *Asp. fumigatus;* high concentration of phosphate was reported to inhibit the activity of tryptophan synthetase and thus to decrease the intracellular level of tryptophan of this organism (Rao et al., 1975). Another relevant report with regard to phosphate limitation is that of Alton et al. (1974) who find that in balanced growth under conditions of phosphate limitation, *E. coli* makes an amount of RNA well beyond what would appear to be the theoretical requirement for growth. This extra RNA corresponds to unused protein synthetic capacity that is not in use in phosphate-limited growth. However, these ribosomes actually engaged in protein synthesis do operate as efficiently as in faster growing cells.

Nitrogen supply

In connection with nitrogen parameters, Kinoshita et al. (1958, 1972) reported that excess ammonia inhibits glutamic acid production by Corynebacterium species. In contrast to this observation, one of the characteristic conditions for L-proline production by Brevibacterium species was reported to be a high concentration of ammonium ions in culture medium (Chibata et al., 1968; Kato et al., 1968). Furthermore, ammonium levels have a critical effect on tryptophan output by mutants of *E. coli* (Tribe, personal communication). In the current work it is clear that excess amounts of nitrogen source favours product formation. No inhibitory effect on phenylalanine production was observed by the presence of the excess amount of nitrogen indicated in Table 4.3.

In summary, from the studies described in sections 4.1 and 4.2, the conditions which have been defined as affecting phenylalanine yield can be summarized as follows: (i) the optimal temperature is 33° C., (ii) the optimal pH of the culture broth is 7.0, (iii) the glucose concentration in culture medium has to be at least 1.8-fold higher than the level being able to yield the actual cell mass, (iv) the nitrogen source has also to be added in excess; approximately 3-fold higher than the amount equivalent to the actual cell mass, (v) with the phosphate-limiting medium, maximum phenylalanine yield can be achieved.

Other factors are also likely to affect yield. For example, in the fermentor experiments it was noted that there was a significant difference in kinetic parameters obtained with the same strain in different fermentors (see Table 4.9). Significant enhancements, especially in specific growth rate ($\mu$) and phenylalanine yield per mass of cells (Yp/x) were observed with the culture in a 5 liter fermentor compared to the values from the culture in a 1 liter fermentor. One of the causes of this improvement may be found in the fact that the five liter fermentor has generally much better oxygen transfer characteristics compared to the 1 liter fermentor used in these experiments. It is difficult, however, to predict exactly the effects of oxygen levels on this fermentation. For example, in their work with *B. lactofermentum*, Akashi et al. (1979) have found the maximum phenylalanine yield was obtained with an insufficient oxygen supply, when the dissolved oxygen tension in the fermentor was recorded as zero. On the other hand, as reviewed by Hirose and Okada (1979), different oxygen effects are obtained in other amino acid production systems. As noted earlier, further work is necessary to define the cause of the yield improvement with the 5 liter fermentor.

5.3 Findings in the continuous culture experiments

The continuous culture experiments enabled the relationship between growth rate and phenylalanine formation to be defined in some detail. As pointed out in section 5.2.1, the final product concentration in the effluent fluid is one of the most important parameters for process evaluation from an industrial viewpoint. Since effluent phenylalanine concentrations decreased very considerably at higher dilution rates (see FIGS. [27] and [30], it would seem best to operate the continuous process at low dilution rate (approximately 0.05 $h^{-1}$), despite the fact that higher values of volumetric productivity and specific productivity were obtained at higher dilution rates.

One of the more interesting findings was that phenylalanine yield per mass of substrate glucose consumed was essentially independent of growth rate, despite considerable variation in rates of glucose consumption at different growth rates (see FIGS. [28], [29] and [30]). Another way of stating these results is that glucose consumption and phenylalanine formation vary in a coordinate fashion, and that product formation and glucose consumption are closely coupled; on the other hand, phenylalanine formation is not strictly growth-associated. This phenomenon is probably due to some common control influencing both glucose catabolism and phenylalanine formation.

It is worth noting that lack of strictly growth-associated kinetics has also been found with glutamic acid production by *Micrococcus glutamicus* (Ueda, 1969).

5.4 Feasibility assessment of the process

To aid in assessment of process feasibility, a number of comparisons of process parameters were made, and these are presented in Tables 5.1 and 5.2.

In Table 5.1, the results of batch and continuous culture experiments with strain NST74 are compared. The most important feature of this comparison is the more favourable values for product yield Yp/x and Yp/s in continuous culture as compared to batch values. It is also worth noting again that the relatively high values of product concentration are obtained using low dilution rates.

TABLE 5.1

COMPARISON OF PROCESS PARAMETERS OBTAINED FROM A BATCH AND A CONTINUOUS PROCESS IN A 1 LITRE FERMENTOR USING STRAIN NST74.

| | Culture Process | |
|---|---|---|
| Parameter | Batch process[a] | Continuous process[b] |
| (final) cell mass (g/l) | 1.45 | 2.23 |
| Phenylalanine concentration (g/l) | 1.98 | 4.00 |
| Specific growth rate $\mu$ ($h^{-1}$) | 0.47 | 0.05 |
| Specific productivity $q_p$ (g/g/h) | 0.12 | 0.09 |
| Product yield Yp/s (g/g) | 0.15 | 0.18 |
| Product yield Yp/x (g/g) | 1.37 | 1.78 |
| Biomass yield Yx/s (g/g) | 0.12 | 0.10 |

TABLE 5.2

COMPARISON BETWEEN PARAMETERS FOR THE PRESENT PROCESS AND THOSE FOR MICROBIAL PHENYLALANINE, TRYPTOPHAN AND LYSINE PRODUCTION REPORTED BY OTHER WORKERS.

| Process | Process Time (h) | Final cell density (g/l) | Final Product Concn. (g/l) | Yield $Y_{p/x}$ (g/g) | Yield $Y_{p/s}$ (g/g) | Average productivity[h] (g/l/h) |
|---|---|---|---|---|---|---|
| Batch process[a] | 30 | 8.1 | 10.9 | 1.38 | ND[f] | 0.32 |
| Continuous process[b] | | 6.2 | 8.7 | 1.40 | 18.9 | 0.44 |
| Phenylalanine production by Brevibacterium lactofermentum | 60 | —[g] | 17.3 | — | 13.9 | — |
| Tryptophan production by E. coli[d] | 10.8 | 6.3 | 1.7 | 0.27 | 8.9 | 0.16 |
| Lysine production by C. glutamicum[e] | 50 | 26 | 41.3 | 1.59 | 27.0 | 0.82 |

[a]Values are taken from the results shown in FIG. [26].
[b]Values are calculated from data from the experiment of FIG. [32].
[c]Taken from the work by Akashi et al., 1979
[d]Taken from the work by Tribe, 1976.
[e]Values from Hagino and Nakayama, 1975.
[f]ND = not determined
[g]— = not available
[h]Data refer to the time of peak productivity in batch cultures
[a]The parameters for the batch culture were calculated from the results shown in FIG. [25].
[b]The values for the continuous process were from the experiment shown in FIG. [30].

Table 5.2 shows a comparison of process parameters with the published values for a commercially viable lysine production by *Corynebacterium glutamicum*, and data for phenylalanine production by *Brevibacterium lactofermentum*, and also tryptophan production by mutants of *E. coli*. The intention in making these particular comparisons is to make, in the absence of a detailed cost evaluation, a preliminary assessment of the commercial feasibility of the current work using other processes as a yardstick. Before discussing these comparisons with systems studied by other workers, it is worth noting that Table 5.2 provides additional support to the comment made with reference to the previous table that the continuous process has more potential than the batch process for phenylalanine production.

As can be seen from Table 5.2, it is difficult to make an exact comparison between the present process and that using *B. lactofermentum* since no information on cell mass as dryweight base is available for the latter. However, the process time with *B. lactofermentum* is just two-fold longer than that for the present process, and consequently the *B. lactofermentum* process would, almost certainly, give lower productivity even though this process shows higher final product concentration in the culture fluid. Another disadvantage of the *B. lactofermentum* process is the fact that the culture medium for this microorganism was complex, containing biotin, DL-methionine, tyrosine, fumaric acid, acetic acid and soybean hydrolysate, contrasting with the defined low cost simple medium used for the present process.

On the other hand, referring to the comparison between the present and the lysine process cited in the table, it can be seen that the lysine process shows much higher final cell density, higher product level and also higher productivity compared to the values for the current phenylalanine process. However, if the present process can be operated at comparable cell densities with the lysine process, these differences in the final product level and in the process productivity could be considerably reduced. Failure to achieve cell densities higher than 6–8 g/l with many of the strains used in this study continues to be the most important problem with the current process. Quite likely this problem is due to inhibition of growth by volatile organic acids such as acetic acid and lactic acid, as reported by Landwall and Holme (1977). There would seem to be considerable strain to strain variation in sensitivity to growth inhibition by these acids, and it is encouraging to note that, firstly, yield of phenylalanine per mass of cells (Yp/x) is little affected by variation in final cell densities (see Table 4.12), and that secondly, there is a report showing that yields of exponentially growing *E. coli*, up to 55 g dry weight of cells per liter of culture broth, have been achieved in glucose minimal medium (Shiloach and Bauer, 1975).

Parameters for a process for tryptophan production by mutants of *E. coli* are shown in Table 5.2. This particular process is included for comparison because this was developed with mutants of *E. coli* which have similar genetic backgrounds with the strains used in the phenylalanine processes. But the tryptophan yield and productivity are significantly lower than those for the present phenylalanine process.

Finally a comment should be made about the problems of instability with continuous culture. In the present experiments (see section 4.5, particularly FIG. [32], continuous culture was carried out for considerable periods with no evidence being obtained for significant decay in culture performance such as may arise by overgrowth of the strains by less productive mutants. It is suggested that the main reason this was possible is that glucose and ammonia were kept in excess, and that under these conditions high producing strains suffer no serious growth disadvantage because they are able to increase their rates of substrate metabolism above the values shown by the wild-type. Direct evidence for such an increased metabolic rate is presented in FIG. [29]. Furthermore, no serious contamination problems were encountered in the course of this work, and therefore there seems to be considerable potential in a continuous process based on the multiple-mutation strains developed . . . .

As another approach for increasing the intracellular level of these enzymes, aroG gene might be fused to the exogenous "powerful" promoters to maximizing expression of this gene as has been achieved with λ-trp phage (Hopkins et al., 1976) and λ-polA phage (Murray et al., 1979) for amplification of the respective gene products.

New regulatory mutations have been recently characterized in the laboratory of A. J. Pittard.... In these mutants the synthesis of chorismate-p-prephenate dehydratase was derepressed and enzyme levels higher than those obtained with pheO$^c$ mutants were obtained (A. J. Pittard, personal communication). Hence, there would be some merit in investigating these mutations for effects on phenylalanine formation. Alternatively, the level of the phenylalanine terminal pathway enzymes may be increased by manipulating the copy-number of the plasmids already isolated in this work (see section 3.2.2), exploiting the pheA gene dosage effect by controlling environmental conditions such as, perhaps, phosphate-limitation (Cassio et al., 1975).

Finally, the area of investigation which is considered to be most critical for further development of this process is continuous culture at high cell densities. If the difficulties in obtaining cell growth to high cell densities do, in fact, prove to be due to inhibition by volatile organic acids, further investigation of continuous culture at different pH values may be productive. Alternatively, dialysis culture may be useful, as in the studied of Landwall and Holme (1977, 1978), who in studies of *E. coli B* noted that the growth inhibition of these cells depended on the accumulation of end-products of fermentative degradation of glucose, and that the removal of these dialysable growth-inhibitory metabolites greatly increased the bacterial yeilds in glucose minimal media. They achieved 130 g/l dry weight of *E. coli B* cells in a glucose-limited dialysis culture with oxygen in excess, whereas 15 g/l dry weight of the cells was obtained in nondialysis culture under the same conditions, and only 6–8 g/l was obtained with the particular genetic background used for the experiments described [herein].

BIBLIOGRAPHY

Abbott, B. J., Appl. Microbiol. 28, 58 (1974)
Adelberg, E. A., J. Bacteriol. 76, 326 (1958)
Adelberg, E. A., M. Mandel and G. C. C. Chen, Biochim. Biophys. Res. Commun., 18, 788 (1965)
Aiba, S., A. E. Humphrey and N. F. Millis, Biochemical Engineering, 2nd ed. (Academic Press) (1973)
Akashi, K., H. Shibai and Y. Hirose, J. Ferment. Technol. 57, 321 (1979)
Alton, T. H. and A. L. Koch, J. Mol. Biol. 86, 1 (1974)
Araki, K., H. Ueda and S. Saigusa, Agr. Biol. Chem. 38, 565 (1974)
Bachmann, B. J. and K. B. Low, Microbiol. Rev. 44, 1 (1980)
Ballou, C. E., H. O. L. Fisher and D. L. MacDonald, J. Amer. Chem. Soc. 77, 5969 (1955)
Berlyn, M. B. and N. H. Giles, J. Bacteriol. 99, 222 (1969)
Bertrand, K., L. Korn, F. Lee, T. Platt, C. L. Squires, C. Squires and C. Yanofsky, Science 189, 22 (1975)
Brown, K. D., Genetics 60, 31 (1968)
Brown, K. D., J. Bacteriol. 104, 177 (1970)
Brown, K. D. and R. L. Somerville, J. Bacteriol. 108, 386 (1971)
Brown, K. D., Proc. Aust. Biochem. Soc. 12, Q2 (1979)
Calhoun, D. H. and R. A. Jensen, J. Bacteriol. 109, 365 (1972)
Camakaris, J. and J. Pittard, J. Bacteriol. 107, 206 (1971)
Camakaris, J. and J. Pittard, J. Bacteriol. 115, 1135 (1973)
Camakaris, J. and J. Pittard, J. Bacteriol. 120, 590 (1974)
Camakaris, H. Ph.D. thesis, University of Melbourne (1975)
Caro, L. and C. M. Berg, In Methods in enzymology (Ed. L. Grossman, K. Moldave,) 21, 444 (1971)
Cassio, D., Y. Mathien and J. P. Waller, J. Bacteriol. 123, 580 (1975)
Chesne, S. and J. Pelmont, Biochimie 56, 631 (1974)
Chesne, S., A. Montmitonnet, J. Pelmont, Biochimie 57, 1029 (1975)
Chibata, I., T. Kamimoto and J. Kato, Appl. Microbiol. 13, 638 (1965)
Chibata, I., M. Kisumi, J. Kato, S. Horie and S. Komatsubar, Amino acid and Nucleic acid 17, 163 (1968)
Chibata, I., T. Tosa and T. Sato, Methods in enzymology 44, 739 (1976)
Clewell, D. B., J. Bacteriol. 110, 667 (1972)
Coats, J. H. and E. W. Nester, J. Biol. Chem. 242, 4948 (1967)
Cohen, S. N., A. C. Y. Chang and L. Hsu, Proc. Nat. Acad. Sci. 69, 2110 (1972)
Collier, R. H. and G. Kohlhaw, J. Bacteriol. 112, 365 (1972)
Cotton, R. G. H. and F. Gibson, Biochim. Biophys. Acta 100, 76 (1965)
Crosby, G. A., Critical reviews in food science and nutrition. 7, 297 (1976)
Crawford, I., Microbiol. Rev. 39, 88 (1975)
Davidson, B. E., E. H. Blackburn and T. A. A. Dopheide, J. Biol. Chem. 247, 4441 (1972)
Davis, B. D., J. Bacteriol. 64, 729 (1952)
Davis, B. D. Nature, 169, 534 (1952)
Dawson, R. M. C. and W. H. Elliott, In Data for biochemical research, 2nd ed. (Ed. R. M. C. Dawson, D. C. Elliott, W. H. Elliott and K. M. Jones; Clarendon Press) p. 475 (1969)
Dayan, J. and D. B. Sprinson, In Methods in enzymology. 17 (Ed. H. Tabor and C. W. Tabor; Academic Press) p. 559 (1970)
Dayan, J. and D. B. Sprinson, J. Bacteriol. 108, 1174 (1971)
Dopheide, T. A. A., P. Crewther and B. E. Davidson J. Biol. Chem. 247, 4447 (1972)
Doy, C. H. and K. D. Brown, Biochim. Biophys. Acta. 104, 377 (1965)
Elsworth, R., G. H. Capell and G. C. Telling, J. Appl. Bact. 21, 80 (1958)
Ely, B. and J. Pittard, Proc. Aust. Biochem. Soc. 8, 56 (1975)
Ely, B. and J. Pittard, J. Bacteriol. 138, 933 (1979)
Enei, H., H. Nakazawa, H. Matsui, S. Okumura, and H. Yamada., FEBS Letters 21, 39 (1972)
Ezekiel, D. H., Biochim. Biophys. Acta. 95, 54 (1965)
Forrest, W. W. and D. J. Walker, Adv. Microb. Physiol. 5, 226 (1970)
Fraenkel, D. G. and R. T. Vinopal, Ann. Rev. Microbiol. 27, 69 (1973)
Fukui, S., S. Ikeda, M. Fujimura, H. Yamada and H. Europ. J. Appl. Microbiol. 1, 25 (1975)
Gelfand, D. H. and R. A. Steinberg, J. Bacteriol. 130, 429 (1977)
Gelfand, D. H. and N. Rudo, J. Bacteriol. 130, 441 (1977)
Gething, M. J. H. and B. E. Davidson, Eur. J. Biochem. 71, 317 (1976)

Gething, M. J. H., B. E. Davidson and T. A. A. Dopheide Eur. J. Biochem. 71, 327 (1976)

Gething, M. J. H. and B. E. Davidson, Eur. J. Biochem. 78, 111 (1977).

Gibson, F., Biochem J. 90, 256 (1964),

Gibson, F., In Methods in enzymology. 17A. (Ed. S. P. Colowick and N. O. Kaplan; Academic Press) p. 362 (1970)

Gibson, F. and J. Pittard, Bacteriol. Rev. 32, 465 (1968)

Gollub, E. G., K. P. Liu and D. B. Sprinson, J. Bacteriol. 115, 121 (1973)

Good, N. E. and S. Izawa., In Methods in enzymology. 24B (Ed. A. San Pietro: Academic Press) p. 53 (1972)

Guterman, S. K. and L. Dann, J. Bacteriol. 114, 1225 (1973)

Guerry, P., D. J. LeBlanc and S. Falkow, J. Bacteriol. 116, 1064 (1973)

Hagino, H. and K. Nakayama., Agr. Biol. Chem. 38, 159 (1974)

Hagino, H., H. Yoshida, F. Kato, Y. Arai, R. Katsumata and K. Nakayama, Agr. Biol. Chem. 37, 2001 (1973)

Hagino, H. and K. Nakayama, Agr. Biol. Chem. 37, 2007 (1973)

Hagino, H. and K. Nakayama, Agr. Biol. Chem. 37, 2013 (1973)

Hagino, H. and K. Nakayama, Agr. Biol. Chem. 39, 343 (1975)

Hardmann, J. G., In Cyclic AMP, Academic Press, p. 433 (1971)

Hempfling, W. P. and S. E. Mainzer, J. Bacteriol. 123, 1076 (1975)

Hershfield, V., H. B. Boyer, C. Yanofsky, M. A. Lovett and D. R. Helinsky, Proc. Nat. Acad. Sci. U.S.A. 71, 3455 (1974)

Hirose, Y., K. Sano and H. Shibai Ann. Reps. Ferm. Proc. 2, 55 (1978)

Hirose, Y. and H. Okada, Microbial production of amino acids. In Microbial technology. 2nd edition (Ed. H. J. Peppler and D. Perlman; Academic Press) p.211 (1979)

Hong, J. S. and B. N. Ames, Proc. Nat. Acad. Sci. U.S.A. 68, 3158 (1971)

Hopkins, A.S., N. E. Murray and W. J. Brammar, J. Mol. Biol. 107, 549 (1976)

Imomoto, F., N. Morikawa and K. Sato, J. Mol. Biol. 13, 169 (1965)

Im, S. W. K. and J. Pittard, J. Bacteriol. 106, 784 (1971)

Im, S. W. K., H. Davidson and J. Pittard, J. Bacteriol. 108, 400 (1971)

Im, S. W. K., Ph.D. Thesis, University of Melbourne (1973)

Im, S. W. K. and J. Pittard, J. Bacteriol. 115, 1145 (1973)

Ito, J. and I. P. Crawford, Genetics 52, 1302 (1965)

Itoh, T., K. Toki, I. Chibata and R. Yoshida, In Synthetic production and utilization of amino acids; Halstead Press. p.243 (1974)

Jackson, E. N. and C. Yanofsky, J. Mol. Biol. 76, 89 (1973)

Johnson, M. J., J. Borkowski and C. Engblom, Biotech and Bioeng. 6, 457 (1964)

Kato, J., S. Horie, S. Komatsubara, M. Kisumi and I. Chibata, Appl. Microbiol. 16, 1200 (1968)

Kinoshita, S., M. Udaka and M. Shimono, J. Gen. Appl. Microbiol. 3, 193 (1957)

Kinoshita, S., K. Tanaka, S. Udaka, S. Akita, K. Saito and T. Iwasaki, J. Ferment. Ass. Japan 16, 1 (1958)

Kinoshita, S. and K. Tanaka, In the microbial production of amino acids (Ed. K. Yamada, S. Kinoshita, T. Tsumoda and K. Aida; Halstead Press) p.267 (1972)

Kitahara, K., S. Fukui and M. Misawa, J. Gen. Appl. Microbiol. 5, 74 (1959)

Kleckner, N., J. Roth and D. Botstein, J. Mol. Biol. 116, 125 (1977)

Kline, E. L., C. S. Brown, W. G. Coleman Jr., and H. E. Umbarger., Biochem. Biophys. Res. Commun. 57, 1144 (1974)

Koch, G. L. E., D. C. Shaw and F. Gibson, Biochim. Biophys. Acta. 229, 759 (1971)

Komatsubara, S., M. Kisumi and I. Chibata, Appl. Environ. Microbiol. 38, 1045 (1979)

Kornberg, H. L., FEBS Symposium 19, 5 (1969)

Kornberg, H. E., Symp. Soc. Exp. Biol. 27, 175 (1973)

Kubota, K., K. Kageyama, T. Shiro and S. Okumura, Amino acids and Nucleic acids 23, 43 (1971)

Kumagai, H., Y. J. Choi, S. Samejima and H. Yamada, Biochem. Biophys. Res. Commun. 59, 789 (1974)

Landwall, P. and T. Holme, J. Gen. Microbiol. 103, 345 (1977)

Landwall, P. and T. Holme, J. Gen. Microbiol. 103, 353 (1977)

Lederberg, J. and E. M. Lederberg, J. Bacteriol. 63, 399 (1952)

Lowry, O. H., N. J. Rosebrough, A. L. Farr and R. J. Randall, J. Biol. Chem. 193, 265 (1951)

Marconi, W., F. Bartoli, F. Cecere and F. Morisi, Agr. Bil. Chem. 38, 1343 (1974)

Margolin, P., In Metabolic Regulation, Metabolic pathways 5, (Ed. H. J. Vogel: Academic Press). p.389 (1971)

Martin, J. F., In Adv. Biochem. Engng. 6, 105 (1977)

Mazur, R. H., J. M. Schlatter and A. H. Goldkamp, J. Am. Chem. Soc. 91, 2684 (1969)

Mazur, R. H., J. A. Reuter, K. A. Swiatek and J. M. Schlatter, J. Med. Chem. 16, 1284 (1973)

McCandliss, R. J., M. D. Poling and K. Hermann, J. Biol. Chem. 253, 4529 (1978)

McCray, J. W. and K. M. Hermann, J. Bacteriol. 125, 608 (1976)

Miller, G. L., R. Blum, W. E. Glennon and A. L. Burton, Anal. Biochem. 2, 127 (1960)

Monod, J., G. Cohen-Bazire and M. Cohen, Biochim. Biophys. Acta. 17, 585 (1951)

Morse, D. E. and C. Yanofsky, J. Mol. Biol. 44, 185 (1969)

Murgola, E. J. and C. Yanofsky, J. Bacteriol. 117, 444 (1974)

Murray, N. E. and W. S. Kelley, Molec. Gen. Genet. 175, 77 (1979)

Nakanishi, T., J. Nakajima and K. Kanda, J. Ferment. Technol. 53, 543 (1975)

Nakayama, K., S. Kitaka and S. Kinoshita, J. Gen. Appl. Microbiol. 7, 145 (1961)

Nakayama, K. Process Biochemistry 12 (2), 4 (1976)

Nakazawa, H., H. Enei, S. Okumura, H. Yashida and H. Yamada, FEBS Letters 25, 43 (1972)

Neidhardt, F. C., P. L. Bloch and D. F. Smith, J. Bacteriol. 119, 736 (1974)

Ohgishi, H., D. Nishikawa, H. Kumagai and H. Yamada, Agr. Chem. Soc. Japan. Abst., 90 (1977)

Ozaki, S., K. Kono, S. Okumura, H. Okata and K. Sakaguchi, Proc. Symp. Amino acids Ferment., 2nd. p.4 (1960)

Pabst, M. J., J. C. Kuhn and R. L. Somerville, J. Biol. Chem. 248, 901 (1973)

Pintauro, N. D. (1977), Sweeteners and enhancers. (Noyes Data Corp).

Piperno, J. R. and D. L. Oxender, J. Biol. Chem. 243, 5914 (1968)

Pirt, S. J. (1975), Principles of microbe and cell cultivation (Blackwell Scientific Publications)

Pittard, J. and B. J. Wallace, J. Bacteriol. 91, 1494 (1966)

Pittard, J., J. Camakaris and B. J. Wallace, J. Bacteriol. 97, 1242 (1969)

Pittard, J. and F. Gibson, In Current topics in cellular regulation. 2. (Ed. B. L. Horecker and E. R. Stadtman; Academic Press) p.29 (1970)

Pittard, A. J., Proc. Aust. Biochem. Soc. 12, 123 (1979)

Rao, K. K. and A. R. Gupta. Natur Wissenschaften. 62, 394 (1975)

Robbers, J. E., L. W. Robertson, K. M. Hornemann, A. Jindra and H. G. Floss, J. Bacteriol. 112, 791 (1972)

Roberts, R. B., P. H. Abelson, D. B. Cowie, E. T. Bolton and R. J. Britten., Studies of biosynthesis in *Escherichia coli*. Carnegie Institute of Washington Publ. No. 607, Carnegie Institute of Washington, Washington, D.C. 1955)

Rosenberg, H. and I. G. Young., Iron transport in the enteric bacteria; In Microbial iron metabolism. (Ed. J. B. Neilands; Academic Press) p. 67 (1974)

Rudman, D. and A. Meister, J. Biol. Chem. 200, 591 (1953)

Sano, K. and I. Shiio., J. Gen. Appl. Microbiol. 13, 349 (1967)

Sano, K. and I. Shiio, J. Gen. Appl. Microbiol. 16, 373 (1970)

Sano, K. and I. Shiio, J. Gen. Appl. Microbiol. 17, 97 (1971)

Sano, K., C. Euchi, N. Yasuda and K. Mitsugi, Agr. Chem. Soc. Japan Abst., 431 (1977)

Schmit, J. C., S. W. Artz and H. Zalkin, J. Biol. Chem. 245, 4019 (1970)

Schoner, R. and K. M. Herrmann, J. Biol. Chem. 251, 5440 (1976)

Sebek, O. K. and Laskin, A. I. (1979), Genetics of Industrial Microorganisms. (Proceedings Third Int. Symp. Genet. Industrial Microorgs.) American Soc. Microbiol. Washington Shiio, I. and R. Miyajima, J. Biochem. 65, 849 (1969)

Shiloach, J. and S. Bauer, Biotech. and Bioeng. 17, 227 (1975)

Sibert, D. F., S. E. Jorgense and E. C. C. Lin, Biochim. Biophys. Acta. 73, 232 (1963)

Simpson, R. J., B. E. Davidson, T. A. A. Dopheide, S. Andrews and J. Pittard., J. Bacteriol. 107, 798 (1971)

So, M., R. Gill and S. Falkow, Mol. Gen. Genet. 142, 239 (1975)

Somerville, R. L. and C. Yanofsky, J. Mol. Biol. 11, 747 (1965)

Srinivasan, P. R. and D. B. Sprinson, J. Biol. Chem. 234, 716 (1959)

Srinivasan, P. R., D. B. Sprinson and J. Rothschild, J. Biol. Chem. 238, 2176 (1963)

Sugimoto, S., M. Nakagawa, T. Tsuchida and I. Shiio, Agr. Biol. Chem. 37, 2327 (1973)

Taussky, H. H. and E. Shore, J. Biol. Chem., 202, 675 (1953)

Tempest, D. W., Trends in Biochemical Sciences (TIBS). August. p. 180 (1978)

Terui, G. and H. Nittsu, Biotechnol. Bioeng. Symp. 1, 33 (1969)

Thorne, G. M. and L. M. Corwin, J. Gen. Microbiol. 90, 2 (1976)

Tribe, D. E., Ph.D. Thesis, University of Melbourne (1976)

Tribe, D. E., H. Camakaris and J. Pittard, J. Bacteriol. 127, 1085 (1976)

Tribe, D. E. and J. Pittard, Appl. Environ. Microbiol. 38, 181 (1979)

Udaka, S. and S. Konoshita, J. Gen. Appl. Microbiol. 5, 159 (1960)

Udenfriend, S, and J. R. Cooper, J. Biol. Chem. 196, 227 (1952)

Udenfriend, S. and R. E. Peterson, In Methods in enzymology 3 (Ed. S. P. Colowick and N. O. Kaplan; Academic Press) p. 613 (1957)

Ueda, K., In Fermentation Advances (Ed. D. Perlman; Academic Press) p. 43 (1969)

Umbarger, H. E., Ann. Rev. Biochem. 47, 533 (1978)

Wallace, B. J. and J. Pittard, J. Bacteriol. 93, 237 (1967a)

Wallace, B. J. and J. Pittard, J. Bacteriol. 94, 1279 (1967b)

Wallace, B. J. and J. Pittard, J. Bacteriol. 97, 1234 (1969a)

Wallace, B. J. and J. Pittard, J. Bacteriol. 99, 707 (1969b)

Wayne, R. and J. B. Neilands, J. Bacteriol. 121, 497 (1975)

Whipp, M. J., D. M. Halsall and J. Pittard, Proc. Aust. Biochem. Soc. 9, 62 (1976)

Whipp, M. J. and J. Pittard, J. Bacteriol. 132, 453 (1977)

Whipp, M. J., D. M. Halsall and A. J. Pittard, J. Bacteriol. 143, 1 (1980)

Yamada, K., S. Kinoshita, T. Tsumoda and K. Aida, The microbial production of amino acids. Halstead Press (1972)

Yokozeki, K., K. Sano, T. Eguchi, N. Yasuda, I. Noda and K. Mitsugi, Agr. Chem. Soc. Japan Abst. 238 (1976)

Yoshinaga, H., J. Gen. Appl. Microbiol. 15, 387 (1969)

Yoshida, H. and K. Nakayama, Agr. Chem. Soc. 49, 527 (1975)

Young, I. G. and F. Gibson, Biochem. Ciophys. Acta. 117, 401 (1969)

Zalkin, H., Adv. in Enzymol. 38, 1 (1973)

Zurawski, G., K. Brown, D. Killingly and C. Yanofsky Proc. Natl. Acad. Sci. U.S.A. 75, 4271 (1978)"

EXAMPLE 2

A strain of *E. coli* known as NST 37 (ATCC 31882) and carrying seven mutations affecting phenylalanine yield, namely aroF(FBI$^R$) aroG(FBI$^R$) tyrR pheA(F-BI$^R$) pheAo tyrA and trpE, was used in the example. This strain of *E. coli* was cultured at 37° C. and a pH of 6.5 in medium MMT5 to which had been added 2% w/v of glucose and a trace elements solution. The medium MMT5 consisted of, per liter,

| | |
|---|---|
| NH$_4$Cl | 1.93 g |
| K$_2$SO$_4$ | 0.122 g |
| MgCl$_2$ | 0.27 g |
| K$_2$HPO$_4$ | 0.153 g |
| Na Citrate | 0.294 g |
| Fe Cl$_3$ | 0.032 g |
| Trace element solution | 1 ml |

The trace element solution contained

| | |
|---|---|
| $(NH_4)_6(MoO_7)$ | 3 μM |
| $H_3BO_3$ | 400 μM |
| $MnCl_2$ | 80 μM |
| $ZnSO_4$ | 10 μM |

Figure 2:
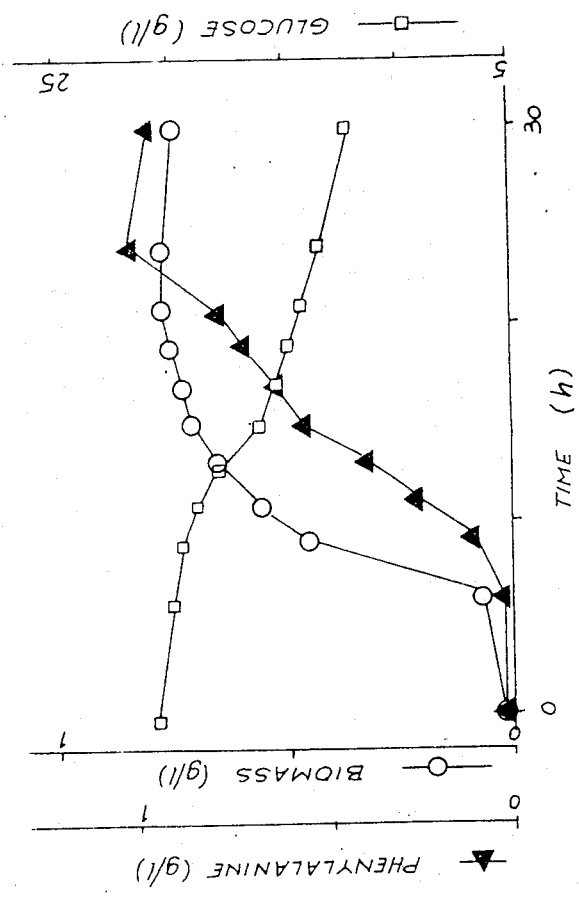
FIG. 2 is a graph showing the kinetics of phenylalanine formation in batch culture.

The culture medium was stirred and aerated in a conventionally designed fermenter to prevent the development of anaerobic conditions. The medium was inoculated with approximately FIG. 2 shows that this strain had an unusually high proportion of metabolic activity directed towards phenylalanine production.

EXAMPLE 3

E. coli strain NST 70 (ATCC 31883) has the genetic description aro F (FBI$^R$) aro G (FBI$^R$) tyr R phe A (GBI$^R$) phe Ao tyr A trp E and in addition carries a plasmid p UNT 21 which is a multi-copy plasmid which carries mutant phe Ao phe A (FBI$^R$) phe genes.

In order to compare the activity of strains NST 37 and NST 70 both strains were grown separately in medium MMB 20 g/l glucose plus mg/l tyrosine and tryptophan in shake flasks at 37° C. After 24 hours assays were made of cell growth and phenylalanine. To facilitate comparison the results are expressed as yield of phenylalanine per gram dry weight of cells.

| Strain | Yield (Y P/x % at 24 h.) |
|---|---|
| NST 37 | 75 |
| NST 70 | 129 |

The medium MMB is as follows:

| | |
|---|---|
| $K_2HPO_4$ | 10.6 g/l |
| $NaH_2PO_4$ | 6.1 g/l |
| $(NH_4)_2SO_4$ | 2.0 g/l |
| $MgSO_4.7H_2O$ | 0.2 g/l |
| $Ca(NO_3)_2$ | 0.01 g/l |
| $FeCl_3.6H_2O$ | 0.054 g/l |
| Trisodium citrate $2H_2O$ + 1 ml of trace element solution. | 2.94 g/l |
| The trace element solution | |
| $(NH_4)_6(MoO_7)_{24}$ | 3 μm |
| $H_3BO_3$ | 400 μm |
| $MnCl_2$ | 80 μm |
| $ZnSO_4$ | 10 μm |

EXAMPLE 4

The strain NST.74 (ATCC 31884) of E. coli has the genetic description aro F (FBI$^R$) aro G (FBI$^R$) tyr R phe A (FBI$^R$) phe Ao. This strain was continuously cultured at 33° C. and a pH of 7.0 in a 5 l. fermentor. The pH was controlled by the addition of an alkali solution containing 450 ml of 5M NaOH
250 ml of 5M KOH
300 ml of 3.5M NH$_4$OH The organism was cultured in a medium comprising

| | |
|---|---|
| glucose | 70.0 g/l |
| Vitamin B1 0.017% | 4.0 g/l |
| citrate | 3.0 g/l |
| FeCl$_3$ | 3.0 g/l |
| Trace element soln. | 0.04 g/l |
| 0.105 M K$_2$SO$_4$ | 20.0 g/l |
| 0.2 M MgCl$_2$ | 20.0 g/l |

-continued

| | |
|---|---|
| 2.7 M NH$_4$Cl | 47.0 g/l |
| 0.264 M K$_2$HPO$_4$ | 13.2 g/l |

The culture medium was aerated with air (800 ml/min) and oxygen (200~250 ml/min) to give a dissolved oxygen tension of at least 20% saturation.

The cultured organism showed a specific growth rate of 0.05 hr$^{-1}$ which corresponds to a dilution rate of 5 ml per liter of fermentor per hour.

As is seen in FIG. 3 the culture showed a consistently high production of phenylalanine for 204 hours.

I claim:

1. A strain of *Escherichia coli* having altered production of 3-deoxy-D-arabino-heptulosonate-7-phosphate (DAHP) synthase and chorismate mutase P-prephenate dehydratase (CMP-PDH), wherein
   (i) said DAHP synthase is not subject to feedback inhibition by phenylalanine, tryosine, or tryptophan present within the microorganism and said DAHP synthase either
      (a) is not subject to repression by phenylalanine, tyrosine, or tryptophan or
      (b) is produced in greater amount than is produced by wild type *E. coli* and
   (ii) said CMP-PDH is not subject to feedback inhibition by phenylalanine and said CMP-PDH either
      (a) is not subject to repression by phenylalanine or
      (b) is produced in a greater amount than produced by wild type *E. coli.*

2. A strain of *E. coli* as in claim 1 having altered production of shikimate kinase wherein
   (i) said shikimate kinase is not repressed by phenylalanine, tyrosine, or tryptophan or
   (iii) the amount produced is greater than that produced by a wild-type *E. coli.*

3. A mutant strain of *E. coli* as claimed in claim 1, known as NST 37 and cataloged as ATCC 31882.

4. A mutant strain of *E. coli* as claimed in claim 1, known as NST 70 and cataloged as ATCC 31883.

5. A mutant strain of *E. coli* as claimed in claim 1, known as NST 74 and cataloged as ATCC 31884.

6. A strain of *E. coli* as claimed in claim 1 in which the DNA of the microorganism is such that DAHP synthase is desensitized to inhibition by both phenylalanine and tyrosine.

7. A strain of *E. coli* as claimed in claim 1 in which the formation of DAHP synthse is desensitized to repression by mutation of the control gene tyr R.

8. A strain of *E. coli* as claimed in claim 2 comprising multi-copy plasmids, each of said multi-copy plasmids having a structural gene for the production of a member of the group consisting of DAHP synthase, CMP-PDH and shikimate kinase.

9. A strain of *E. coli* as claimed in claim 2 in which the metabolic pathways are blocked by mutation of the gene tyr A to block production of tyrosine or mutation of the gene trp E to block production of tryptophan.

10. A method for the production of phenylalanine comprising the steps of culturing a strain of *E. coli* having altered production of 3-deoxy-D-arabino-heptulosonate-7-phosphate (DAHP) synthase and chorismate mutase P-prephenate dehydratase (CMP-PDH), wherein
   (i) said DAHP synthase is not subject to feedback inhibition of phenylalanine, tryosine, or tryptophan present within the microorganism and said DAHP synthase either
  (a) is not subject to repression by phenylalanine, tyrosine, or tryptophan or
  (b) is produced in greater amount than is produced by wild type *E. coli* and
(ii) said CMP-PDH is not subject to feedback inhibition by phenylalanine and said CMP-PDH either
  (a) is not subject to repression by phenylalanine or
  (b) is produced in a greater amount than produced by wild type *E. coli;* in a media containing a carbohydrate and recovering the phenylalanine.

11. A method as claimed in claim 10 in which the carbohydrate is a member selected from the group consisting of glucose, glycerol, xylose, maltose, lactose, lactates and acetic acid.

12. A strain of *E. coli* as claimed in claim 1 which DNA of the microorganism has been further modified to prevent the production from chorismate of end products other than phenylalanine.

* * * * *